US007252985B2

(12) United States Patent
Cheng et al.

(10) Patent No.: US 7,252,985 B2
(45) Date of Patent: Aug. 7, 2007

(54) CAROTENOID KETOLASES

(75) Inventors: Qiong Cheng, Wilmington, DE (US); Luan Tao, Claymont, DE (US); Henry Yao, Boothwyn, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 326 days.

(21) Appl. No.: 11/015,433

(22) Filed: Dec. 17, 2004

(65) Prior Publication Data

US 2005/0227311 A1    Oct. 13, 2005

Related U.S. Application Data

(60) Provisional application No. 60/531,310, filed on Dec. 19, 2003.

(51) Int. Cl.
*C12N 1/20* (2006.01)
*C12N 9/02* (2006.01)
*C07H 21/04* (2006.01)

(52) U.S. Cl. ............... 435/252.3; 435/189; 435/320.1; 435/148; 435/410; 435/254.3; 435/255.2; 435/255.5; 536/23.2

(58) Field of Classification Search ............. 435/252.3, 435/189, 148, 410, 254.3, 255.2, 255.5; 536/23.2
See application file for complete search history.

(56) References Cited

U.S. PATENT DOCUMENTS

| 6,150,130 A | 11/2000 | Misawa et al. |
| 6,551,807 B1 | 4/2003 | Cunningham |
| 2003/0087337 A1 | 5/2003 | Giraud et al. |

FOREIGN PATENT DOCUMENTS

WO    WO 02/079395 A2    10/2002

OTHER PUBLICATIONS

Takakazu Kaneko et al., Complete Genomic Sequence of the Filamentous Nitrogen-fixing Cyanobacterium *Anabaena* sp. Strain PCC 7120, DNA Research, vol. 8:205-213, 2001.
Blanca Fernandez-Gonzalez et al., A New Type of Asymmetrically Acting beta-Carotene Ketolase Is Required for the Synthesis of Echinenone in the Cyanobacterium *Synechocystis* sp. PCC 6803*, J. Biol. Chem., vol. 272(15):9728-9733, 1997.
Norihiko Misawa et al., Metabolic engineering for the production of carotenoids in non-carotenogenic bacteria and yeasts, J. of Biotech., vol. 59:169-181, 1998.
National Center for Biotechnology Information General Identifier No. 5912291, Accession No. Y15112, Sep. 15, 1999, M. Harker et al., Carotenoid biosynthesis genes in the bacterium *Paracoccus marcusii* MH1.
National Center for Biotechnology Information General Identifier No. 2654317, Accession No. X86782, Sep. 9, 2004, M. Harker et al., Biosynthesis of ketocarotenoids in transgenic cyanobacteria expressing the algal gene for beta-C-4-oxygenase, crtO.
National Center for Biotechnology Information General Identifier No. 903298, Accession No. D58422, N. Misawa et al., Canthaxanthin biosynthesis by the conversion of methylene to keto groups in a hydrocarbon beta-carotene by a single gene Biochem. Biophys. Res. Commun. 209(3), 867-876 (1995).
National Center for Biotechnology Information General Identifier No. 61629280, Accession No. D58420, N. Misawa et al., Canthaxanthin biosynthesis by the conversion of methylene to keto groups in a hydrocarbon beta-carotene by a single gene Biochem. Biophys. Res. Commun. 209(3), 867-876 (1995).
National Center for Biotechnology Information General Identifier No. 1136838, Accession No. D45881, Feb. 10, 1999, S. Kajiwara et al., Isolation and functional identification of a novel cDNA for astaxanthin biosynthesis from *Haematococcus pluvialis*, and astaxanthin synthesis in *Escherichia coli*.
National Center for Biotechnology Information General Identifier No. 8650414, Accession No. AF218415, L. Hannibal et al., Isolation and characterization of canthaxanthin biosynthesis genes from the photosynthetic bacterium *Bradyrhizobium* sp. strain ORS278 J. Bacteriol. 182(13), 3850-3853 (2000).
H. J. Nelis et al., Principal carotenoids permitted as additives in foods and feeds, J. of Applied Bacteriology, vol. 70:181-191, 1991.
Laure Hannibal et al., Isolation and Characterization of Canthaxanthin Biosynthesis Genes from the Photosynthetic Bacterium *Bradyrhizobium* sp. Strain ORS278, J. of Bacteriology, vol. 182(13):3850-3853, Jul. 2000.

*Primary Examiner*—Tekchand Saidha

(57) ABSTRACT

Novel CrtW carotenoid ketolase are provided that are useful for the production of ketocarotenoids. The ketolases genes of the present invention exhibit low homology in comparison to other CrtW ketolases previously reported. Expression of the carotenoid ketolases in heterologous hosts enabled production of canthaxanthin and astaxanthin. Coexpression experiments using divergent crtW genes resulted in increased production of the desired ketocarotenoids.

10 Claims, 7 Drawing Sheets

*Brevundimonas vesicularis* DC263

*Flavobacterium sp.* K1-202C

Figure 1:
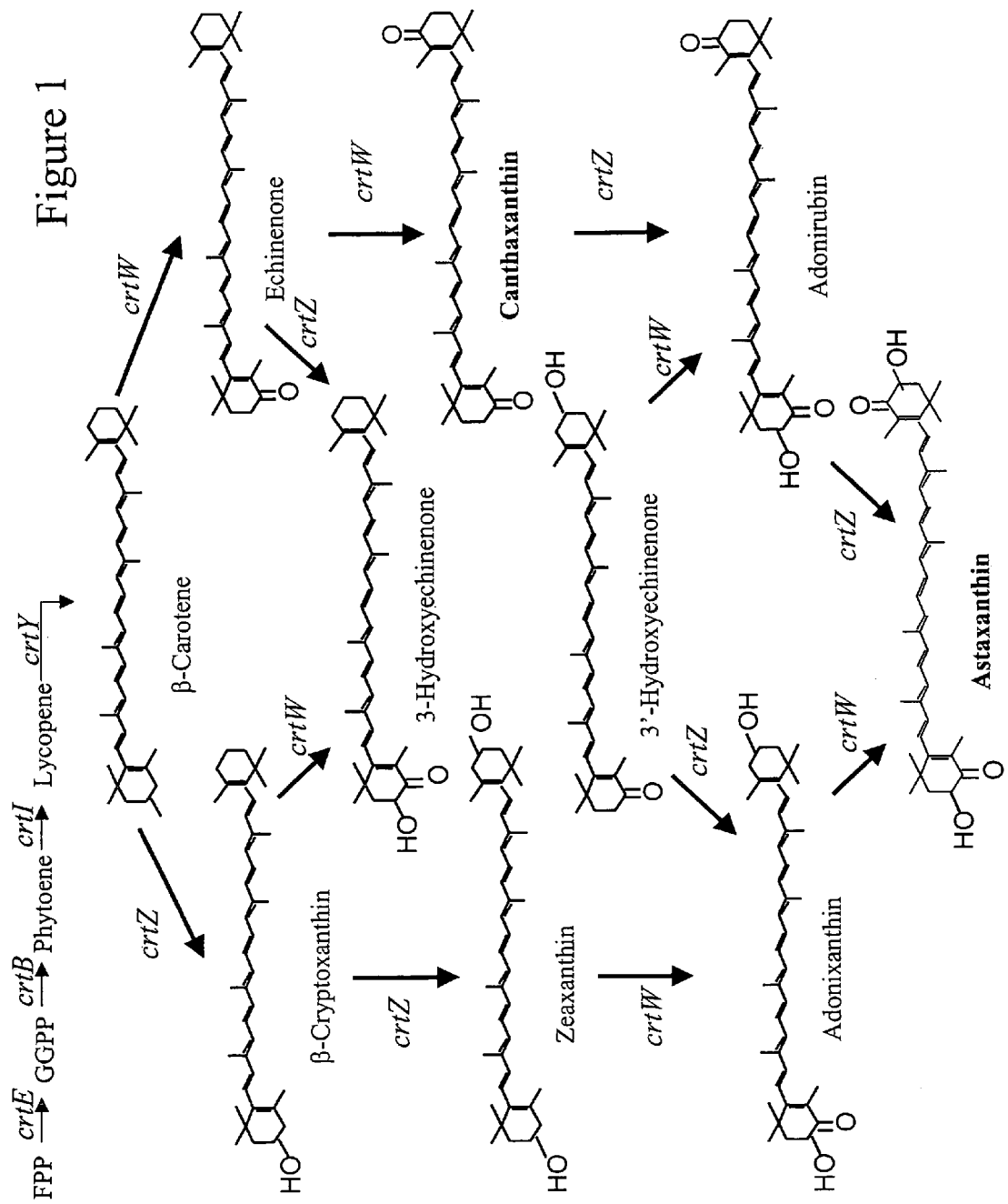

DC18
crtW

DC263
crtW

K1-202C
crtW

MWM1200(pDCQ340)

MWM1200(pDCQ341)

MWM1200(pDCQ342)

SEQUENCE LISTING

<160> NUMBER OF SEQ ID NOS: 33

<210> SEQ ID NO 1
<211> LENGTH: 747
<212> TYPE: DNA
<213> ORGANISM: Sphingomonas melonis DC18
<220> FEATURE:
<221> NAME/KEY: CDS
<222> LOCATION: (1)..(747)

<400> SEQUENCE: 1

```
atg acc gtc gat cac gac gca cgg atc agc ctg ctg ctg gcc gca gcc        48
Met Thr Val Asp His Asp Ala Arg Ile Ser Leu Leu Leu Ala Ala Ala
1               5                   10                  15 atc ggc gcc gcg tgg ctg gcg atc cat gtc ggg gcg atc gtg tgg tgg        96
Ile Gly Ala Ala Trp Leu Ala Ile His Val Gly Ala Ile Val Trp Trp
            20                  25                  30 cga tgg agc ccg gcg acg gcg gtg ctc gcg atc ccc gtc gtg ctc gta       144
Arg Trp Ser Pro Ala Thr Ala Val Leu Ala Ile Pro Val Val Leu Val
        35                  40                  45 cag gcg tgg ctg agc acc ggc ctg ttc atc gtc gcg cac gat tgc atg       192
Gln Ala Trp Leu Ser Thr Gly Leu Phe Ile Val Ala His Asp Cys Met
    50                  55                  60 cac gga tcg ttc gtg ccc ggc cgg ccc gcg gtc aac cgg acc gtc ggg       240
His Gly Ser Phe Val Pro Gly Arg Pro Ala Val Asn Arg Thr Val Gly
65                  70                  75                  80 acg ctg tgc ctc ggc gcc tat gcg gga ctg tcc tat ggc cag ctc cat       288
Thr Leu Cys Leu Gly Ala Tyr Ala Gly Leu Ser Tyr Gly Gln Leu His
                85                  90                  95 ccc aag cat cat gcg cat cac gat gcg ccg ggc acc gcc gcc gac ccc       336
Pro Lys His His Ala His His Asp Ala Pro Gly Thr Ala Ala Asp Pro
            100                 105                 110 gat ttc cat gcc ggc gcg ccg cga tcc gca ctg ccg tgg ttc gcg cgc       384
Asp Phe His Ala Gly Ala Pro Arg Ser Ala Leu Pro Trp Phe Ala Arg
        115                 120                 125 ttc ttc acc agc tat tac acg cac ggc cag atc ctc cgg atc acc gcg       432
Phe Phe Thr Ser Tyr Tyr Thr His Gly Gln Ile Leu Arg Ile Thr Ala
    130                 135                 140 gcg gcg gtg ctg tac atg ctg ctc ggt gtg tcg ctg ctc aac atc gtc       480
Ala Ala Val Leu Tyr Met Leu Leu Gly Val Ser Leu Leu Asn Ile Val
145                 150                 155                 160 gtg ttc tgg gcg ttg ccg gcg ctg atc gcg ctg gcg cag ctg ttc gtc       528
Val Phe Trp Ala Leu Pro Ala Leu Ile Ala Leu Ala Gln Leu Phe Val
                165                 170                 175 ttc ggc acc ttc ctg ccg cat cgc cac ggc gac acg ccg ttc gcg gac       576
```

| | | | | | | | | | | | | | | |
|---|---|---|---|---|---|---|---|---|---|---|---|---|---|---|
| Phe | Gly | Thr | Phe | Leu | Pro | His | Arg | His | Gly | Asp | Thr | Pro | Phe | Ala | Asp |
| | | | 180 | | | | | 185 | | | | | 190 | | |

```
gcg cac aat gcc cgc agc aac ggc tgg cca cgg ctg gcg tcg ctg gcg      624
Ala His Asn Ala Arg Ser Asn Gly Trp Pro Arg Leu Ala Ser Leu Ala
        195                 200                 205 acc tgc ttc cac ttc ggc gcc tat cat cac gaa cat cac ctg agc ccg      672
Thr Cys Phe His Phe Gly Ala Tyr His His Glu His His Leu Ser Pro
    210                 215                 220 tgg acg ccc tgg tgg cag ttg ccg cgc gtc ggc cag cct gcc gcc gga      720
Trp Thr Pro Trp Trp Gln Leu Pro Arg Val Gly Gln Pro Ala Ala Gly
225                 230                 235                 240 cac cgg tcg tta agc aaa gac cgg tag                                  747
His Arg Ser Leu Ser Lys Asp Arg
                245

<210> SEQ ID NO 2
<211> LENGTH: 248
<212> TYPE: PRT
<213> ORGANISM: Sphingomonas melonis DC18

<400> SEQUENCE: 2

Met Thr Val Asp His Asp Ala Arg Ile Ser Leu Leu Ala Ala Ala
1               5                   10                  15

Ile Gly Ala Ala Trp Leu Ala Ile His Val Gly Ala Ile Val Trp Trp
                20                  25                  30

Arg Trp Ser Pro Ala Thr Ala Val Leu Ala Ile Pro Val Val Leu Val
            35                  40                  45

Gln Ala Trp Leu Ser Thr Gly Leu Phe Ile Val Ala His Asp Cys Met
        50                  55                  60

His Gly Ser Phe Val Pro Gly Arg Pro Ala Val Asn Arg Thr Val Gly
65                  70                  75                  80

Thr Leu Cys Leu Gly Ala Tyr Ala Gly Leu Ser Tyr Gly Gln Leu His
                85                  90                  95

Pro Lys His His Ala His His Asp Ala Pro Gly Thr Ala Ala Asp Pro
            100                 105                 110

Asp Phe His Ala Gly Ala Pro Arg Ser Ala Leu Pro Trp Phe Ala Arg
        115                 120                 125

Phe Phe Thr Ser Tyr Tyr Thr His Gly Gln Ile Leu Arg Ile Thr Ala
    130                 135                 140

Ala Ala Val Leu Tyr Met Leu Leu Gly Val Ser Leu Leu Asn Ile Val
145                 150                 155                 160

Val Phe Trp Ala Leu Pro Ala Leu Ile Ala Leu Ala Gln Leu Phe Val
                165                 170                 175

Phe Gly Thr Phe Leu Pro His Arg His Gly Asp Thr Pro Phe Ala Asp
            180                 185                 190

Ala His Asn Ala Arg Ser Asn Gly Trp Pro Arg Leu Ala Ser Leu Ala
        195                 200                 205

Thr Cys Phe His Phe Gly Ala Tyr His His Glu His His Leu Ser Pro
    210                 215                 220

Trp Thr Pro Trp Trp Gln Leu Pro Arg Val Gly Gln Pro Ala Ala Gly
225                 230                 235                 240

His Arg Ser Leu Ser Lys Asp Arg
                245

<210> SEQ ID NO 3
<211> LENGTH: 780
<212> TYPE: DNA
```

<213> ORGANISM: Brevundimonas vesicularis DC263
<220> FEATURE:
<221> NAME/KEY: CDS
<222> LOCATION: (1)..(780)

<400> SEQUENCE: 3

| | | | | | | | | | | | | | | | | |
|---|---|---|---|---|---|---|---|---|---|---|---|---|---|---|---|---|
| atg | cgg | caa | gcg | aac | agg | atg | ctt | acc | ggg | ccg | cga | tgc | gct | aag | tgt | 48 |
| Met | Arg | Gln | Ala | Asn | Arg | Met | Leu | Thr | Gly | Pro | Arg | Cys | Ala | Lys | Cys | |
| 1 | | | | 5 | | | | | 10 | | | | | 15 | | |

| cgc | gcc | atg | tcc | gcc | gtc | acg | cca | atg | tca | cgg | gtc | gtc | ccg | aac | cag | 96 |
|---|---|---|---|---|---|---|---|---|---|---|---|---|---|---|---|---|
| Arg | Ala | Met | Ser | Ala | Val | Thr | Pro | Met | Ser | Arg | Val | Val | Pro | Asn | Gln | |
| | | | 20 | | | | | 25 | | | | | 30 | | | |

| gcc | ctg | atc | ggc | ctg | acg | ctg | gct | ggc | ctg | atc | gcc | gcg | gcc | tgg | ctg | 144 |
|---|---|---|---|---|---|---|---|---|---|---|---|---|---|---|---|---|
| Ala | Leu | Ile | Gly | Leu | Thr | Leu | Ala | Gly | Leu | Ile | Ala | Ala | Ala | Trp | Leu | |
| | | 35 | | | | | 40 | | | | | 45 | | | | |

| acc | ctg | cac | atc | tac | ggc | gtc | tat | ttt | cat | cgc | tgg | acg | atc | tgg | agc | 192 |
|---|---|---|---|---|---|---|---|---|---|---|---|---|---|---|---|---|
| Thr | Leu | His | Ile | Tyr | Gly | Val | Tyr | Phe | His | Arg | Trp | Thr | Ile | Trp | Ser | |
| 50 | | | | | 55 | | | | | 60 | | | | | | |

| gtc | ctg | acc | gtt | ccg | ctg | atc | gtc | gcc | ggc | cag | acc | tgg | cta | tcc | gtc | 240 |
|---|---|---|---|---|---|---|---|---|---|---|---|---|---|---|---|---|
| Val | Leu | Thr | Val | Pro | Leu | Ile | Val | Ala | Gly | Gln | Thr | Trp | Leu | Ser | Val | |
| 65 | | | | | 70 | | | | | 75 | | | | | 80 | |

| ggc | ctg | ttc | atc | gtc | gcc | cac | gac | gcc | atg | cac | ggc | tcg | ctg | gcc | ccg | 288 |
|---|---|---|---|---|---|---|---|---|---|---|---|---|---|---|---|---|
| Gly | Leu | Phe | Ile | Val | Ala | His | Asp | Ala | Met | His | Gly | Ser | Leu | Ala | Pro | |
| | | | | 85 | | | | | 90 | | | | | 95 | | |

| gca | cgc | cca | cgg | ctg | aac | acg | gcg | atc | ggc | agc | ctg | gcg | ctg | gcc | ctc | 336 |
|---|---|---|---|---|---|---|---|---|---|---|---|---|---|---|---|---|
| Ala | Arg | Pro | Arg | Leu | Asn | Thr | Ala | Ile | Gly | Ser | Leu | Ala | Leu | Ala | Leu | |
| | | | 100 | | | | | 105 | | | | | 110 | | | |

| tac | gcc | gga | ttt | cgg | ttc | acg | cct | ttg | aag | acc | gca | cac | cac | gcc | cat | 384 |
|---|---|---|---|---|---|---|---|---|---|---|---|---|---|---|---|---|
| Tyr | Ala | Gly | Phe | Arg | Phe | Thr | Pro | Leu | Lys | Thr | Ala | His | His | Ala | His | |
| | | | 115 | | | | | 120 | | | | | 125 | | | |

| cac | gct | gcg | ccc | ggt | acg | gcg | gac | gat | ccc | gac | ttt | cac | gcc | gac | gcc | 432 |
|---|---|---|---|---|---|---|---|---|---|---|---|---|---|---|---|---|
| His | Ala | Ala | Pro | Gly | Thr | Ala | Asp | Asp | Pro | Asp | Phe | His | Ala | Asp | Ala | |
| | 130 | | | | | 135 | | | | | 140 | | | | | |

| ccg | cgc | gct | ttc | ctg | ccc | tgg | ttc | tac | ggc | ttt | ttc | cgc | acc | tat | ttc | 480 |
|---|---|---|---|---|---|---|---|---|---|---|---|---|---|---|---|---|
| Pro | Arg | Ala | Phe | Leu | Pro | Trp | Phe | Tyr | Gly | Phe | Phe | Arg | Thr | Tyr | Phe | |
| 145 | | | | | 150 | | | | | 155 | | | | | 160 | |

| ggc | tgg | cga | gaa | ctg | gcc | gtt | ctg | acg | gtg | ctc | gtg | gcc | gtt | gcg | gtg | 528 |
|---|---|---|---|---|---|---|---|---|---|---|---|---|---|---|---|---|
| Gly | Trp | Arg | Glu | Leu | Ala | Val | Leu | Thr | Val | Leu | Val | Ala | Val | Ala | Val | |
| | | | | 165 | | | | | 170 | | | | | 175 | | |

| ctg | atc | ctc | ggc | gcc | cgt | atg | ccc | aat | ctt | ctg | gtc | ttt | tgg | gcc | gcg | 576 |
|---|---|---|---|---|---|---|---|---|---|---|---|---|---|---|---|---|
| Leu | Ile | Leu | Gly | Ala | Arg | Met | Pro | Asn | Leu | Leu | Val | Phe | Trp | Ala | Ala | |
| | | | 180 | | | | | 185 | | | | | 190 | | | |

| ccc | gcc | ctg | ctc | tcg | gcg | cta | cag | ctt | ttc | aca | ttc | ggc | acc | tgg | ctg | 624 |
|---|---|---|---|---|---|---|---|---|---|---|---|---|---|---|---|---|
| Pro | Ala | Leu | Leu | Ser | Ala | Leu | Gln | Leu | Phe | Thr | Phe | Gly | Thr | Trp | Leu | |
| | | | 195 | | | | | 200 | | | | | 205 | | | |

| cct | cat | agg | cac | acc | gac | gac | gcc | ttc | ccc | gac | aac | cac | aac | gcc | cgc | 672 |
|---|---|---|---|---|---|---|---|---|---|---|---|---|---|---|---|---|
| Pro | His | Arg | His | Thr | Asp | Asp | Ala | Phe | Pro | Asp | Asn | His | Asn | Ala | Arg | |
| | 210 | | | | | 215 | | | | | 220 | | | | | |

| acc | agc | ccc | ttc | ggc | ccg | gtc | ctg | tcg | ttg | ctc | acc | tgc | ttc | cac | ttc | 720 |
|---|---|---|---|---|---|---|---|---|---|---|---|---|---|---|---|---|
| Thr | Ser | Pro | Phe | Gly | Pro | Val | Leu | Ser | Leu | Leu | Thr | Cys | Phe | His | Phe | |
| 225 | | | | | 230 | | | | | 235 | | | | | 240 | |

| ggc | cgc | cac | cac | gaa | cac | cac | ctg | acc | ccc | tgg | aag | ccc | tgg | tgg | agt | 768 |
|---|---|---|---|---|---|---|---|---|---|---|---|---|---|---|---|---|
| Gly | Arg | His | His | Glu | His | His | Leu | Thr | Pro | Trp | Lys | Pro | Trp | Trp | Ser | |
| | | | | 245 | | | | | 250 | | | | | 255 | | |

| ttg | ttc | agc | tag | | | | | | | | | | | | | 780 |
|---|---|---|---|---|---|---|---|---|---|---|---|---|---|---|---|---|
| Leu | Phe | Ser | | | | | | | | | | | | | | |

<210> SEQ ID NO 4
<211> LENGTH: 259
<212> TYPE: PRT
<213> ORGANISM: Brevundimonas vesicularis DC263

<400> SEQUENCE: 4

```
Met Arg Gln Ala Asn Arg Met Leu Thr Gly Pro Arg Cys Ala Lys Cys
1               5                   10                  15
Arg Ala Met Ser Ala Val Thr Pro Met Ser Arg Val Val Pro Asn Gln
            20                  25                  30
Ala Leu Ile Gly Leu Thr Leu Ala Gly Leu Ile Ala Ala Ala Trp Leu
        35                  40                  45
Thr Leu His Ile Tyr Gly Val Tyr Phe His Arg Trp Thr Ile Trp Ser
    50                  55                  60
Val Leu Thr Val Pro Leu Ile Val Ala Gly Gln Thr Trp Leu Ser Val
65                  70                  75                  80
Gly Leu Phe Ile Val Ala His Asp Ala Met His Gly Ser Leu Ala Pro
                85                  90                  95
Ala Arg Pro Arg Leu Asn Thr Ala Ile Gly Ser Leu Ala Leu Ala Leu
            100                 105                 110
Tyr Ala Gly Phe Arg Phe Thr Pro Leu Lys Thr Ala His His Ala His
        115                 120                 125
His Ala Ala Pro Gly Thr Ala Asp Asp Pro Asp Phe His Ala Asp Ala
    130                 135                 140
Pro Arg Ala Phe Leu Pro Trp Phe Tyr Gly Phe Phe Arg Thr Tyr Phe
145                 150                 155                 160
Gly Trp Arg Glu Leu Ala Val Leu Thr Val Leu Val Ala Val Ala Val
                165                 170                 175
Leu Ile Leu Gly Ala Arg Met Pro Asn Leu Leu Val Phe Trp Ala Ala
            180                 185                 190
Pro Ala Leu Leu Ser Ala Leu Gln Leu Phe Thr Phe Gly Thr Trp Leu
        195                 200                 205
Pro His Arg His Thr Asp Asp Ala Phe Pro Asp Asn His Asn Ala Arg
    210                 215                 220
Thr Ser Pro Phe Gly Pro Val Leu Ser Leu Leu Thr Cys Phe His Phe
225                 230                 235                 240
Gly Arg His His Glu His His Leu Thr Pro Trp Lys Pro Trp Trp Ser
                245                 250                 255
Leu Phe Ser
```

<210> SEQ ID NO 5
<211> LENGTH: 771
<212> TYPE: DNA
<213> ORGANISM: Flavobacterium sp. K1-202C

<400> SEQUENCE: 5

```
gtggctgatg gaggaagtga aggaaaggat tctgactttt tgagaaaaca ttcccaactt     60
gctgaaatga aggcggaaat cacatccatg tctgttgatc ctaaaggaat ctttattgct    120
gtggcgataa taggtttgtg gttttccagt ttggtttttc ttctgaacta tgagatttct    180
tggagtgatc cgctagttta tttaggtatc ttggttcaga tgcatcttta taccggactt    240
ttcatcaccg cgcatgatgc tatgcatggt ttagtagctt ccaacaaaag attgaacact    300
agcattggtt gggtttcggc attgctattt tcttacaatt tttatagtaa gctattccca    360
aagcatcacg aacatcaccg gtttgtagcc actgaccaag acccggattt ccatacttca    420
gataattttc tcgtatggta ttttagcttt atcaagcaat acattaccct ctggcaaatc    480
attcttatgg cgatcacttt taatgtactt aagctttttc tgcctgtgga taacttgatt    540
```

-continued

```
attttctgga tgcttccggc agttttatcc acatttcagc ttttttactt tggtacatat    600
ctgcctcata agggtgtaaa cgacaataag caccattcta ctacccagtc aaaaaaccat    660
ttttcggctt ttattacctg ttatttcttc ggttatcact atgagcatca tgattctccg    720
ggtacaccct ggtggaggct ttggagggta aaagaatctc aatcaaacta a             771
```

<210> SEQ ID NO 6
<211> LENGTH: 256
<212> TYPE: PRT
<213> ORGANISM: Flavobacterium sp. K1-202C

<400> SEQUENCE: 6

```
Met Ala Asp Gly Gly Ser Glu Gly Lys Asp Ser Asp Phe Leu Arg Lys
1               5                   10                  15

His Ser Gln Leu Ala Glu Met Lys Ala Glu Ile Thr Ser Met Ser Val
            20                  25                  30

Asp Pro Lys Gly Ile Phe Ile Ala Val Ala Ile Gly Leu Trp Phe
        35                  40                  45

Ser Ser Leu Val Phe Leu Leu Asn Tyr Glu Ile Ser Trp Ser Asp Pro
    50                  55                  60

Leu Val Tyr Leu Gly Ile Leu Val Gln Met His Leu Tyr Thr Gly Leu
65                  70                  75                  80

Phe Ile Thr Ala His Asp Ala Met His Gly Leu Val Ala Ser Asn Lys
                85                  90                  95

Arg Leu Asn Thr Ser Ile Gly Trp Val Ser Ala Leu Leu Phe Ser Tyr
            100                 105                 110

Asn Phe Tyr Ser Lys Leu Phe Pro Lys His His Glu His His Arg Phe
        115                 120                 125

Val Ala Thr Asp Gln Asp Pro Asp Phe His Thr Ser Asp Asn Phe Phe
    130                 135                 140

Val Trp Tyr Phe Ser Phe Ile Lys Gln Tyr Ile Thr Leu Trp Gln Ile
145                 150                 155                 160

Ile Leu Met Ala Ile Thr Phe Asn Val Leu Lys Leu Phe Leu Pro Val
                165                 170                 175

Asp Asn Leu Ile Ile Phe Trp Met Leu Pro Ala Val Leu Ser Thr Phe
            180                 185                 190

Gln Leu Phe Tyr Phe Gly Thr Tyr Leu Pro His Lys Gly Val Asn Asp
        195                 200                 205

Asn Lys His His Ser Thr Thr Gln Ser Lys Asn His Phe Ser Ala Phe
    210                 215                 220

Ile Thr Cys Tyr Phe Phe Gly Tyr His Tyr Glu His His Asp Ser Pro
225                 230                 235                 240

Gly Thr Pro Trp Trp Arg Leu Trp Arg Val Lys Glu Ser Gln Ser Asn
                245                 250                 255
```

<210> SEQ ID NO 7
<211> LENGTH: 19
<212> TYPE: DNA
<213> ORGANISM: Artificial sequence
<220> FEATURE:
<223> OTHER INFORMATION: Primer HK12

<400> SEQUENCE: 7

```
gagtttgatc ctggctcag                                                  19
```

<210> SEQ ID NO 8
<211> LENGTH: 15

<212> TYPE: DNA
<213> ORGANISM: Artificial sequence
<220> FEATURE:
<223> OTHER INFORMATION: Primer JCR14

<400> SEQUENCE: 8
acgggcggtg tgtac                                                        15

<210> SEQ ID NO 9
<211> LENGTH: 16
<212> TYPE: DNA
<213> ORGANISM: Artificial sequence
<220> FEATURE:
<223> OTHER INFORMATION: Primer JCR15

<400> SEQUENCE: 9
gccagcagcc gcggta                                                       16

<210> SEQ ID NO 10
<211> LENGTH: 1291
<212> TYPE: DNA
<213> ORGANISM: Sphingomonas melonis DC18

<400> SEQUENCE: 10
acgctggcgg catgcctaac acatgcaagt cgaacgagat cttcgggtct agtggcgcac        60
gggtgcgtaa cgcgtgggaa tctgccccett ggttcggaat aaccgttgga aacgacggct      120
aataccggat gacgacgtaa gtccaaagat ttatcgccga gggatgagcc cgcgtaggat       180
tagctagttg gtgtggtaaa ggcgcaccaa ggcgacgatc cttagctggt ctgagaggat       240
gatcagccac actgggactg agacacggcc cagactccta cgggaggcag cagtggggaa       300
tattggacaa tgggcgcaag cctgatccag caatgccgcg tgagtgatga aggccttagg       360
gttgtaaagc tcttttaccc gggatgataa tgacagtacc gggagaataa gctccggcta       420
actccgtgcc agcagccgcg gtaatacgga gggagctagc gttgttcgga attactgggc       480
gtaaagcgca cgtaggcggc tttgtaagtt agaggtgaaa gcctgagct caactccaga       540
attgccttta agactgcatc gcttgaatcc aggagaggtg agtggaattc cgagtgtaga       600
ggtgaaattc gtagatattc ggaagaacac cagtggcgaa ggcggctcac tggactggta       660
ttgacgctga ggtgcgaaag cgtggggagc aaacaggatt agatacctg gtagtccacg       720
ccgtaaacga tgataactag ctgtccgggg acttggtctt gggtggcgc agctaacgca       780
ttaagttatc cgcctgggga gtacggccgc aaggttaaaa ctcaaatgaa ttgacggggg       840
cctgcacaag cggtggagca tgtggtttaa ttcgaagcaa cgcgcagaac cttaccagcg       900
tttgacatgt ccggacgatt tccagagatg gatctctttc cttcgggaac tggaacacag       960
gtgctgcatg gctgtcgtca gctcgtgtcg tgagatgttg ggttaagtcc cgcaacgagc     1020
gcaaccctcg cctttagtta ccatcattca gttggggact ctaaaggaac cgccggtgat     1080
aagccggagg aaggtgggga tgacgtcaag tcctcatggc ccttacgcgc tgggctacac     1140
acgtgctaca atggcggtga cagtgggcag caagcacgcg agtgtgcgct aatctccaaa     1200
agccgtctca gttcggattg cactctgcaa ctcgagtgca tgaaggcgga atcgctagta     1260
atcgcggatc agcatgccgc ggtgaatacg t                                    1291

<210> SEQ ID NO 11
<211> LENGTH: 1268
<212> TYPE: DNA
<213> ORGANISM: Brevundimonas vesicularis DC263

<400> SEQUENCE: 11

```
acgctggcgg caggcctaac acatgcaagt cgaacgaact cttcggagtt agtggcggac    60
gggtgagtaa cacgtgggaa cgtgccttta ggttcggaat aactcaggga aacttgtgct   120
aataccgaat gtgcccttcg ggggaaagat ttatcgcctt tagagcggcc cgcgtctgat   180
tagctagttg gtgaggtaaa ggctcaccaa ggcgacgatc agtagctggt ctgagaggat   240
gatcagccac attgggactg agacacggcc caaactccta cgggaggcag cagtggggaa   300
tcttgcgcaa tgggcgaaag cctgacgcag ccatgccgcg tgaatgatga aggtcttagg   360
attgtaaaat tctttcaccg gggacgataa tgacggtacc cggagaagaa gccccggcta   420
acttcgtgcc agcagccgcg gtaatacgaa ggggctagc gttgctcgga attactgggc   480
gtaaagggag cgtaggcgga catttaagtc agggtgaaa tcccgggct caacctcgga   540
attgcctttg atactgggtg tcttgagtat gagagaggtg tgtggaactc cgagtgtaga   600
ggtgaaattc gtagatattc ggaagaacac cagtggcgaa ggcgacacac tggctcatta   660
ctgacgctga ggctcgaaag cgtggggagc aaacaggatt agataccctg gtagtccacg   720
ccgtaaacga tgattgctag ttgtcgggat gcatgcattt cggtgacgca gctaacgcat   780
taagcaatcc gcctggggag tacggtcgca agattaaaac tcaaaggaat tgacggggc   840
ccgcacaagc ggtggagcat gtggtttaat tcgaagcaac gcgcagaacc ttaccacctt   900
ttgacatgcc tggaccgcca cggagacgtg gctttccctt cggggactag acacaggtg    960
ctgcatggct gtcgtcagct cgtgtcgtga tgttgggt taagtcccgc aacgagcgca   1020
accctcgcca ttagttgcca tcatttagtt gggaactcta atgggactgc cggtgctaag   1080
ccggaggaag gtggggatga cgtcaagtcc tcatggccct tacagggtgg gctacacacg   1140
tgctacaatg gcgactacag agggttaatc cttaaaagtc gtctcagttc ggattgtcct   1200
ctgcaactcg agggcatgaa gttggaatcg ctagtaatcg cggatcagca tgccgcgggt   1260
gaatacgt                                                           1268
```

<210> SEQ ID NO 12
<211> LENGTH: 8814
<212> TYPE: DNA
<213> ORGANISM: Pantoea agglomerans DC404

<400> SEQUENCE: 12

```
accgcgaaga cagcaacgtg ctggagaccc gctttgagac ggaaccgggt cggtgctgat    60
caccgagtcg ctgaacagca cgcttgctgg ccggctgccg tggagcgaac tggcccgccg   120
catcgacggt attgagggcc acgtgacgct gaacgtcagc ctgcgtttcg gtaccgctgc   180
cgagacgcgc tccccgtgga gggcgaacac ctttaagggc gatgtgtttc acattgccga   240
tctgatggcg atgctgcgca ccagcgaaga cattgagatt acccactgcg acgatgaaaa   300
aattaccgcc cagctgatga cctcaccggg gtcgcgctcg ctggtcgccc tgctggtcac   360
cgagaaagag ccgctggcgg tgccggatct ctccgccatc gatgaccgca tcgaaaccag   420
ccaccttgcc tggtgcgact ggaccgcag cctcagctac cgcggtctct acgacaagca   480
cgtcaaacga tccgcgctgg cgctgaagtt tctctggtac tccccgaccg gcgcgctggc   540
ggcggcggcc accactcgc tgccggaagg cattggcggg gagaaaaact acgactaccg   600
ctatgcctgg gtgcgcgatg cctgtctgat catcaaagcg ttcgtgttcc tcggtgcgct   660
ggaggactga aaagccgcct tctcctggct gtcgaaaacc attattcgcc acgggcctga   720
gctgcgcgcc tgctatacgc tcgaaggtga cgaggtgccg gccgagtact atccgccgct   780
```

-continued

| | |
|---|---|
| gcgcggatat cgggattccc gcccggtgcg ggtgggcaac aacgcccgca accagatcca | 840 |
| gctcagcatg tacggcgaca tgctcgccac cgcgcagctg tttatcgagg cgggacacgt | 900 |
| actggatctc gccacctcgc gcctgcttgg cgaactggcg aactgctgcg ccgacagctg | 960 |
| gcggcagaag gactccggca tctgggagtt accggacgag cagcactata cccactcgaa | 1020 |
| gatggcctgc tggctggcac tggatcgcgc cgtggcgatg cagaacaga agcacatcga | 1080 |
| accgacctgg gtcgggcgct ggcagcgcga gcgcgatcgg atccgcgact ggatcgaaac | 1140 |
| ccactgctgg tcgagaaaaa agcaggccta cgtgttttac gtcggggacg acgagcggct | 1200 |
| ggatgccgcg ctggcgctgg tgcacgacta cggcaacagc gtaaacccgc agcgtatgct | 1260 |
| ggccacctat cgcgccatca aagcggagct gggacacgac acgcccatgc tctaccgcta | 1320 |
| cagcgaggtg gaaaaggaag aaagcacctt tgtcgcctgc tcgttctggc tggtggaagc | 1380 |
| cctcgccgcg atgggtgaaa ccgacgaggc ccaggcggcc atgaccggca tcctcgagag | 1440 |
| gctctgcgac cggggcaatg ttgaaacttt taacgagatg tttgatgtgc gtaccgacga | 1500 |
| gtggcgcggc aaccttcctc aggggctgag ccatctggcg ctgatctgcg ccgcgcaggc | 1560 |
| gctttcggaa aaatgccgca acacgcgcga ctgacgcacg cgtagctaag gagaagacga | 1620 |
| tgaccatcag aggtatcgaa catattggta ttaccgtcgc cgacctcacc ggggcggagc | 1680 |
| ggtttttcat cgaggcgctg gatgccagcg tgctctaccg catcgtgccg cccggcgcgg | 1740 |
| cggacaatgc catcagcggc gaccagatga cgcggctcaa tggctttccc ccggagatgc | 1800 |
| gggttaccgg cctggccatg ctgcgtctcg gcaacggctg caatattgag ctgtttgaga | 1860 |
| tcgatcccgg cgtggcagac gcgcccggaa atatcagcca ggcgggcctg aaccacctgt | 1920 |
| cggtttacgt ggacgacatt cagcaggccg gcgcacgggt aaaagcacag ggcgccacgc | 1980 |
| tgtttgacgg gccgagcgac tgctttgctc aggaagaggg ccgcggcaac cagacctggt | 2040 |
| tctgccgcac gccttttggc ctgctgattg aactcatctc ccttccctcg ccgcttcgct | 2100 |
| acgatgcgca ggcgcagcaa acccgctgga tcccccagcg ctgacaggcc tctctcacgc | 2160 |
| gggcatcgcc cgcgttgtca taccctcgtc accgtcctga caaaaattaa caataaattt | 2220 |
| tcattttca gccagacttt aagcacatag cgtcgccatg acatttattt tcatctaaac | 2280 |
| ctatacaaga aaacattga tgtataactt tgcataccgc tgcacacagg ctcagactgc | 2340 |
| gacacccgtt gcgggtcagc gctatttcca tttcatctgc gagacgccgg gtaccaacca | 2400 |
| tgacaagacc cttgaaaca catcccggtc acgacgggga actgcatgag ctgcacgctg | 2460 |
| ccctgcaacg tcgcctggat gaactgctgc ccgttggcga tgagcgggat cgggtcagca | 2520 |
| gcgcaatgcg cgaaggcgta ctggcaccgg ggaaacgcat tcgcccgctg ctcctgatcc | 2580 |
| tcgccgcccg cgacctcggc tgcgatcgcg accacccccgg cctgctggat atggcctgtg | 2640 |
| cggtggaaat ggtgcacgcc tcgtcgctga tcctcgacga tattccctgc atggataacg | 2700 |
| cggcgctccg gcgcggtcgc cctaccattc atcgccagta tggtgaagac gtggcaattc | 2760 |
| tcgctgcggt agcgttgctc agcagcgcct ttggcgtgat ggtcgcggcg cagggattgt | 2820 |
| ctcccgagtg ccgcagccag gcggtggcgg agctgtcgat ggcggtcggt acccagggtc | 2880 |
| tggtgcaggg tcagtataag gatctgcgtg aaggcaccgc cccgcgcagc gccgaggaga | 2940 |
| tcgccaccac caacgaactg aaaaccagcg tgctgtttgg tgccacgctg caaatcgcgg | 3000 |
| ccctggcggc aggcgcctcg ccggcggcgc gccagaaaat gcgctgcttt gcgcaggatt | 3060 |
| taggccaggc gttccagctg ctggacgatc tggcggacgg ccatgccggg accggcaaag | 3120 |

-continued

```
acatcaataa ggacgcgggt aagtccacgc tggtggcgat gctcggcagc gacgcggtgc     3180
gcgagcggct cgacacccat ctgcgccgcg cagacgccca tttttcacgc gcctgcggaa     3240
aaaaccaggc cacgcgacgc tttatgcacg cctggttttc aaaacagctg gccgcgttta     3300
gctgagcaac ggatacaccc cggtaatatt tgtggagatc acatgaagga cgcgcatctg     3360
gttcagcgta aaaatgacca cctggatatc gtgctgcacc ctgaccgggc gatgagtacc     3420
attcgcaccg gatttgacgc ctggcgtttt gaacactgcg ccctcccgga gctggatctc     3480
gacggtatcg atctctccac caccctgttt tcccgcccgc tgaaagcccc ggtgctgatc     3540
agctccatga ccggcggcgc ggcgcgcgcc agagacatta accgtcatct ggcccaggcg     3600
gcgcaaaccc ttgggctggc gatgggcgtc ggttcccagc gcgtggcgct ggaggacggc     3660
gcgcagcacg ggctggatgc ccagctacgc catatcgccc cggacgtgcc gctgctggct     3720
aaccttggcg cggcgcagat ccgcggtgcg caggggctgg actacgcccg gcgcgcggtg     3780
gacatgatcg acgccgacgc gttaattgtg catctgaacc cgctgcagga ggcgctccag     3840
ggcggcggcg atcgcgactg gcgcggcatc ctcaacgcca ttgcgcagct ggtgcgcgac     3900
ctgccggtac cggtggtggt taaagaggtg gcgccgggga tctccccgga cgttgcctgc     3960
cgactggcgg acgtcggcgt ggcgatgatc gacattgccg gcgcgggcgg aaccagctgg     4020
gcggcggtgg aagctgaacg cgccccgacc cccgaggcgc gaaatgtggc gatggccttt     4080
gccgactggg gcattcctac tgccgatgcg ctgcgtcgcg tccatcttgc gctgcctgat     4140
atcccgctta tcgcctccgg cggcatcgcc aacggcattg acgcagcaaa agccatcgcg     4200
ctgggtgcag atctggtggg ccaggccgcg gcggtgctgg cgcatgccaa cgcctccggc     4260
gacgcggcaa ttgcccattt ccgcaccctg attacgcagc tgcggatcgc ctgtttctgt     4320
accggcagtg caaacctgca ggcgttgcga cacgccacgc tgcttccggt caacggcggc     4380
gcatccctgt gacgcagtac ggtgccttat accggggagc ggtatgaaaa aatgggatct     4440
gattctggtc ggcgcggggc tggccaacgg gcttatcgcc tggcgactaa agcagcgtca     4500
tccgacgctt gctgtattaa tgctggagtg cggcgacgcg cccggcggaa accacacctg     4560
gtcctttcac caacacgata tcacgccagc ccagcacgcc tggctggcgc cgctggtggc     4620
ccatcgctgg gacgggtacg acgtccactt tccgaacgtg tcgcgcaccc tgcatgacgg     4680
ctacctgacc atcacctcca cgcgttttgc ccaagcgatg cgcgggctga tgaaagagaa     4740
tttgctgaca aacgtgaccg tgtcacgggt gagcgggcag gaagtaaccc tcagcgacgg     4800
acgacgcttt accgccgggg cggtgattga tggccgcggc tatcagccct cgccgcacct     4860
cagcattggc tatcaggcgt tcatcggcca ggagtggcaa ctgaccgcgc cccacgggtt     4920
aacgcgcccg atcctgatgg atgcccgcgt cgcccagggc aacggctacc gctttgtcta     4980
taccctgccg ctcagcgccg acaccctgct tatcgaagac acgcactaca ttgacggccc     5040
gacgctcgac gccgattcag cccgcgcgcg gattgccgat tacgcccgcc agcagggctg     5100
gcagcttgcg cggctggtgc gtgaggaaca gggggcgctg ccgatcaccc tgtccggcga     5160 tccgccgcc ttctggcacc agttccatca tcagccggtc agcggcctgc gcgccggtct     5220
gttccatgcc accaccggct attcgctgcc gctggcggtt cggctggcgg accgcattgc     5280
caacgcgccg ggactgcatc agggcgcgct ctatcagctg atcgccgatt tcgcggcgcg     5340
ccactggcag acacaacgct ttttccgcct gcttaaccgc atgcttttcc tggccggcac     5400
acccgaccag cgctgcgcg tgatgcagcg gttttaccag cttgacgagc agctgatcgc     5460 ccgttttat gccggccagc ttcgctccgc cgaccgcgcg cgcctgctgc ttggcaaacc     5520
```

```
gccggtgccg attgtcgggg cgatcaaagc cctgctccac actcattctt ctctgcgagc   5580
ccatcataaa tgaaacaaac cattgtaatt ggcgccgggt tcggcggact ggcgctggcg   5640
attcgcctcc aggcggcggg cattcctacc acgctgctgg agagccgcga caaacccggc   5700
ggccgcgcct atgtctacga agatcgcggc tttacctttg atgcgggtcc caccgtcatc   5760
accgatccct ccgccattga ggagctgttc accctcgccg aaaacggct gaaggactac    5820
gttgagctga tgccggtgac gccgttctat cgcctgtgct gggaagacgg caaggttttc   5880
gactacgcca acgatcaggc ggcgcttgag tcgcagatcg ccgcgtttaa cccgaacgac   5940
gtggcgggct atcaccgctt cctcgactac tcccggcgg tgtttgccga aggctatctg    6000
aagctcggcg cggtgccgtt tctctcgttt cgcgacatgc tgcgcgccgg tcctcaactg   6060
gcgcggctgc aggcatggcg cagcgtgtac gacaaagtgt cggcctacgt ggaagacgag   6120
cacctgcggc aggcatttc gtttcactcg ctgctggtgg gcggcaaccc gttctccacg    6180
tcttctattt acaccctgat ccacgccctg gagcgggaat ggggcgtctg gttcccgcgc   6240
ggcggcaccg gtgcgctggt tcagggcatg gtgaagctgt tcaggatct tggcggcacc    6300
ctcacccta acgctcaggt tgagcggctg gagacggtgg acaatcaggt gaaggccgtg    6360
catctggtta acgggcagcg gctggaggct gcggcggtgg cctcgaacgc ggacgtggta   6420
aatacctatg cccgactgct cggccatcac ccgcacggcg ccgctacggc caaaaagctg   6480
aaacgcaagc gcatgagcaa ctcgctgttc gtgctctatt ttggcctgga tcaccatcac   6540
acccagctgg cgcaccatac cgtctgcttt ggcccgcgtt ataaagcgct aatcgatgaa   6600
attttcagcg ccgacaccct gtcggaagat ttttcgctct atctgcatgc gccctgcgta   6660
accgacccgt cgctggcccc gccggggtgc ggcagctact atgtgctcgc gccggtgccg   6720
cacctcggta acgccccgct cgactggagc gtggaagggc gcgtctgcg ggatcgcatt    6780
tttgattatc tcgaagcgcg ctatatgccg gggctgcgct cccagctggt gacgcaccgc   6840
atgttcacgc cggaagattt tcgcgatacg ctcgatgcct ggcagggggtc agcgttttca   6900
ctggagccga tcctcaccca gagcgcctgg ttccggccgc acaaccgcga cagcgtggtt   6960
gataacctct acctggtcgg cgccggaacg catcccggcg ctggcgtgcc gggcgtgatc   7020
ggatccgcca aggcaacggc ccagttaatg ttaaaggatt tagcgtaatg tcccagccgc   7080
ttctcgaaca cgccagcgcc accatgaccg ccggttctaa aagtttcgcc accgcctcaa   7140
agctgtttga caaacgcacc cggcgcagcg cgctgatgct ctatacctgg tgccgctact   7200
gcgacgatgt tatcgacgga caggtggtgg gttttgctgc cccgaccgag cagagcgaca   7260
cgcccgaggc gcgcctgcaa cggctgcgta agatgacgcg ccgcgcctac gacggggaaa   7320
ccatgcaaga gccgccgttc gccgccttc aggaggttgc cctcgcccat gccattccgc    7380
ctactcaggc cttcgaccac ctggaaggct atgcgatgga cgtgcgcaac gagcgctatt   7440
acagcctcga tgatacgctc cgctactgtt atcacgtggc gggcgtggtc ggcctgatga   7500
tggccagggt gatgggagtg cgggacgaag ccacgctgga tcgcgcctgc gatctgggca   7560
ttgcctttca gctcaccaat atcgccaggg atatcgttga cgatgcgcag gtgggacgct   7620
gctacctgcc gcagcagtgg ctggcggaag tcggactcaa tgaacagacc tgcaccgtgc   7680
gggccaaccg tccggcgctg gcgcgtctgg cagcgcggct ggtgaccgag ctgagccct    7740
attatcagtc agcgcttgcc gggctggggg atctgcccct gcgctccgcc tgggcgattg   7800
ccaccgcgca cggggtgtat cgtgagatcg gggtgaaggt gctgatggcg ggtgaaaaag   7860
```

```
catgggatac cgccagggc acgacgcgcg cggagaagct ggcgctggtt atttccggcg      7920
cgaagcaggc gatggcttcc cggaaggcga gctggccgcc gcgcgatccg cacctctggc      7980
agcgcccgcg ctagcgggtc tgccgttacg ttcgcgcagc accgcctgca gcttgtccac      8040
cggtggggcg tagataaacc cgaaggagac gcacccttcg cgccccgca ccgcgtgatg      8100 cagccggtgt gccatgtaga ggcggcgcag atagccgcgg cgcggcacgt aacggaacgg      8160
ccagcgctgg tggactaaac catcgtgaac gataaagtag atcacgccgt agccggtcat      8220
tcccgcgcca atccactgaa gcggccagta cccttcgctg cccgcgtaaa tcagcgcaat      8280
ggccagtagc gcaaacacca ccgcatagag atcgttacgc tcaaacgccc ctttgcgcgg      8340
ggtatggtgc gaatgatgcc agccccatcc ccagccgtgc atgatgtact tgtgtgcgaa      8400
cgttgccacc ccttccatga tgatgatagt cagtagcacg atcccggtat ccacaacgc      8460 aagcataggt ttttcctgta gttgacagcc ctaaagcgt agcctggaat gccaggaaac      8520
ataagcgtaa cctcggggat aatgcgcttt tcaggcgtaa aagcatttat gacaattatt      8580
catcgcgcca cgttcacgcc gtgacgccct gctcaccgcg cggcagcagc cgcatcggct      8640
gataaacgcg cccggtttct gcgcgtcatc gcccggtgtg cgcggcgtca acgcaataaa      8700
acttactttc aaaaggcggc ccgaaaaggc tacccttttt tattcttgtc atatactcga      8760
tctaacctga attatcgccg taacgtaccg cttcttttga ggtaatcccg gagc            8814

<210> SEQ ID NO 13
<211> LENGTH: 34
<212> TYPE: DNA
<213> ORGANISM: Artificial sequence
<220> FEATURE:
<223> OTHER INFORMATION: Primer pWEB404F

<400> SEQUENCE: 13
gaattcacta gtcgagacgc cgggtaccaa ccat                                  34

<210> SEQ ID NO 14
<211> LENGTH: 25
<212> TYPE: DNA
<213> ORGANISM: Artificial sequence
<220> FEATURE:
<223> OTHER INFORMATION: Primer pWEB404R

<400> SEQUENCE: 14
gaattctagc gcgggcgctg ccaga                                            25

<210> SEQ ID NO 15
<211> LENGTH: 5632
<212> TYPE: DNA
<213> ORGANISM: Pantoea agglomerans DC404

<400> SEQUENCE: 15
catgaccggc ggcgcggcgc gcgccagaga cattaaccgt catctggccc aggcggcgca       60
aacccttggg ctggcgatgg gcgtcggttc ccagcgcgtg gcgctggagg acggcgcgca      120
gcacgggctg gatgcccagc tacgccatat cgccccggac gtgccgctgc tggctaacct      180
tggcgcggcg cagatccgcg gtgcgcaggg gctggactac gcccggcgcg cggtggacat      240
gatcgacgcc gacgcgttaa ttgtgcatct gaacccgctg caggaggcgc tccagggcgg      300
cggcgatcgc gactggcgcg gcatcctcaa cgccattgcg cagctggtgc gcgacctgcc      360
ggtaccggtg gtggttaaag aggtgggcgc cgggatctcc ccggacgttg cctgccgact      420
ggcggacgtc ggcgtggcga tgatcgacat tgccggcgcg ggcggaacca gctgggcggc      480
```

-continued

```
ggtggaagct gaacgcgccc cgaccccga ggcgcgaaat gtggcgatgg cctttgccga      540
ctggggcatt cctactgccg atgcgctgcg tcgcgtccat cttgcgctgc ctgatatccc      600
gcttatcgcc tccggcggca tcgccaacga cattgacgca gcaaaagcca tcgcgctggg      660
tgcagatctg gtgggccagg ccgcggcggt gctggcgcat gccaacgcct ccggcgacgc      720
ggcaattgcc catttccgca ccctgattac gcagctgcgg atcgcctgtt tctgtaccgg      780
cagtgcaaac ctgcaggcgt tgcgacacgc cacgctgctt ccggtcaacg gcggcgcatc      840
cctgtgacga gtacggtgc cttataccgg ggagcggtat gaaaaaatgg gatctgattc      900
tggtcggcgc ggggctggcc aacgggctta tcgcctggcg actaaagcag cgtcatccga      960
cgcttgctgt attaatgctg gagtgcgcg acgcgcccgg cggaaaccac acctggtcct     1020
ttcaccaaca cgatatcacg ccagcccagc acgcctggct ggcgccgctg gtggcccatc     1080
gctgggacgg gtacgacgtc cactttccga acgtgtcgcg caccctgcat gacggctacc     1140
tgaccatcac ctccacgcgt tttgcccaag cgatgcgcgg gctgatgaaa gagaatttgc     1200
tgacaaacgt gaccgtgtca cgggtgagcg ggcaggaagt aaccctcagc gacggacgac     1260
gctttaccgc cggggcggtg attgatggcc gcggctatca gccctcgccg cacctcagca     1320
ttggctatca ggcgttcatc ggccaggagt ggcaactgac cgcgccccac gggttaacgc     1380
gcccgatcct gatggatgcc cgcgtcgccc agggcaacgg ctaccgcttt gtctataccc     1440
tgccgctcag cgccgacacc ctgcttatcg aagacacgca ctacattgac ggcccgacgc     1500
tcgacgccga ttcagcccgc gcgcggattg ccgattacgc ccgccagcag ggctggcagc     1560
ttgcgcggct ggtgcgtgag gaacagggg cgctgccgat caccctgtcc ggcgatccgg     1620
ccgccttctg gcaccagttc catcatcagc cggtcagcgg cctgcgcgcc ggtctgttcc     1680
atgccaccac cggctattcg ctgccgctgg cggttcggct ggcggaccgc attgccaacg     1740
cgccgggact gcatcaggc gcgctctatc agctgatcgc cgatttcgcg gcgcgccact     1800
ggcagacaca acgcttttc cgcctgctta accgcatgct tttcctggcc ggcacacccg     1860
accagcgctg gcgcgtgatg cagcggtttt accagcttga cgagcagctg atcgcccgtt     1920
tttatgccgg ccagcttcgc tccgccgacc gcgcgcgcct gctgcttggc aaaccgccgg     1980
tgccgattgt cggggcgatc aaagccctgc tccacactca ttcttctctg cgagcccatc     2040
ataaatgaaa caaaccattg taattggcgc cgggttcggc ggactggcgc tggcgattcg     2100
cctccaggcg gcgggcattc ctaccacgct gctggagagc cgcgacaaac ccggcggccg     2160
cgcctatgtc tacgaagatc gcggctttac ctttgatgcg ggtcccaccg tcatcaccga     2220
tccctccgcc attgaggagc tgttcaccct cgccggaaaa cggctgaagg actacgttga     2280
gctgatgccg gtgacgccgt tctatcgcct gtgctgggaa gacggcaagg ttttcgacta     2340
cgccaacgat caggcggcgc ttgagtcgca gatcgccgcg tttaacccga acgacgtggc     2400
gggctatcac cgcttcctcg actactcccg ggcggtgttt gccgaaggct atctgaagct     2460
cggcgcggtg ccgtttctct cgtttcgcga catgctgcgc gccggtcctc aactggcgcg     2520
gctgcaggca tggcgcagcg tgtacgacaa agtgtcggcc tacgtggaag acgagcacct     2580
gcggcaggca ttttcgtttc actcgctgct ggtgggcggc aacccgttct ccacgtcttc     2640
tatttacacc ctgatccacg ccctggagcg ggaatggggc gtctggttcc cgcgcggcgg     2700
caccggtgcg ctggttcagg gcatggtgaa gctgttcag gatcttggcg gcaccctcac     2760
ccttaacgct caggttgagc ggctggagac ggtggacaat caggtgaagg ccgtgcatct     2820
```

```
ggttaacggg cagcggctgg aggctgcggc ggtggcctcg aacgcggacg tggtaaatac   2880
ctatgcccga ctgctcggcc atcacccgca cggcgccgct acggccaaaa agctgaaacg   2940
caagcgcatg agcaactcgc tgttcgtgct ctattttggc ctggatcacc atcacaccca   3000
gctggcgcac cataccgtct gctttggccc gcgttataaa gcgctaatcg atgaaatttt   3060
cagcgccgac accctgtcgg aagattttc gctctatctg catgcgccct gcgtaaccga   3120
cccgtcgctg gccccgccgg ggtgcggcag ctactatgtg ctcgcgccgg tgccgcacct   3180
cggtaacgcc ccgctcgact ggagcgtgga agggccgcgt ctgcgggatc gcattttga    3240 ttatctcgaa gcgcgctata tgccggggct gcgctcccag ctggtgacgc accgcatgtt   3300
cacgccggaa gattttcgcg atacgctcga tgcctggcag gggtcagcgt tttcactgga   3360
gccgatcctc acccagagcg cctggttccg gccgcacaac cgcgacagcg tggttgataa   3420
cctctacctg gtcggcgccg gaacgcatcc cggcgctggc gtgccgggcg tgatcggatc   3480
cgccaaggca acgcccagt taatgttaaa ggatttagcg taatgtccca gccgcttctc   3540
gaacacgcca gcgccaccat gaccgccggt tctaaaagtt tcgccaccgc ctcaaagctg   3600
tttgacaaac gcaccggcg cagcgcgctg atgctctata cctggtgccg ctactgcgac   3660
gatgttatcg acggacaggt ggtgggtttt gctgccccga ccgagcagag cgacacgccc   3720
gaggcgcgcc tgcaacggct gcgtaagatg acgcgccgcg cctacgacgg ggaaaccatg   3780
caagagccgc cgttcgccgc cttttcaggag gttgccctcg cccatgccat tccgcctact   3840 caggcctttcg accacctgga aggctatgcg atggacgtgc gcaacgagcg ctattacagc   3900
ctcgatgata cgctccgcta ctgttatcac gtggcgggcg tggtcggcct gatgatggcc   3960
agggtgatgg gagtgcggga cgaagccacg ctggatcgcg cctgcgatct gggcattgcc   4020
tttcagctca ccaatatcgc cagggatatc gttgacgatg cgcaggtggg acgctgctac   4080
ctgccgcagc agtggctggc ggaagtcgga ctcaatgaac agacctgcac cgtgcgggcc   4140
aaccgtccgg cgctggcgcg tctggcagcg cggctggtga ccgaggctga gccctattat   4200
cagtcagcgc ttgccgggct gggggatctg ccctgcgct ccgcctgggc gattgccacc    4260
gcgcacgggg tgtatcgtga gatcggggtg aaggtgctga tggcgggtga aaaagcatgg   4320
gatacccgcc agggcacgac gcgcgcggag aagctggcgc tggttatttc cggcgcgaag   4380
caggcgatgg cttcccggaa ggcgagctgg ccgccgcgcg atccgcacct ctggcagcgc   4440
ccgcgctaga attcgaattc actagtcgag acgccgggta ccaaccatga caagacccctt   4500 tgaaacacat cccggtcacg acggggaact gcatgagctg cacgctgccc tgcaacgtcg   4560
cctggatgaa ctgctgcccg ttggcgatga gcgggatcgg gtcagcagcg caatgcgcga   4620
aggcgtactg gcaccgggga aacgcattcg cccgctgctc ctgatcctcg ccgcccgcga   4680
cctcggctgc gatcgcgacc accccggcct gctggatatg gcctgtgcgg tggaaatggt   4740
gcacgcctcg tcgctgatcc tcgacgatat tccctgcatg gataacgcgg cgctccggcg   4800
cggtcgccct accattcatc gccagtatgg tgaagacgtg gcaattctcg ctgcggtagc   4860
gttgctcagc agcgcctttg gcgtgatggt cgcggcgcag ggattgtctc ccgagtgccg   4920
cagccaggcg gtggcggagc tgtcgatggc ggtcggtacc cagggtctgg tgcagggtca   4980
gtataaggat ctgcgtgaag gcaccgcccc gcgcagcgcc gaggagatcg ccaccaccaa   5040
cgaactgaaa accagcgtgc tgtttggtgc cacgctgcaa atcgcggccc tggcggcagg   5100
cgcctcgccg gcggcgcgcc agaaaatgcg ctgctttgcg caggatttag gccaggcgtt   5160
ccagctgctg gacgatctgg cggacggcca tgccgggacc ggcaaagaca tcaataagga   5220
```

```
cgcgggtaag tccacgctgg tggcgatgct cggcagcgac gcggtgcgcg agcggctcga    5280
cacccatctg cgccgcgcag acgcccattt ttcacgcgcc tgcggaaaaa accaggccac    5340
gcgacgcttt atgcacgcct ggttttcaaa acagctggcc gcgtttagct gagcaacgga    5400
tacaccccgg taatatttgt ggagatcaca tgaaggacgc gcatctggtt cagcgtaaaa    5460
atgaccacct ggatatcgtg ctgcaccctg accgggcgat gagtaccatt cgcaccggat    5520 tgacgcctg gcgttttgaa cactgcgccc tcccggagct ggatctcgac ggtatcgatc    5580
tctccaccac cctgttttcc cgcccgctga agccccggt gctgatcagc tc             5632
```

<210> SEQ ID NO 16
<211> LENGTH: 43
<212> TYPE: DNA
<213> ORGANISM: Artificial sequence
<220> FEATURE:
<223> OTHER INFORMATION: Primer crtW-18_F

<400> SEQUENCE: 16
actagtaagg aggaataaac catgaccgtc gatcacgacg cac             43

<210> SEQ ID NO 17
<211> LENGTH: 28
<212> TYPE: DNA
<213> ORGANISM: Artificial sequence
<220> FEATURE:
<223> OTHER INFORMATION: Primer crtW-18_R

<400> SEQUENCE: 17
tctagactac cggtctttgc ttaacgac             28

<210> SEQ ID NO 18
<211> LENGTH: 42
<212> TYPE: DNA
<213> ORGANISM: Artificial sequence
<220> FEATURE:
<223> OTHER INFORMATION: Primer crtW-263_F

<400> SEQUENCE: 18
actagtaagg aggaataaac catgcggcaa gcgaacagga tg             42

<210> SEQ ID NO 19
<211> LENGTH: 28
<212> TYPE: DNA
<213> ORGANISM: Artificial sequence
<220> FEATURE:
<223> OTHER INFORMATION: Primer crtW-263_R

<400> SEQUENCE: 19
tctagactag ctgaacaaac tccaccag             28

<210> SEQ ID NO 20
<211> LENGTH: 44
<212> TYPE: DNA
<213> ORGANISM: Artificial sequence
<220> FEATURE:
<223> OTHER INFORMATION: Primer crtW/K1-202CF

<400> SEQUENCE: 20
actagtaagg aggaataaac catggctgat ggaggaagtg aagg             44

<210> SEQ ID NO 21
<211> LENGTH: 26
<212> TYPE: DNA

<213> ORGANISM: Artificial sequence
<220> FEATURE:
<223> OTHER INFORMATION: Primer crtW/K1-202CR

<400> SEQUENCE: 21

```
tctagattag tttgattgag attctt                                          26
```

<210> SEQ ID NO 22
<211> LENGTH: 489
<212> TYPE: DNA
<213> ORGANISM: Agrobacterium aurantiacum

<400> SEQUENCE: 22

```
atgaccaatt tcctgatcgt cgtcgccacc gtgctggtga tggagttgac ggcctattcc      60
gtccaccgct ggatcatgca cggccccctg gctggggct ggcacaagtc ccaccacgag      120
gaacacgacc acgcgctgga aaagaacgac ctgtacggcc tggtctttgc ggtgatcgcc     180
acggtgctgt tcacggtggg ctggatctgg gcgccggtcc tgtggtggat cgccttgggc     240
atgactgtct atgggctgat ctatttcgtc ctgcatgacg ggctggtgca tcagcgctgg     300
ccgttccgtt atatcccgcg caagggctat gccagacgcc tgtatcaggc ccaccgcctg     360
caccatgcgg tcgaggggcg cgaccattgc gtcagcttcg gcttcatcta tgcgccccg     420
gtcgacaagc tgaagcagga cctgaagatg tcgggcgtgc tgcgggccga ggcgcaggag    480
cgcacgtga                                                            489
```

<210> SEQ ID NO 23
<211> LENGTH: 729
<212> TYPE: DNA
<213> ORGANISM: Agrobacterium aurantiacum

<400> SEQUENCE: 23

```
atgagcgcac atgccctgcc caaggcagat ctgaccgcca ccagcctgat cgtctcgggc      60
ggcatcatcg ccgcttggct ggccctgcat gtgcatgcgc tgtggttct ggacgcagcg     120
gcgcatccca tcctggcgat cgcaaatttc ctggggctga cctggctgtc ggtcggattg     180
ttcatcatcg cgcatgacgc gatgcacggg tcggtggtgc cggggcgtcc gcgcgccaat     240
gcggcgatgg gccagcttgt cctgtggctg tatgccggat tttcgtggcg caagatgatc     300
gtcaagcaca tggcccatca ccgccatgcc ggaaccgacg acgaccccga tttcgaccat     360
ggcggcccgg tccgctggta cgcccgcttc atcggcacct atttcggctg gcgcgagggg     420
ctgctgctgc ccgtcatcgt gacggtctat gcgctgatcc ttggggatcg ctggatgtac     480
gtggtcttct ggccgctgcc gtcgatcctg cgtcgatcc agctgttcgt gttcggcacc     540
tggctgccgc accgccccgg ccacgacgcg ttcccggacc gccacaatgc gcggtcgtcg     600
cggatcagcg accccgtgtc gctgctgacc tgctttcact tggcggttta tcatcacgaa     660
caccacctgc acccgacggt gccgtggtgg cgcctgccca gcacccgcac caaggggac     720
accgcatga                                                            729
```

<210> SEQ ID NO 24
<211> LENGTH: 30
<212> TYPE: DNA
<213> ORGANISM: Artificial sequence
<220> FEATURE:
<223> OTHER INFORMATION: Primer crtZW_F

<400> SEQUENCE: 24

```
actagtaagg aggaataaac catgaccaac                                      30
```

<210> SEQ ID NO 25
<211> LENGTH: 59
<212> TYPE: DNA
<213> ORGANISM: Artificial sequence
<220> FEATURE:
<223> OTHER INFORMATION: Primer crtZW_soe_R

<400> SEQUENCE: 25
agggcatggg cgctcatggt atattcctcc tttctagatt aggtgcgttc ttgggcttc         59

<210> SEQ ID NO 26
<211> LENGTH: 59
<212> TYPE: DNA
<213> ORGANISM: Artificial sequence
<220> FEATURE:
<223> OTHER INFORMATION: Primer crtZW_soe_F

<400> SEQUENCE: 26
gaagcccaag aacgcaccta atctagaaag gaggaatata ccatgagcgc ccatgccct         59

<210> SEQ ID NO 27
<211> LENGTH: 32
<212> TYPE: DNA
<213> ORGANISM: Artificial sequence
<220> FEATURE:
<223> OTHER INFORMATION: Primer crtZW_R

<400> SEQUENCE: 27
gctagctgta catcacgcgg tgtcgccttt gg                                      32

<210> SEQ ID NO 28
<211> LENGTH: 35
<212> TYPE: DNA
<213> ORGANISM: artificial sequence
<220> FEATURE:
<223> OTHER INFORMATION: Primer crt-260_F

<400> SEQUENCE: 28
gaattcacta gtaccaacca tggatagcca ttatg                                   35

<210> SEQ ID NO 29
<211> LENGTH: 51
<212> TYPE: DNA
<213> ORGANISM: artificial sequence
<220> FEATURE:
<223> OTHER INFORMATION: Primer crt-260SOE_R

<400> SEQUENCE: 29
atcaggtcgc ctccgccagc acgactttca gttgaatatc gctagctgtt g                 51

<210> SEQ ID NO 30
<211> LENGTH: 51
<212> TYPE: DNA
<213> ORGANISM: artificial sequence
<220> FEATURE:
<223> OTHER INFORMATION: Primer crt-260SOE_F

<400> SEQUENCE: 30
caacagctag cgatattcaa ctgaaagtcg tgctggcgga ggcgacctga t                 51

<210> SEQ ID NO 31
<211> LENGTH: 49
<212> TYPE: DNA
<213> ORGANISM: artificial sequence
<220> FEATURE:

```
<223> OTHER INFORMATION: Primer crt-260R1_R

<400> SEQUENCE: 31
cattttttct tccctggttc gacagagttc aacagcgcgc gcagcgctt        49

<210> SEQ ID NO 32
<211> LENGTH: 49
<212> TYPE: DNA
<213> ORGANISM: artificial sequence
<220> FEATURE:
<223> OTHER INFORMATION: Primer crt-260R1_F

<400> SEQUENCE: 32
aagcgctgcg cgcgctgttg aactctgtcg aaccagggaa gaaaaaatg         49

<210> SEQ ID NO 33
<211> LENGTH: 26
<212> TYPE: DNA
<213> ORGANISM: artificial sequence
<220> FEATURE:
<223> OTHER INFORMATION: Primer crt-260_R

<400> SEQUENCE: 33
gaattcaacg aggacgctgc cacaga                                  26
```

CAROTENOID KETOLASES

This application claims the benefit of U.S. Provisional Application No. 60/531,310, filed Dec. 19, 2003.

FIELD OF THE INVENTION

This invention is in the field of microbiology and molecular biology. More specifically, this invention pertains to nucleic acid fragments encoding enzymes useful for microbial production of cyclic ketocarotenoid compounds.

BACKGROUND OF THE INVENTION

Carotenoids are pigments that are ubiquitous throughout nature and synthesized by all photosynthetic organisms, and in some heterotrophic growing bacteria and fungi. Carotenoids provide color for flowers, vegetables, insects, fish and birds. Colors of carotenoid range from yellow to red with variations of brown and purple. As precursors of vitamin A, carotenoids are fundamental components in our diet and they play additional important role in human health. Because animals are unable to synthesize carotenoid de novo, they must obtain them by dietary means. Thus, manipulation of carotenoid production and composition in plants or bacteria can provide new or improved source for carotenoids. Industrial uses of carotenoids include pharmaceuticals, food supplements, animal feed additives, and colorants in cosmetics, to mention a few.

Industrially, only a few carotenoids are used for food colors, animal feeds, pharmaceuticals, and cosmetics, despite the existence of more than 600 different carotenoids identified in nature. This is largely due to difficulties in production. Presently, most of the carotenoids used for industrial purposes are produced by chemical synthesis; however, these compounds are very difficult to make chemically (Nelis and Leenheer, *Appl. Bacteriol.*, 70:181-191 (1991)). Natural carotenoids can either be obtained by extraction of plant material or by microbial synthesis; but, only a few plants are widely used for commercial carotenoid production and the productivity of carotenoid synthesis in these plants is relatively low. As a result, carotenoids produced from these plants are very expensive. One way to increase the productive capacity of biosynthesis would be to apply recombinant DNA technology (reviewed in Misawa and Shimada, *J. Biotech.*, 59:169-181 (1998)). Thus, it would be desirable to produce carotenoids in non-carotenogenic bacteria and yeasts, thereby permitting control over quality, quantity, and selection of the most suitable and efficient producer organisms. The latter is especially important for commercial production economics (and therefore availability) to consumers.

Carotenoid ketolases are a class of enzymes that introduce keto groups to the ionone ring of the cyclic carotenoids, such as β-carotene, to produce ketocarotenoids. Examples of ketocarotenoids include astaxanthin, canthaxanthin, adonixanthin, adonirubin, echinenone, 3-hydroxyechinenone, 3'-hydroxyechinenone, 4-keto-gamma-carotene, 4-keto-rubixanthin, 4-keto-torulene, 3-hydroxy-4-keto-torulene, deoxyflexixanthin, and myxobactone. Two classes of ketolase, CrtW and CrtO, have been reported. The two classes have similar functionality yet appear to have arisen independently as they share very little sequence similarity. The CrtW is a symmetrically acting enzyme that adds keto-groups to both rings of β-carotene (Hannibal et al., *J. Bacteriol.*, 182: 3850-3853 (2000)). Fernández-González et al. (*J. of Biol. Chem.*, 272: 9728-9733 (1997)) reported that the CrtO ketolase enzyme from *Synechocystis* sp. PCC6803 adds a keto-group asymmetrically to only one of the two β-ionone rings of β-carotene.

Several examples of CrtW ketolases have been reported in variety of bacteria including *Agrobacterium aurantiacum* (U.S. Pat. No. 6,150,130), *Bradyrhizobium* sp. (U.S. Patent Publication No. 20030087337), and *Brevundimonas aurantiacum* (WO 02/079395). However, there is a need to identify additional novel CrtW ketolase genes useful for genetically engineering industrially suitable microorganisms for the production of valuable ketocarotenoids, such as canthaxanthin and astaxanthin. Additionally, there is a particularly important need to identify CrtW type ketolases having relatively low to moderate sequence homology (i.e. <65% nucleotide sequence identity) as coexpression of highly homologous genes tends to result genetic instability (i.e. undesirable homologous recombination). Expressing crtW genes having relatively low to moderate sequence homology should decrease the probability of genetic instability normally associated with expression of highly homologous genes. This is particularly important when developing genetically-stable commercial strains for optimal production of the desired product (i.e. ketocarotenoids).

CrtW genes having divergent nucleotide sequences are most suitable for expressing multiple ketolases in a single recombinant host cell. This is especially important when ketolase activity becomes the rate-limiting step in the ketocarotenoid biosynthesis pathway. Increasing the number of crtW genes that can be simultaneously expressed in the production host is expected to increase ketocarotenoid production, assuming that the pool of available substrates is not limiting.

Additionally, CrtW ketolases tend to exhibit substrate flexibility. However, it can be envisioned that different CrtW ketolases may exhibit preferential activity towards one or more possible substrates (i.e. β-carotene versus zeaxanthin). Simultaneous expression of multiple CrtW ketolases, each selected based on their preferred substrate, may be used for optimal production of a desired ketocarotenoid. One of skill in the art may optimize production of the desired ketocarotenoid end product by analyzing the available substrate pool within the desired host cell, selectively expressing an appropriate combination of ketolases for optimal production of the desired ketocarotenoid.

The problem to be solved therefore is to identify and isolate novel crtW ketolase genes useful for engineering production of ketocarotenoids (i.e. canthaxanthin and astaxanthin). The present invention has solved the stated problem by providing three novel crtW genes useful for the production of ketocarotenoids in recombinant host cells. Methods for producing ketocarotenoids using the present CrtW ketolases are also provided.

SUMMARY OF THE INVENTION

The invention relates to new carotenoid ketolase enzymes capable of the conversion of cyclic carotenoids to cyclic ketocarotenoids. Accordingly the invention provides an isolated nucleic acid molecule encoding a carotenoid ketolase enzyme, selected from the group consisting of:
  (a) an isolated nucleic acid molecule encoding an amino acid as set forth in SEQ ID NOs:2, 4, and 6;
  (b) an isolated nucleic acid molecule that hybridizes with
    (a) under the following wash conditions: 0.1×SSC, 0.1% SDS, 65° C.; or
  an isolated nucleic acid molecule that is complementary to (a), or (b).

Similarly the invention provides genetic chimera comprising the isolated nucleic acid molecules operably linked to suitable regulatory sequences, polypeptides encoded by the isolated nucleic acid molecules of the invention and transformed production host cells comprising the same.

The invention additionally provides methods of obtaining the nucleic acid molecules of the invention either by methods of primer directed amplification or by hybridization.

In an other embodiment the invention provides a method for the production of cyclic ketocarotenoid compounds comprising:

(a) providing a host cell which produces cyclic carotenoids;

(b) transforming the host cell of (a) with the genes of the invention encoding a carotenoid ketolase enzyme; and (c) growing the transformed host cell of (b) under conditions whereby a cyclic ketocarotenoid is produced.

Similarly the invention provides a method of regulating cyclic ketocarotenoid biosynthesis in an organism comprising, (a) introducing into a host cell a carotenoid ketolase gene of the invention said gene under the control of suitable regulatory sequences; and (b) growing the host cell of (a) under conditions whereby the carotenoid ketolase gene is expressed and cyclic ketocarotenoid biosynthesis is regulated.

In an alternate embodiment the invention provides a method for the increasing production of cyclic ketocarotenoid compounds comprising:

(a) providing a host cell which produces cyclic carotenoids;

(b) transforming the host cell of (a) with a first gene, of the invention encoding a CrtW carotenoid ketolase enzyme;

(c) transforming the host cell of (a) with a second gene encoding a CrtW carotenoid ketolase enzyme, said second gene having less than 65% nucleic acid sequence identity when compared to said first gene; and (d) growing the transformed host cell comprising said first gene of (a) and said second gene of (b) under conditions whereby the production of cyclic ketocarotenoid is increased relative to a transformed host cell only expressing either said first gene or said second gene.

Mutated genes of the invention are also provided produced by a method comprising the steps of:

(a) digesting a mixture of nucleotide sequences with restriction endonucleases wherein said mixture comprises:

i) a native carotenoid ketolase gene;

ii) a first population of nucleotide fragments which will hybridize to said native carotenoid ketolase gene;

iii) a second population of nucleotide fragments that will not hybridize to said native carotenoid ketolase gene;

wherein a mixture of restriction fragments are produced;

(b) denaturing said mixture of restriction fragments;

(c) incubating the denatured said mixture of restriction fragments of step (ii) with a polymerase;

(d) repeating steps (ii) and (iii) wherein a mutated carotenoid ketolase gene is produced encoding a protein having an altered biological activity.

BRIEF DESCRIPTION OF THE DRAWINGS AND SEQUENCE DESCRIPTIONS

FIG. 1. Illustration of possible pathway intermediates in the synthesis of astaxanthin via ketolase and hydroxylase reactions from β-carotene.

Figure 2A:
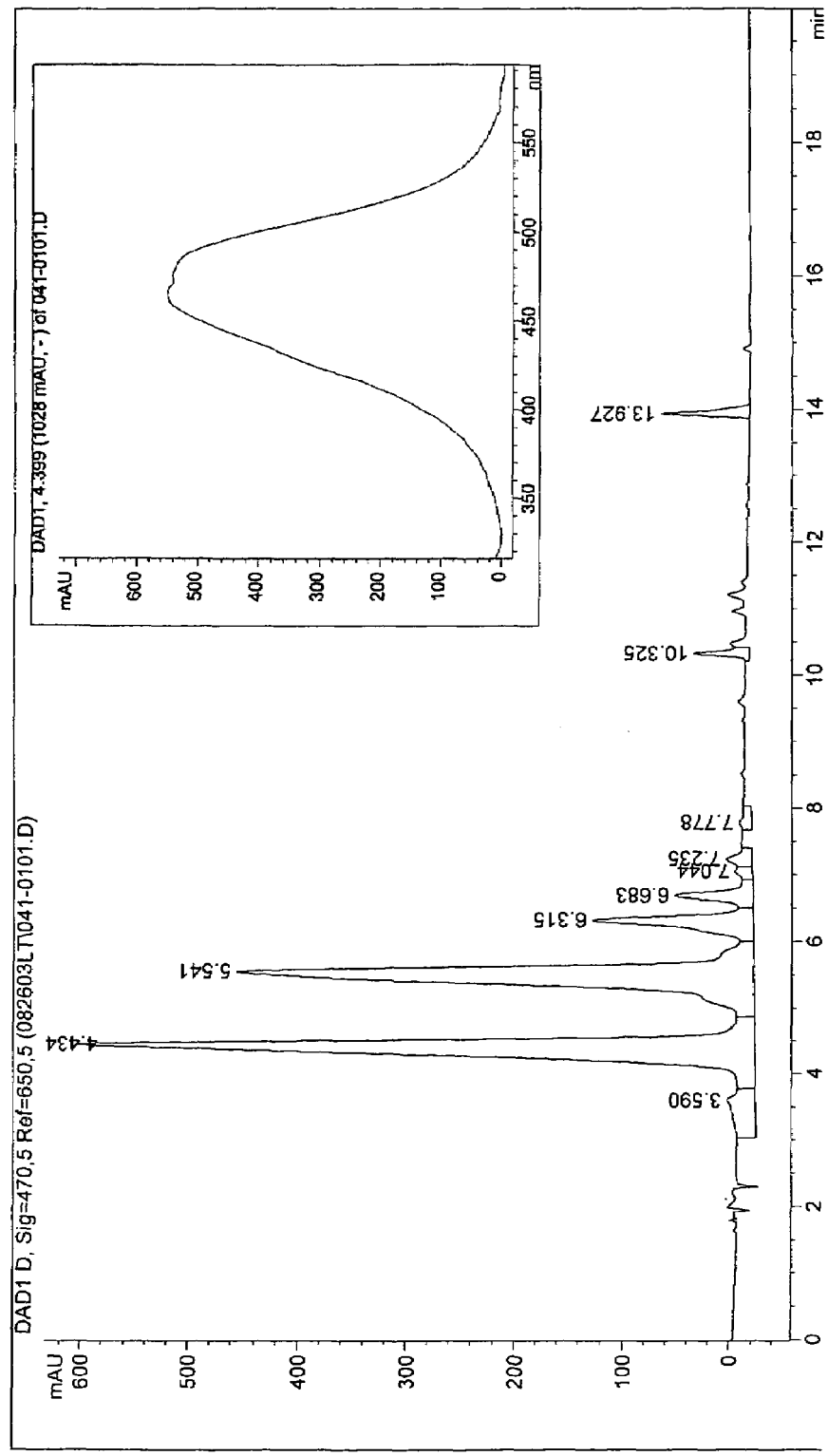
Figure 2B:
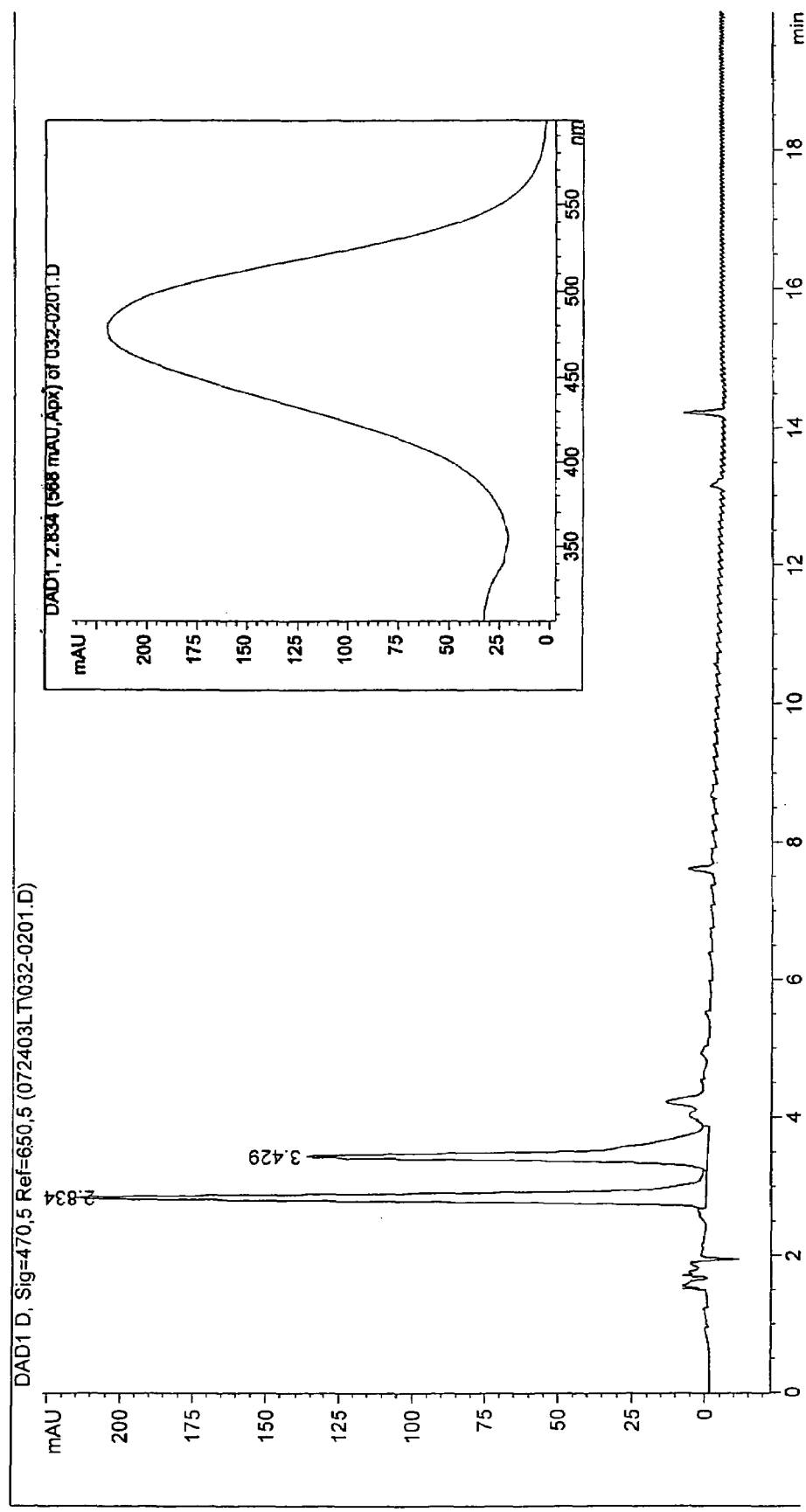
Figure 2C:
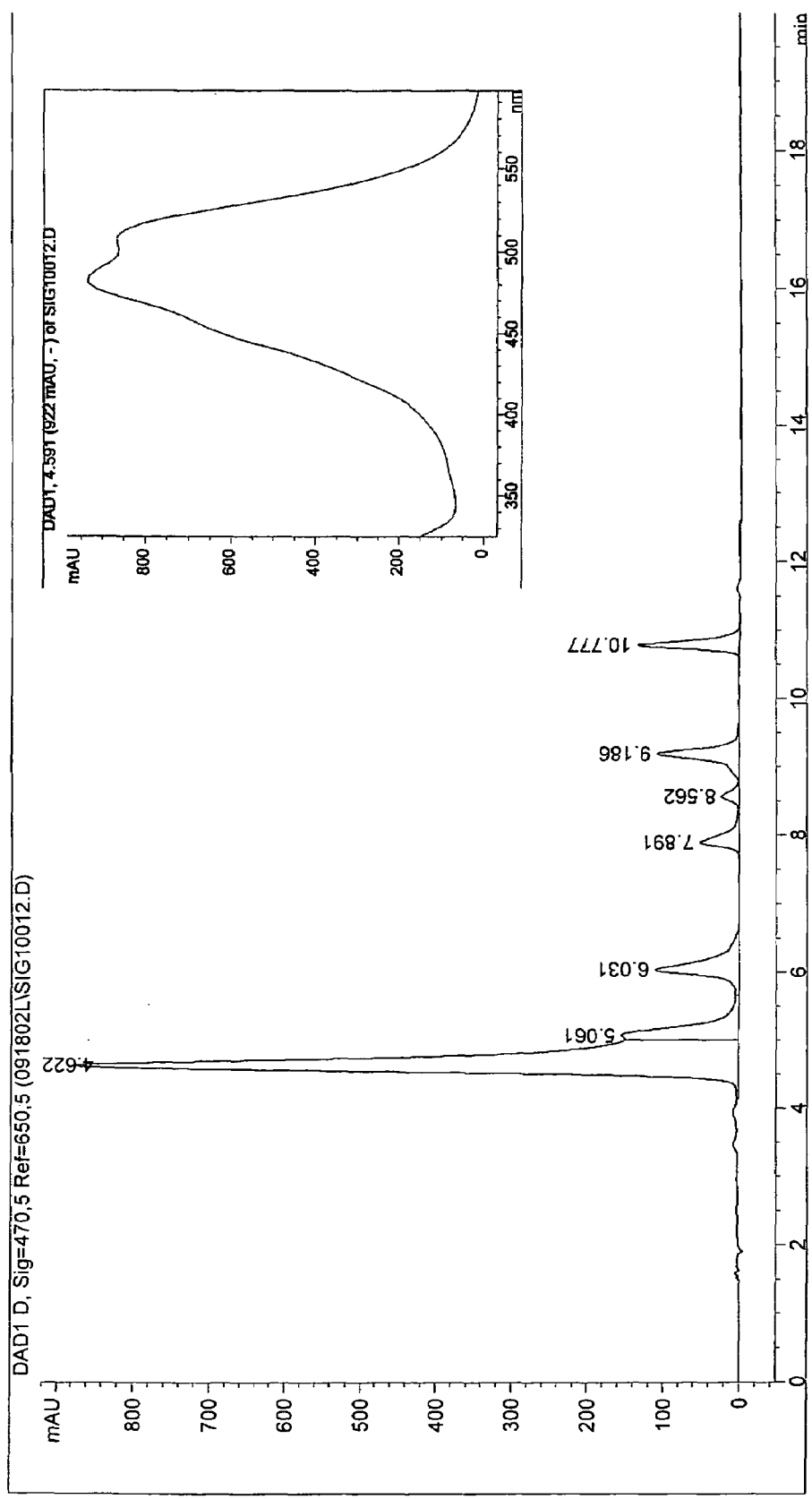

FIG. 2. HPLC analysis of carotenoids produced by the bacterial strains. FIG. 2a shows HPLC data from the analysis of *S. melonis* DC18; FIG. 2b shows HPLC data from the analysis of *B. vesicularis* DC263; and FIG. 2c shows HPLC data from the analysis of *Flavobacterium* sp. K1-202C.

Figure 3:
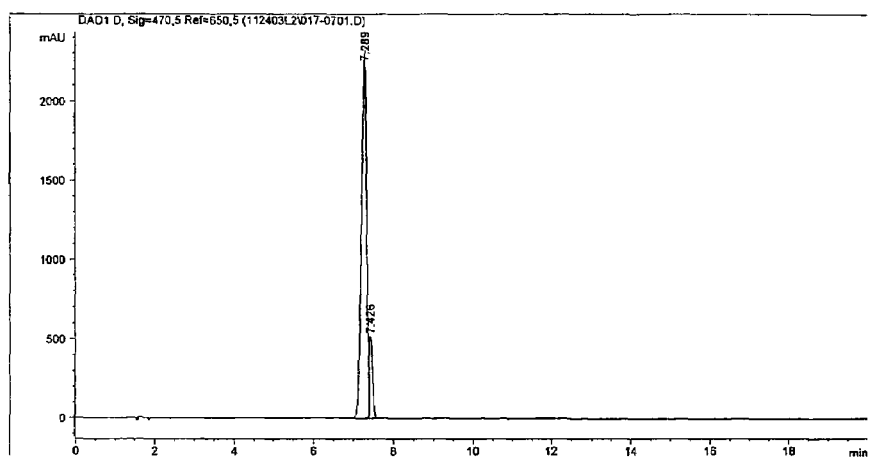
Figure 3:
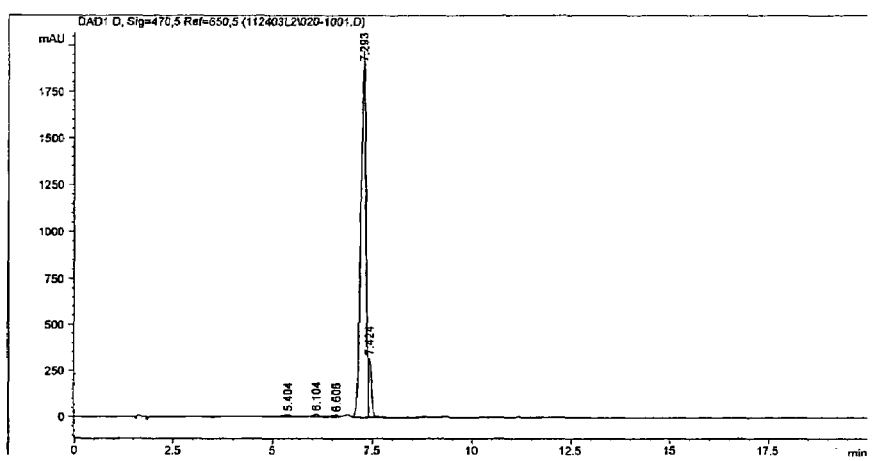
Figure 3:
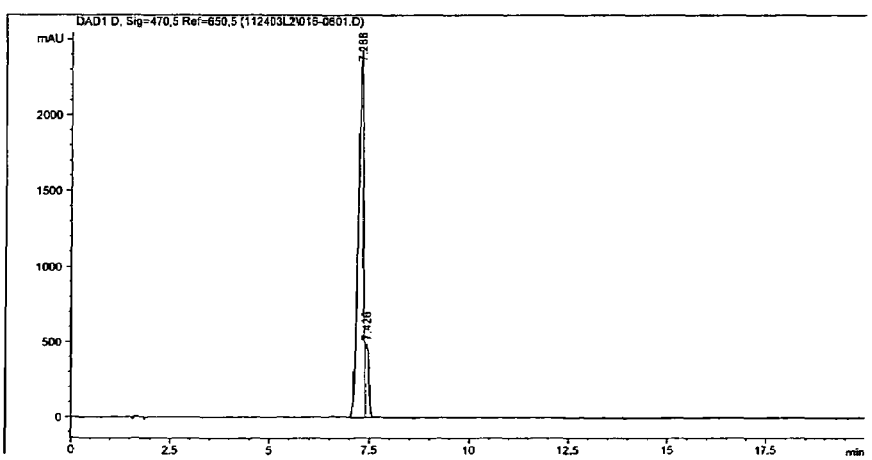

FIG. 3. HPLC data from the analysis of carotenoids produced by β-carotene accumulating *E. coli* strain expressing the divergent crtW genes.

Figure 4:
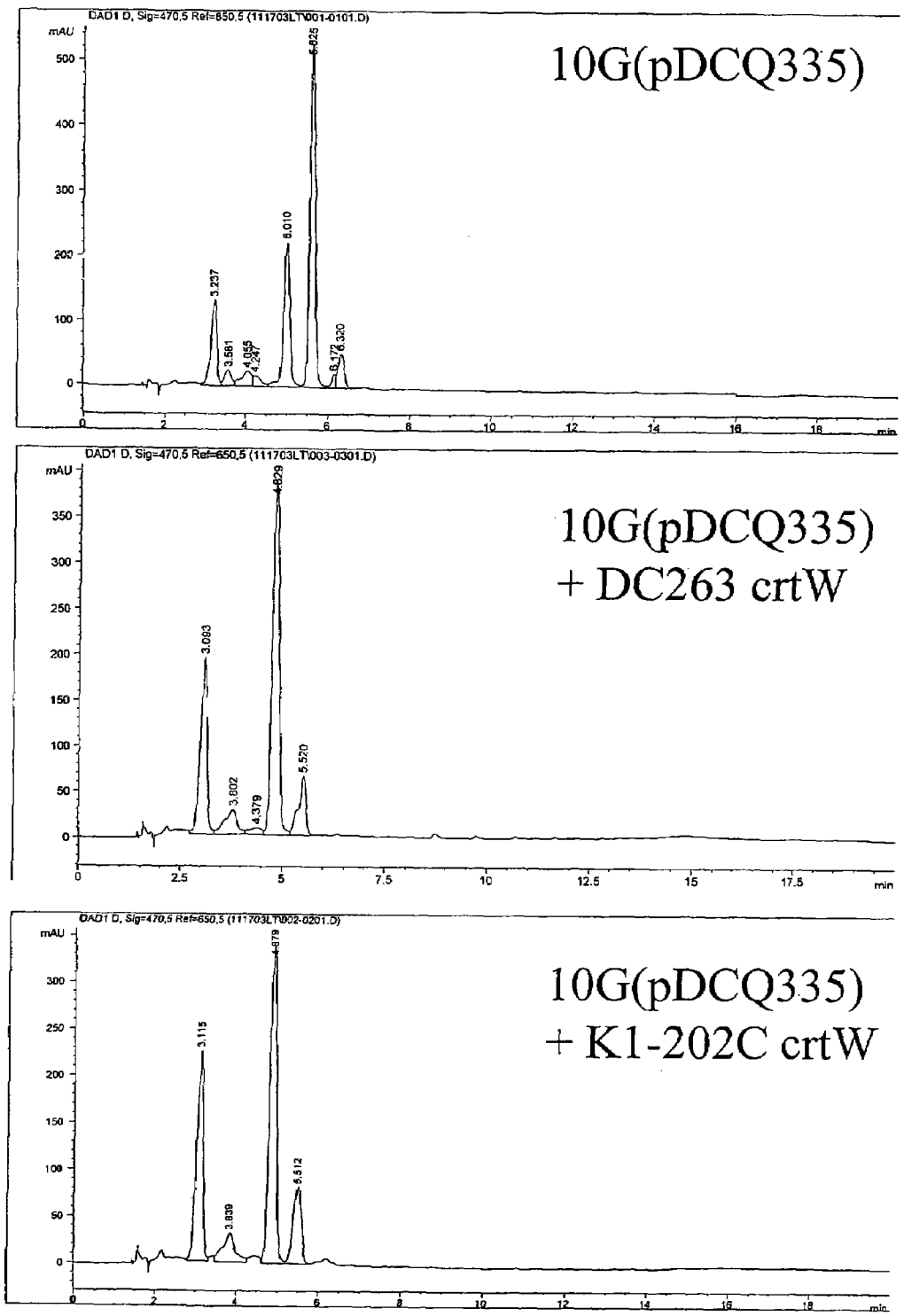

FIG. 4. HPLC data from the analysis of carotenoids produced by astaxanthin-producing *E. coli* strain expressing the divergent crtW genes.

Figure 5:
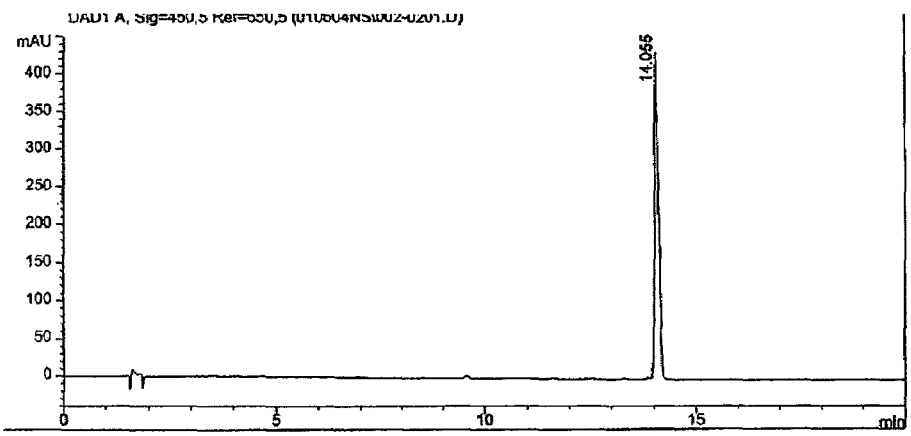
Figure 5:
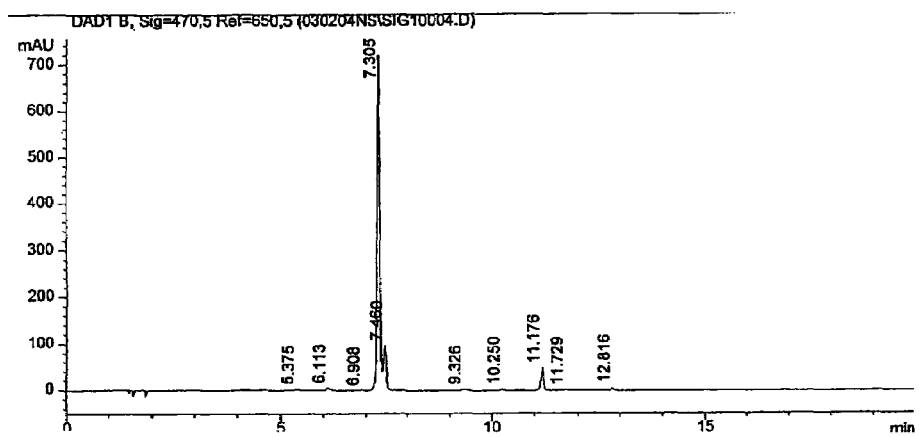
Figure 5:
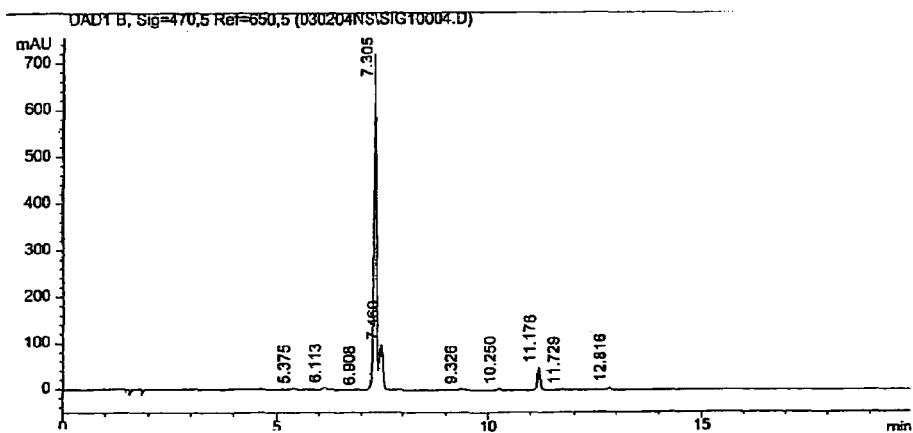

FIG. 5. HPLC analysis of *Methylomonas* sp. 16a cells expressing the divergent crtW genes with β-carotene synthesis genes.

The invention can be more fully understood from the following detailed description and the accompanying sequence descriptions, which form a part of this application.

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of the *Sphingomonas melonis* DC18 crtW ORF.

SEQ ID NO:2 is the deduced amino acid sequence of the *Sphingomonas melonis* DC18 CrtW ketolase.

SEQ ID NO:3 is the nucleotide sequence of *Brevundimonas vesicularis* DC263 crtW ORF.

SEQ ID NO:4 is the deduced amino acid sequence of the *Brevundimonas vesicularis* DC263 CrtW ketolase.

SEQ ID NO:5 is the nucleotide sequence of *Flavobacterium* sp. K1-202C crtW ORF.

SEQ ID NO:6 is the deduced amino acid sequence of the *Flavobacterium* sp. K1-202C CrtW ketolase.

SEQ ID NO:7 is the nucleotide sequence of a primer ("HK12") used for 16S rRNA gene sequencing.

SEQ ID NO:8 is the nucleotide sequence of a primer ("JCR14") used for 16S rRNA gene sequencing.

SEQ ID NO:9 is the nucleotide sequence of a primer ("JCR15") used for 16S rRNA gene sequencing.

SEQ ID NO:10 is the nucleotide sequence of the *Sphingomonas melonis* DC18 16S rRNA gene.

SEQ ID NO:11 is the nucleotide sequence of the *Brevundimonas vesicularis* DC263 16S rRNA gene.

SEQ ID NO:12 is the nucleotide sequence of the crtEidiYIBZ carotenoid synthesis gene cluster from *Pantoea agglomerans* DC404 (U.S. Ser. No. 60/477,874)

SEQ ID NO:13 is the nucleotide sequence of primer pWEB404F.

SEQ ID NO:14 is the nucleotide sequence of primer pWEB404R.

SEQ ID NO:15 is the nucleotide sequence of the crtEidiYIB gene cluster from *P. agglomerans* DC404.

SEQ ID NO:16 is the nucleotide sequence of primer crtW-18_F.

SEQ ID NO:17 is the nucleotide sequence of primer crtW-18_R.

SEQ ID NO:18 is the nucleotide sequence of primer crtW-263_F.

SEQ ID NO:19 is the nucleotide sequence of primer crtW-263_R.

SEQ ID NO:20 is the nucleotide sequence of primer crtW/K1-202CF.

SEQ ID NO:21 is the nucleotide sequence of primer crtW/K1-202CR.

SEQ ID NO:22 is the nucleotide sequence of the *Agrobacterium aurantiacum* crtZ hydroxylase gene.

SEQ ID NO:23 is the nucleotide sequence of the *Agrobacterium aurantiacum* crtW ketolase gene.

SEQ ID NO:24 is the nucleotide sequence of primer crtZW_F.

SEQ ID NO:25 is the nucleotide sequence of primer crtZW_soe_R.

SEQ ID NO:26 is the nucleotide sequence of primer crtZW_soe_F

SEQ ID NO:27 is the nucleotide sequence of primer crtZW_R.

SEQ ID NO:28 is the nucleotide sequence of primer crt-260_F.

SEQ ID NO:29 is the nucleotide sequence of primer crt-260SOE_R.

SEQ ID NO:30 is the nucleotide sequence of primer crt-260SOE_F.

SEQ ID NO:31 is the nucleotide sequence of primer crt-260R1_R.

SEQ ID NO:32 is the nucleotide sequence of primer crt-260R1_F.

SEQ ID NO:33 is the nucleotide sequence of primer crt-260_R.

The following biological deposit was made under the terms of the Budapest Treaty on the International Recognition of the Deposit of Microorganisms for the Purposes of Patent Procedure:

| Depositor Identification Reference | International Depository Designation | Date of Deposit |
|---|---|---|
| *Methylomonas* 16a | ATCC PTA 2402 | Aug. 22, 2000 |

As used herein, "ATCC" refers to the American Type Culture Collection International Depository Authority located at ATCC, 10801 University Blvd., Manassas, Va. 20110-2209, U.S.A. The "International Depository Designation" is the accession number to the culture on deposit with ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The present crtW genes and their expression product, a carotenoid ketolase, are useful for the creation of recombinant organisms that have the ability to produce cyclic ketocarotenoid compounds. Nucleic acid fragments encoding CrtW ketolases have been isolated from several bacterial strains including *Sphingomonas melonis* DC18, *Brevundimonas vesicularis* DC263, and *Flavobacterium* sp. K1-202C. The isolated nucleic acid fragments were identified and characterized by comparison to public databases containing nucleotide and protein sequences using the BLAST and FASTA algorithms, well-known to those skilled in the art.

The present crtW ketolase genes were expressed in transgenic microbial hosts engineered to produce suitable substrates (i.e. β-carotene). Functional expression of the genes was measured by the production of ketocarotenoids (for example, canthaxanthin and astaxanthin) in the heterologous hosts. Additionally, the effects of divergent ketolase coexpression on ketocarotenoid production within the transgenic hosts were characterized by measuring relative changes in ketocarotenoid production.

The genes and gene products of the present invention may be used in a variety of ways for the production or regulation of cyclic ketocarotenoid compounds. The present crtW ketolase genes can be used for ketocarotenoid production in heterologous hosts having the ability to produce suitable substrates. Additionally, two or more of the present crtW ketolase genes may be simultaneously expressed in the heterologous host for optimized production of ketocarotenoids. Simultaneous expression of the present crtW genes is possible due to their relatively low to moderate nucleotide sequence homology to other known CrtW ketolases. The relatively low/moderate homology permits stable expression of multiple CrtW ketolases in the recombinant host cell for optimal ketocarotenoid production.

The gene and gene sequences described herein enable one to incorporate the production of ketocarotenoids directly into an industrially suitable host cell. This aspect makes any recombinant host into which these genes are incorporated a more desirable production host. The ketocarotenoids produced can be isolated from the production host for use in a variety of applications, including animal feed. Optionally, the recombinant host cells (whole, homogenized, or autolysed) can be directly incorporated into animal feed (no carotenoid isolation step) due to the presence of carotenoids that are known to add desirable pigmentation and health benefits. Salmon and shrimp aquacultures are particularly useful applications for this invention as carotenoid pigmentation is critically important for the value of these organisms (F. Shahidi, J. A. Brown, Carotenoid pigments in seafood and aquaculture, *Critical Reviews in Food Science*, 38(1): 1-67 (1998)). Additionally, the ketocarotenoid astaxanthin is known to be a powerful antioxidant and has been reported to boost immune functions in humans and reduce carcinogenesis (Jyonouchi et al., *Nutr. Cancer*, 23:171-183 (1995); Tanaka et al., *Cancer Res.*, 55:4059-4064 (1995)).

In this disclosure, a number of terms and abbreviations are used. The following definitions are provided.

As used herein, the term "comprising" means the presence of the stated features, integers, steps, or components as referred to in the claims, but that it does not preclude the presence or addition of one or more other features, integers, steps, components or groups thereof.

"Open reading frame" is abbreviated ORF.

"Polymerase chain reaction" is abbreviated PCR.

As used herein, the terms "isolated nucleic acid fragment" or "isolated nucleic acid molecule" will be used interchangeably and will refer to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "pBHR-crt1" refers to a β-carotene producing plasmid. The plasmid was constructed by cloning the crtEXYIB carotenoid gene cluster from *Pantoea stewartii* (ATCC 8199) into pBHR1 (MoBioTech, Goettingen, Germany; and U.S. Ser. No. 09/941,947, hereby incorporated by reference). The resulting plasmid contained the *P. stewartii* gene cluster expressed under the control of the chloramphenicol-resistance gene promoter.

The term, "pDCQ329" refers to a β-carotene producing plasmid. The plasmid was constructed by cloning the crtEXYIB carotenoid gene cluster from *Enterobactericeae* DC260 into pBHR1 (U.S. Ser. No. 10/808,979).

The term "pDCQ330" refers to a β-carotene producing plasmid. The plasmid was constructed by cloning the crtEidiYIB carotenoid gene cluster from *Pantoea agglomerans* DC404 into broad host range vector pBHR1.

The term "pCDQ335" refers to a plasmid comprising the β-carotene synthesis gene cluster from pDCQ330 and the *Agrobacterium aurantiacum* crtZW genes. Plasmid pDCQ335 contains the crtZWEidiYIB genes in an operon under the control of the chloramphenicol resistance gene promoter. The resulting plasmid, when transformed into an appropriate heterologous host, enables the production of astaxanthin (FIG. 1).

The term "pDCQ335TA" refers to a plasmid comprising the *Agrobacterium aurantiacum* crtWZ genes cloned into a pTrcHis2-TOPO expression vector (Invitrogen, Carlsbad, Calif.).

The term "pDCQ340" refers to a β-carotene producing plasmid. The plasmid contains the crtEYIB genes from *Enterobactericeae* DC260 cloned into the broad host range vector pBHR1.

The term "pDCQ341TA" refers to a plasmid expressing the crtW gene from *Sphingomonas melonis* DC18 cloned into a pTrcHis2-TOPO vector (Invitrogen).

The term "pDCQ342TA" refers to a plasmid expressing the crtW gene from *Brevundimonas vesicularis* DC263 cloned into a pTrcHis2-TOPO vector (Invitrogen).

The term "pDCQ339TA" refers to a plasmid expressing the crtW gene from *Flavobacterium* sp. K1-202C cloned into a pTrcHis2-TOPO vector (Invitrogen).

The term "isoprenoid" or "terpenoid" refers to the compounds are any molecule derived from the isoprenoid pathway, including 10 carbon terpenoids and their derivatives, such as carotenoids and xanthophylls.

The term "carotenoid" refers to a compound composed of a polyene backbone which is condensed from five-carbon isoprene unit. Carotenoids can be acyclic or terminated with one (monocyclic) or two (bicyclic) cyclic end groups. The term "carotenoid" may include both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids that are particularly suitable in the present invention are monocyclic and bicyclic carotenoids.

The term "carotenoid biosynthetic pathway" refers to those genes comprising members of the "upper isoprenoid pathway" and/or the "lower carotenoid biosynthetic pathway".

The terms "upper isoprenoid pathway" and "upper pathway" are used interchangeably and refer to enzymes involved in converting pyruvate and glyceraldehyde-3-phosphate to farnesyl pyrophosphate (FPP). Genes encoding these enzymes include, but are not limited to: the "dxs" gene (encoding 1-deoxyxylulose-5-phosphate synthase); the "dxr" gene (encoding 1-deoxyxylulose-5-phosphate reductoisomerase; also known as the ispC); the "ispD" gene (encoding a 2C-methyl-D-erythritol cytidyltransferase enzyme; also known as ygbP); the "ispE" gene (encoding 4-diphosphocytidyl-2-C-methylerythritol kinase; also known as ychB); the "ispF" gene (encoding a 2C-methyl-D-erythritol 2,4-cyclodiphosphate synthase; also known as ygbB); the "pyrG" gene (encoding a CTP synthase; also known as ispF); the "lytB" gene (also known as ispH) involved in the formation of dimethylallyl diphosphate; the "gcpE" gene (also known as ispG) involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase) in the isoprenoid pathway.

The terms "lower carotenoid biosynthetic pathway" and "lower pathway" will be used interchangeably and refer to those enzymes which convert FPP to a suite of carotenoids. These include those genes and gene products that are involved in the synthesis of either diapophytoene (whose synthesis represents the first step unique to biosynthesis of $C_{30}$ carotenoids) or phytoene (whose synthesis represents the first step unique to biosynthesis of $C_{40}$ carotenoids). All subsequent reactions leading to the production of various $C_{30}$-$C_{40}$ carotenoids are included within the lower carotenoid biosynthetic pathway. These genes and gene products comprise all of the "crt" genes including, but not limited to: crtM, crtN, crtN2, crtE, crtX, crtY, crtI, crtB, crtZ, crtW, crtO, crtR, crtA, crtC, crtD, crtF, and crtU. Finally, the term "lower carotenoid biosynthetic enzyme" is an inclusive term referring to any and all of the enzymes in the lower pathway including, but not limited to: CrtM, CrtN, CrtN2, CrtE, CrtX, CrtY, CrtI, CrtB, CrtZ, CrtW, CrtO, CrtR, CrtA, CrtC, CrtD, CrtF, and CrtU.

"$C_{30}$ diapocarotenoids" consist of six isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{30}$ carotenoids may be formally derived from the acyclic $C_{30}H_{42}$ structure, having a long central chain of conjugated double bonds, by: (i) hydrogenation (ii) dehydrogenation, (iii) cyclization, (iv) oxidation, (v) esterification/glycosylation, or any combination of these processes.

"Tetraterpenes" or "$C_{40}$ carotenoids" consist of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{40}$ carotenoids may be formally derived from the acyclic $C_{40}H_{56}$ structure. Non-limiting examples of $C_{40}$ carotenoids include: phytoene, lycopene, β-carotene, zeaxanthin, astaxanthin, and canthaxanthin.

The term "CrtE" refers to a geranylgeranyl pyrophosphate synthase enzyme encoded by the crtE gene and which converts trans-trans-farnesyl diphosphate and isopentenyl diphosphate to pyrophosphate and geranylgeranyl diphosphate.

The term "Idi" refers to an isopentenyl diphosphate isomerase enzyme (E.C. 5.3.3.2) encoded by the idi gene.

The term "CrtY" refers to a lycopene cyclase enzyme encoded by the crtY gene, which converts lycopene to β-carotene.

The term "CrtI" refers to a phytoene desaturase enzyme encoded by the crtI gene. CrtI converts phytoene into lycopene via the intermediaries of phytofluene, ζ-carotene, and neurosporene by the introduction of 4 double bonds.

The term "CrtB" refers to a phytoene synthase enzyme encoded by the crtB gene, which catalyzes the reaction from prephytoene diphosphate to phytoene.

The term "CrtZ" refers to a β-carotene hydroxylase enzyme encoded by the crtZ gene, which catalyzes a hydroxylation reaction from β-carotene to zeaxanthin.

The term "CrtW" refers to a β-carotene ketolase enzyme encoded by the crtW gene, which catalyzes an oxidation reaction where a keto group is introduced on the ionone ring of cyclic carotenoids. It is known that CrtW ketolases typically exhibit substrate flexibility. The term "carotenoid ketolase" or "ketolase" refers to the group of enzymes that can add keto groups to the ionone ring of cyclic carotenoids.

The term "CrtX" refers to a zeaxanthin glucosyl transferase enzyme encoded by the crtX gene and which converts zeaxanthin to zeaxanthin-β-diglucoside.

The term "keto group" or "ketone group" will be used interchangeably and refers to a group in which a carbonyl group is bonded to two carbon atoms: $R_2C=O$ (neither R may be H).

The term "ketocarotenoid" refers to carotenoids possessing at least one keto group on the ionone ring of a cyclic carotenoid. Examples of ketocarotenoids include, but are not limited to canthaxanthin and astaxanthin.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1× SSC, 0.1% SDS, 65° C. and washed with 2×SSC, 0.1% SDS followed by 0.1×SSC, 0.1% SDS), with the sequences exemplified herein. In one embodiment, substantially similar nucleic acid fragments of the instant invention are those nucleic acid fragments whose DNA sequences are at least about 80% identical to the DNA sequence of the nucleic acid fragments reported herein. In another embodiment, substantially similar nucleic acid fragments are at least about 90% identical to the DNA sequence of the nucleic acid fragments reported herein. In yet a further embodiment, substantially similar nucleic acid fragments are at least about 95% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989) (hereinafter "Maniatis"), particularly Chapter 11 and Table 11.1 therein. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. In one embodiment, the stringency conditions use a series of washes starting with 6×SSC, 0.5% SDS at room temperature for about 15 min, then repeated with 2×SSC, 0.5% SDS at about 45° C. for about 30 min, and then repeated twice with 0.2×SSC, 0.5% SDS at about 50° C. for about 30 min. In another embodiment, the stringency conditions use higher temperatures in which the washes are identical to those above except for the temperature of the final two 30 min washes in 0.2×SSC, 0.5% SDS was increased to about 60° C. In yet another embodiment, highly stringent conditions use two final washes in 0.1×SSC, 0.1% SDS at about 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well-known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment, the length for a hybridizable nucleic acid is at least about 10 nucleotides. In another embodiment, the minimum length for a hybridizable nucleic acid is at least about 15 nucleotides; in yet another embodiment at least about 20 nucleotides; and in yet a further embodiment, the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403-410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising about 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of about 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, N.Y. (1988); *Biocomputing: Informatics and Genome Projects* (Smith, D. W., ed.) Academic Press, N.Y. (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, N.Y. (1991). In one embodiment, the methods used to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences can be performed using the Clustal method of alignment (Higgins and Sharp, *CABIOS.*, 5:151-153 (1989)) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 75% identical. In one embodiment, suitable nucleic acid fragments are at least about 85% identical to the amino acid sequences reported herein. In another embodiment, the nucleic acid fragments encode amino acid sequences that are at least about 90% identical to the amino acid sequences reported herein. In a further embodiment, nucleic acid fragments encode amino acid sequences that are at least about 95% identical to the amino acid sequences reported herein. In yet a further embodiment, the suitable nucleic acid fragments encode amino acid sequences that are at least about 99% identical to the amino acid sequences reported herein. Suitable nucleic acid fragments of the present invention not only have the above homologies, but typically encode a polypeptide having at least about 240 amino acids.

In the present invention, the terms "divergent gene", "divergent ketolase", and "divergent sequence" are used interchangeably and refer to the lack of nucleic acid fragment sequence identity among CrtW ketolases. Nucleotide sequence comparisons between 2 or more crtW genes allows classification of the relationship(s) as to the relative degree of sequence identity. Simultaneous expression of highly homologous genes tends to result in genetic instability (i.e. increased rate of homologous recombination). Expression of moderately or highly divergent genes is likely to result in genetic stability. As used herein, "genetic stability" or "genetically stable" will be used to described the expression of multiple carotenoid ketolase genes having coding sequence with less than 75% nucleic acid sequence identity to the present carotenoid ketolase genes, preferably less than 65% nucleic acid sequence identity. This is particularly important when chromosomally integrating more than one carotenoid ketolase gene for increasing ketocarotenoid production in a genetically stable transformant. In one embodiment, the crtW ketolase genes useful for coexpression are those that share less than 75% identify when compared by sequence alignment. In another embodiment, the crtW ketolase genes used for coexpression are those that share less than about 65% identify when compared by sequence alignment. In a further embodiment, the crtW genes used for coexpression are those that share less than about 55% identify when compared by sequence alignment. In yet a further embodiment, the crtW genes used for coexpression are those that share less than about 45% identify when compared by sequence alignment.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID NOs: 2, 4, and 6. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts (normally limited to eukaryotes) to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. As used herein, the host cell genome includes both chromosomal or extrachromosomal (i.e. a vector) genes with the host cell. Host organisms containing the transformed nucleic acid fragments are referred to as "transgenic" or "recombinant" or "transformed" organisms.

"Conjugation" refers to a particular type of transformation in which a unidirectional transfer of DNA (e.g., from a bacterial plasmid) occurs from one bacterium cell (i.e., the "donor") to another (i.e., the "recipient"). The process involves direct cell-to-cell contact.

The term "carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof. The term "$C_1$ carbon substrate" refers to any carbon-containing molecule that lacks a carbon-carbon bond. Non-limiting examples are methane, methanol, formaldehyde, formic acid, formate, methylated amines (e.g., mono-, di-, and tri-methyl amine), methylated thiols, and carbon dioxide. In one embodiment, the $C_1$ carbon substrate is methanol and/or methane.

The term "$C_1$ metabolizer" refers to a microorganism that has the ability to use a single carbon substrate as its sole source of energy and biomass. $C_1$ metabolizers will typically be methylotrophs and/or methanotrophs. The term "$C_1$ metabolizing bacteria" refers to bacteria that have the ability to use a single carbon substrate as their sole source of energy and biomass. $C_1$ metabolizing bacteria, a subset of $C_1$ metabolizers, will typically be methylotrophs and/or methanotrophs. In one embodiment, the $C_1$ metabolizer is a methylotroph and the single carbon substrate is selected from the group consisting of methane and/or methanol. In another embodiment, the $C_1$ metabolizer is a methanotroph and the single carbon substrate is selected from the group consisting of methane and/or methanol.

The term "methylotroph" means an organism capable of oxidizing organic compounds that do not contain carbon-carbon bonds. Where the methylotroph is able to oxidize $CH_4$, the methylotroph is also a methanotroph.

The term "methanotroph" or "methanotrophic bacteria" means a prokaryote capable of utilizing methane as its primary source of carbon and energy. Complete oxidation of methane to carbon dioxide occurs by aerobic degradation pathways. Typical examples of methanotrophs useful in the present invention include (but are not limited to) the genera *Methylomonas, Methylobacter, Methylococcus,* and *Methylosinus.*

The term "high growth methanotrophic bacterial strain" refers to a bacterium capable of growth with methane and/or methanol as the sole carbon and energy source and which possesses a functional Embden-Meyerhof carbon flux pathway, resulting in a high rate of growth and yield of cell mass per gram of $C_1$ substrate metabolized (U.S. Pat. No. 6,689,601). The specific "high growth methanotrophic bacterial strain" described herein is referred to as "*Methylomonas* 16a", "16a" or "*Methylomonas* sp. 16a", which terms are used interchangeably and which refer to the *Methylomonas* strain used in the present invention.

The term "CrtN1" refers to an enzyme encoded by the crtN1 gene, active in the native carotenoid biosynthetic pathway of *Methylomonas* sp. 16a. This gene is located within an an operon comprising crtN2 and ald.

The term "ALD" refers to an enzyme encoded by the ald gene, active in the native carotenoid biosynthetic pathway of *Methylomonas* sp. 16a. This gene is located within an an operon comprising crtN1 and crtN2.

The term "CrtN2" refers to an enzyme encoded by the crtN2 gene, active in the native carotenoid biosynthetic pathway of *Methylomonas* sp. 16a. This gene is located within an an operon comprising crtN1 and ald.

The term "CrtN3" refers to an enzyme encoded by the crtN3 gene, active in the native carotenoid biosynthetic pathway of *Methylomonas* sp. 16a. This gene is not located within the crt gene cluster; instead this gene is present in a different location within the *Methylomonas* genome.

The terms "crtN1 gene cluster", "$C_{30}$ crt gene cluster", "crt gene cluster", and "endogenous *Methylomonas* crt gene cluster" refer to an operon comprising crtN1, ald, and crtN2 genes that is active in the native carotenoid biosynthetic pathway of *Methylomonas* sp. 16a.

The term "MWM1200 (Δcrt cluster promoter+ΔcrtN3)" refers to a mutant of *Methylomonas* sp. 16a in which the $C_{30}$ crt cluster promoter and the crtN3 gene have been disrupted. Disruption of the native $C_{30}$ carotenoid biosynthetic pathway results in suitable background for engineering $C_{40}$ carotenoid production. The *Methylomonas* MWM1200 strain was previously created and is a suitable carotenoid production host (U.S. Ser. No. 60/527,083; hereby incorporated by reference). The term "pigmentless" or "white mutant" refers to a *Methylomonas* sp. 16a bacterium wherein the native pink pigment (e.g., a $C_{30}$ carotenoid) is not produced. Thus, the bacterial cells appear white in color, as opposed to pink.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992,111-20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters (as set by the software manufacturer) which originally load with the software when first initialized.

The present invention provides newly discovered crtW genes encoding carotenoid ketolases. The present CrtW ketolases may be used in vitro and/or in vivo for the production of ketocarotenoids from cyclic carotenoid compounds.

Comparison of the *Sphingomonas melonis* DC18 crtW nucleotide base and deduced amino acid sequences to public databases reveals that the most similar known sequences were about 57% identical to the amino acid sequence of reported herein over length of 249 amino acid using a Smith-Waterman alignment algorithm (W. R. Pearson, *Comput. Methods Genome Res., [Proc. Int. Symp.*] (1994), Meeting Date 1992, 111-20. Editor(s): Suhai, Sandor. Publisher: Plenum, New York, N.Y.).

Comparison of the *Brevundimonas vesicularis* DC263 crtW nucleotide base and deduced amino acid sequences to public databases reveals that the most similar known sequences were about 63% identical to the amino acid sequence of reported herein over length of 259 amino acid using a Smith-Waterman alignment algorithm.

Comparison of the *Flavobacterium* sp. K1-202C crtW nucleotide base and deduced amino acid sequences to public databases reveals that the most similar known sequences were about 47% identical to the amino acid sequence of reported herein over length of 256 amino acid using a Smith-Waterman alignment algorithm.

In one embodiment, the present invention is comprised of nucleic acid fragments encoding amino acid sequences that are at least about 75%-85% identical to the sequences herein. In another embodiment, the present invention is comprised of nucleic acid fragments encoding amino acid sequences that are at least about 85% to about 95% identical to the amino acid sequences reported herein. In a further embodiment, the present invention is comprised of nucleic acid fragments encoding amino acid sequences are at least about 95% identical to the amino acid sequences reported herein. In yet a further embodiment, the present invention is comprised of nucleic acid fragments encoding amino acid sequences that are at least 99% identical to the amino acid sequences reported herein.

Similarly, suitable nucleic acid fragments are those comprised of nucleic acid sequences encoding the corresponding active CrtW ketolases which are at least about 80% identical to the nucleic acid sequences of reported herein. In one embodiment, suitable crtW nucleic acid fragments are those having nucleic acid sequences that are at least about 90% identical to the nucleic acid sequences herein. In another embodiment, suitable crtW nucleic acid fragments are those having nucleic acid sequences that are at least about 95% identical to the nucleic acid sequences herein. In yet another embodiment, suitable crtW nucleic acid fragments are those having nucleic acid sequences that are at least about 99% identical to the nucleic acid sequences reported herein.

Isolation of Homologs

The nucleic acid fragments of the instant invention may be used to isolate genes encoding homologous proteins from the same or other microbial species. Isolation of homologous genes using sequence-dependent protocols is well-known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202), ligase chain reaction (LCR), Tabor, S. et al., *Proc. Natl. Acad. Sci. USA*, 82:1074 (1985)) or strand displacement amplification (SDA, Walker, et al., *Proc. Natl. Acad. Sci. U.S.A.*, 89:392 (1992)).

For example, genes encoding similar proteins or polypeptides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, end-labeling techniques, or RNA probes using available in vitro transcription systems. In addition, specific primers can be designed and used to amplify a part of or the full-length of the instant sequences. The resulting amplification products can be labeled directly during amplification reactions or labeled after amplification reactions, and used as probes to isolate full length DNA fragments under conditions of appropriate stringency.

Typically in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33-50 IRL Press, Herndon, Va.); Rychlik, W., in *Methods in Molecular Biology: PCR Protocols: Current Methods and Applications*, Vol. 15, pages 31-39, White, B. A. (ed.), (1993) Humania Press, Inc., Totowa, N.J.)

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor of a eukaryotic gene. In the case of microbial genes which lack polyadenylated mRNA, random primers may be used. Random primers may also be useful for amplification from DNA.

Alternatively, the second primer sequence may be based upon sequences derived from the cloning vector. For example, the skilled artisan can follow the RACE protocol (Frohman et al., *Proc. Natl. Acad. Sci. USA*, 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *Proc. Natl. Acad. Sci. USA*, 86:5673 (1989); Loh et al., *Science*, 243:217 (1989)).

Alternatively, the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically, a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.*, 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1M sodium chloride, about 0.05 to 0.1M buffers, such as sodium citrate, Tris-HCl, PIPES or HEPES (pH range about 6-9), about 0.05 to 0.2% detergent, such as sodium dodecylsulfate, or between 0.5-20 mM EDTA, FICOLL (Pharmacia Inc.) (about 300-500 kilodaltons), polyvinylpyrrolidone (about 250-500 kD), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A., *Adv. Immunol.*, 36:1 (1984); Maniatis, supra).

Genes Involved in Carotenoid Production

The enzymatic pathway involved in the biosynthesis of carotenoids can be conveniently viewed in two parts, the upper isoprenoid pathway providing for the conversion of pyruvate and glyceraldehyde-3-phosphate to farnesyl pyrophosphate (FPP) and the lower carotenoid biosynthetic pathway, which provides for the synthesis of phytoene and all subsequently produced carotenoids. The upper pathway is ubiquitous in many non-carotogenic microorganisms and in these cases it will only be necessary to introduce genes that comprise the lower pathway for the biosynthesis of the desired carotenoid. The key division between the two pathways concerns the synthesis of farnesyl pyrophosphate. Where FPP is naturally present, only elements of the lower carotenoid pathway will be needed. However, it will be appreciated that for the lower pathway carotenoid genes to be effective in the production of carotenoids, it will be necessary for the host cell to have suitable levels of FPP within the cell. In another embodiment, isoprenoid biosynthesis genes may be optionally upregulated to increase the levels of FPP available for cartenoid biosynthesis. Where FPP synthesis is not provided by the host cell, it will be necessary to introduce the genes necessary for the production of FPP. Each of these pathways will be discussed below in detail.

The Upper Isoprenoid Pathway

Isoprenoid biosynthesis occurs through either of two pathways, generating the common C5 isoprene sub-unit, isopentenyl pyrophosphate (IPP). First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.*, 111:135-140 (1993); Rohmer et al., *Biochem.*, 295: 517-524 (1993); Schwender et al., *Biochem.*, 316: 73-80 (1996); and Eisenreich et al., *Proc. Natl. Acad. Sci. USA*, 93: 6431-6436 (1996)).

Many steps in the mevalonate-independent isoprenoid pathway are known. For example, the initial steps of the alternate pathway leading to the production of IPP have been studied in *Mycobacterium tuberculosis* by Cole et al. (*Nature*, 393:537-544 (1998)). The first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR), encoded by the gene dxr (also known as ispC). 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP. Recently, however, the ygbP gene was renamed as ispD as a part of the isp gene cluster (SwissProtein Accession #Q46893).

Next, the $2^{nd}$ position hydroxy group of 4-diphosphocytidyl-2C-methyl-D-erythritol can be phosphorylated in an ATP-dependent reaction by the enzyme encoded by the ychB gene. YchB phosphorylates 4-diphosphocytidyl-2C- methyl-D-erythritol, resulting in 4-diphosphocytidyl-2C-methyl-D-erythritol 2-phosphate. The ychB gene was renamed as ispE, also as a part of the isp gene cluster (SwissProtein Accession #P24209). YgbB converts 4-diphosphocytidyl-2C-methyl-D-erythritol 2-phosphate to 2C-methyl-D-erythritol 2,4-cyclodiphosphate in a CTP-dependent manner. This gene has also been recently renamed as ispF (SwissProtein Accession #P36663).

The enzymes encoded by the gcpE (also known as ispG) and lytB (also known as ispH) genes (and perhaps others) are thought to participate in the reactions leading to formation of isopentenyl pyrophosphate (IPP) and dimethylallyl pyrophosphate (DMAPP). IPP may be isomerized to DMAPP via IPP isomerase, encoded by the idi gene. However, this enzyme is not essential for survival and may be absent in some bacteria using 2-C-methyl-D-erythritol 4-phosphate (MEP) pathway. Recent evidence suggests that the MEP pathway branches before IPP and separately produces IPP and DMAPP via the lytB gene product. A lytB knockout mutation is lethal in *E. coli* except in media supplemented with both IPP and DMAPP.

The synthesis of FPP occurs via the isomerization of IPP to dimethylallyl pyrophosphate. This reaction is followed by a sequence of two prenyltransferase reactions catalyzed by ispA, leading to the creation of geranyl pyrophosphate (GPP; a 10-carbon molecule) and farnesyl pyrophosphate (FPP; a 15-carbon molecule).

Genes encoding elements of the upper pathway are known from a variety of plant, animal, and bacterial sources, as shown in Table 1.

TABLE 1

Sources of Genes Encoding the Upper Isoprene Pathway

| Gene | GenBank ® Accession Number and Source Organism |
|---|---|
| dxs (D-1-deoxyxylulose 5-phosphate synthase) | AF035440, *Escherichia coli*<br>Y18874, *Synechococcus* PCC6301<br>AB026631, *Streptomyces* sp. CL190<br>AB042821, *Streptomyces griseolosporeus*<br>AF111814, *Plasmodium falciparum*<br>AF143812, *Lycopersicon esculentum*<br>AJ279019, *Narcissus pseudonarcissus*<br>AJ291721, *Nicotiana tabacum* |
| dxr (ispC) (1-deoxy-D-xylulose 5-phosphate reductoisomerase) | AB013300, *Escherichia coli*<br>AB049187, *Streptomyces griseolosporeus*<br>AF111813, *Plasmodium falciparum*<br>AF116825, *Mentha x piperita*<br>AF148852, *Arabidopsis thaliana*<br>AF182287, *Artemisia annua*<br>AF250235, *Catharanthus roseus*<br>AF282879, *Pseudomonas aeruginosa*<br>AJ242588, *Arabidopsis thaliana*<br>AJ250714, *Zymomonas mobilis* strain ZM4<br>AJ292312, *Klebsiella pneumoniae*,<br>AJ297566, *Zea mays* |
| ygbP (ispD) (2-C-methyl-D-erythritol 4-phosphate cytidylyltransferase) | AB037876, *Arabidopsis thaliana*<br>AF109075, *Clostridium difficile*<br>AF230736, *Escherichia coli*<br>AF230737, *Arabidopsis thaliana* |
| ychB (ispE) (4-diphosphocytidyl-2-C-methyl-D-erythritol kinase) | AF216300, *Escherichia coli*<br>AF263101, *Lycopersicon esculentum*<br>AF288615, *Arabidopsis thaliana* |
| ygbB (ispF) (2-C-methyl-D-erythritol 2,4-cyclodiphosphate synthase) | AB038256, *Escherichia coli* mecs gene<br>AF230738, *Escherichia coli*<br>AF250236, *Catharanthus roseus* (MECS)<br>AF279661, *Plasmodium falciparum*<br>AF321531, *Arabidopsis thaliana* |
| gcpE (ispG) | O67496, *Aquifex aeolicus* |
| (1-hydroxy-2-methyl-2-(E)-butenyl 4-diphosphate synthase) | P54482, *Bacillus subtilis*<br>Q9pky3, *Chlamydia muridarum*<br>Q9Z8H0, *Chlamydophila pneumoniae*<br>O84060, *Chlamydia trachomatis*<br>P27433, *Escherichia coli*<br>P44667, *Haemophilus influenzae*<br>Q9ZLL0, *Helicobacter pylori* J99<br>O33350, *Mycobacterium tuberculosis*<br>S77159, *Synechocystis* sp.<br>Q9WZZ3, *Thermotoga maritima*<br>O83460, *Treponema pallidum*<br>Q9JZ40, *Neisseria meningitidis*<br>Q9PPM1, *Campylobacter jejuni*<br>Q9RXC9, *Deinococcus radiodurans*<br>AAG07190, *Pseudomonas aeruginosa*<br>Q9KTX1, *Vibrio cholerae* |
| lytB (ispH) | AF027189, *Acinetobacter* sp. BD413<br>AF098521, *Burkholderia pseudomallei*<br>AF291696, *Streptococcus pneumoniae*<br>AF323927, *Plasmodium falciparum* gene<br>M87645, *Bacillus subtillis*<br>U38915, *Synechocystis* sp.<br>X89371, *C. jejuni* sp. O67496 |
| ispA (FPP synthase) | AB003187, *Micrococcus luteus*<br>AB016094, *Synechococcus elongatus*<br>AB021747, *Oryza sativa* FPPS1 gene for farnesyl diphosphate synthase<br>AB028044, *Rhodobacter sphaeroides*<br>AB028046, *Rhodobacter capsulatus*<br>AB028047, *Rhodovulum sulfidophilum*<br>AF112881 and AF136602, *Artemisia annua*<br>AF384040, *Mentha x piperita*<br>D00694, *Escherichia coli*<br>D13293, *B. stearothermophilus*<br>D85317, *Oryza sativa*<br>X75789, *A. thaliana*<br>Y12072, *G. arboreum*<br>Z49786, *H. brasiliensis*<br>U80605, *Arabidopsis thaliana* farnesyl diphosphate synthase precursor (FPS1) mRNA, complete cds<br>X76026, *K. lactis* FPS gene for farnesyl diphosphate synthetase, QCR8 gene for bc1 complex, subunit VIII<br>X82542, *P. argentatum* mRNA for farnesyl diphosphate synthase (FPS1),<br>X82543, *P. argentatum* mRNA for farnesyl diphosphate synthase (FPS2).<br>BC010004, *Homo sapiens*, farnesyl diphosphate synthase (farnesyl pyrophosphate synthetase, dimethylallyltransferase, geranyl-transtransferase), clone MGC 15352 IMAGE, 4132071, mRNA, complete cds<br>AF234168, *Dictyostelium discoideum* farnesyl diphosphate synthase (Dfps)<br>L46349, *Arabidopsis thaliana* farnesyl diphosphate synthase (FPS2) mRNA, complete cds<br>L46350, *Arabidopsis thaliana* farnesyl diphosphate synthase (FPS2) gene, complete cds<br>L46367, *Arabidopsis thaliana* farnesyl diphosphate synthase (FPS1) gene, alternative products, complete cds<br>M89945, Rat farnesyl diphosphate synthasegene, exons 1-8<br>NM_002004, *Homo sapiens* farnesyl diphosphate synthase (farnesyl pyrophosphate synthetase, dimethyl-allyltranstransferase, geranyltrans-transferase) (FDPS), mRNA<br>U36376, *Artemisia annua* farnesyl diphosphate synthase (fps1) mRNA, complete cds |

TABLE 1-continued

Sources of Genes Encoding the Upper Isoprene Pathway

| Gene | GenBank ® Accession Number and Source Organism |
| --- | --- |
| | XM_001352, *Homo sapiens* farnesyl diphosphate synthase (farnesyl pyrophosphate synthetase, dimethyl-allyltranstransferase, geranyltrans-transferase) (FDPS), mRNA |
| | XM_034497, *Homo sapiens* farnesyl diphosphate synthase (farnesyl pyrophosphate synthetase, dimethyl-allyltranstransferase, geranyltrans-transferase) (FDPS), mRNA |
| | XM_034498, *Homo sapiens* farnesyl diphosphate synthase (farnesyl pyrophosphate synthetase, dimethyl-allyltranstransferase, geranyltrans-transferase) (FDPS), mRNA |
| | XM_034499, *Homo sapiens* farnesyl diphosphate synthase (farnesyl pyrophosphate synthetase, dimethyl-allyltranstransferase, geranyltrans-transferase) (FDPS), mRNA |
| | XM_0345002, *Homo sapiens* farnesyl diphosphate synthase (farnesyl pyrophosphate synthetase, dimethyl-allyltranstransferase, geranyltrans-transferase) (FDPS), mRNA |

The Lower Carotenoid Biosynthetic Pathway

The division between the upper isoprenoid pathway and the lower carotenoid pathway is somewhat subjective. Because FPP synthesis is common in both carotenogenic and non-carotenogenic bacteria, the first step in the lower carotenoid biosynthetic pathway is considered to begin with the prenyltransferase reaction converting farnesyl pyrophosphate (FPP) to geranylgeranyl pyrophosphate (GGPP). The gene crtE, encoding GGPP synthetase, is responsible for this prenyltransferase reaction which adds IPP to FPP to produce the 20-carbon molecule GGPP. A condensation reaction of two molecules of GGPP occurs to form phytoene (PPPP), the first 40-carbon molecule of the lower carotenoid biosynthesis pathway. This enzymatic reaction is catalyzed by crtB, encoding phytoene synthase.

Lycopene, which imparts a "red" colored spectra, is produced from phytoene through four sequential dehydrogenation reactions by the removal of eight atoms of hydrogen, catalyzed by the gene crtI (encoding phytoene desaturase). Intermediaries in this reaction are phytofluene, zeta-carotene, and neurosporene.

Lycopene cyclase (crtY) converts lycopene to β-carotene. In the present invention, a reporter plasmid is used which produces β-carotene as the genetic end product. However, additional genes may be used to create a variety of other carotenoids. For example, β-carotene is converted to zeaxanthin via a hydroxylation reaction resulting from the activity of β-carotene hydroxylase (encoded by the crtZ gene). β-cryptoxanthin is an intermediate in this reaction.

β-carotene is converted to canthaxanthin by β-carotene ketolase encoded by either the crtW or crtO gene. Echinenone in an intermediate in this reaction. Canthaxanthin can then be converted to astaxanthin by β-carotene hydroxylase encoded by the crtZ or crtR gene. Adonbirubrin is an intermediate in this reaction.

Zeaxanthin can be converted to zeaxanthin-β-diglucoside. This reaction is catalyzed by zeaxanthin glucosyl transferase (crtX).

Genes encoding elements of the lower carotenoid biosynthetic pathway are known from a variety of plant, animal, and bacterial sources, as shown in Table 2.

TABLE 2

Sources of Genes Encoding the Lower Carotenoid Biosynthetic Pathway

| Gene | GenBank Accession Number and Source Organism |
| --- | --- |
| crtE (GGPP Synthase) | AB000835, *Arabidopsis thaliana* |
| | AB016043 and AB019036, *Homo sapiens* |
| | AB016044, *Mus musculus* |
| | AB027705 and AB027706, *Daucus carota* |
| | AB034249, *Croton sublyratus* |
| | AB034250, *Scoparia dulcis* |
| | AF020041, *Helianthus annuus* |
| | AF049658, *Drosophila melanogaster* signal recognition particle 19 kDa protein (srp19) gene, partial sequence; and geranylgeranyl pyrophosphate synthase (*quemao*) gene, complete cds |
| | AF049659, *Drosophila melanogaster* geranylgeranyl pyrophosphate synthase mRNA, complete cds |
| | AF139916, *Brevibacterium linens* |
| | AF279807, *Penicillium paxilli* geranylgeranyl pyrophosphate synthase (ggs1) gene, complete |
| | AF279808, *Penicillium paxilli* dimethylallyl tryptophan synthase (paxD) gene, partial cds; and cytochrome P450 monooxygenase (paxQ), cytochrome P450 monooxygenase (paxP), PaxC (paxC), monooxygenase (paxM), geranylgeranyl pyrophosphate synthase (paxG), PaxU (paxU), and metabolite transporter (paxT) genes, complete cds |
| | AJ010302, *Rhodobacter sphaeroides* |
| | AJ133724, *Mycobacterium aurum* |
| | AJ276129, *Mucor circinelloides f. lusitanicus* carG gene for geranylgeranyl pyrophosphate synthase, exons 1–6 |
| | D85029, *Arabidopsis thaliana* mRNA for geranylgeranyl pyrophosphate synthase, partial cds |
| | L25813, *Arabidopsis thaliana* |
| | L37405, *Streptomyces griseus* geranylgeranyl pyrophosphate synthase (crtB), phytoene desaturase (crtE) and phytoene synthase (crtI) genes, complete cds |
| | U15778, *Lupinus albus* geranylgeranyl pyrophosphate synthase (ggps1) mRNA, complete cds |
| | U44876, *Arabidopsis thaliana* pregeranylgeranyl pyrophosphate synthase (GGPS2) mRNA, complete cds |
| | X92893, *C. roseus* |
| | X95596, *S. griseus* |
| | X98795, *S. alba* |
| | Y15112, *Paracoccus marcusii* |
| crtX (Zeaxanthin glucosylase) | D90087, *E. uredovora* |
| | M87280 and M90698, *Pantoea agglomerans* |
| crtY (Lycopene-β-cyclase) | AF139916, *Brevibacterium linens* |
| | AF152246, *Citrus x paradisi* |
| | AF218415, *Bradyrhizobium* sp. ORS278 |
| | AF272737, *Streptomyces griseus* strain IFO13350 |
| | AJ133724, *Mycobacterium aurum* |
| | AJ250827, *Rhizomucor circinelloides f. lusitanicus* carRP gene for lycopene cyclase/phytoene synthase, exons 1–2 |
| | AJ276965, *Phycomyces blakesleeanus* carRA gene for phytoene synthase/lycopene cyclase, exons 1–2 |
| | D58420, *Agrobacterium aurantiacum* |
| | D83513, *Erythrobacter longus* |
| | L40176, *Arabidopsis thaliana* lycopene cyclase (LYC) mRNA, complete cds |
| | M87280, *Pantoea agglomerans* |
| | U50738, *Arabodopsis thaliana* lycopene epsilon |

TABLE 2-continued

Sources of Genes Encoding the Lower Carotenoid Biosynthetic Pathway

| Gene | GenBank Accession Number and Source Organism |
|---|---|
| | cyclase mRNA, complete cds |
| | U50739, *Arabidosis thaliana* lycopene β cyclase mRNA, complete cds |
| | U62808, *Flavobacterium* ATCC21588 |
| | X74599, *Synechococcus* sp. lcy gene for lycopene cyclase |
| | X81787, *N. tabacum* CrtL-1 gene encoding lycopene cyclase |
| | X86221, *C. annuum* |
| | X86452, *L. esculentum* mRNA for lycopene β-cyclase |
| | X95596, *S. griseus* |
| | X98796, *N. pseudonarcissus* |
| crtI (Phytoene desaturase) | AB046992, *Citrus unshiu* CitPDS1 mRNA for phytoene desaturase, complete cds |
| | AF039585, *Zea mays* phytoene desaturase (pds 1) gene promoter region and exon 1 |
| | AF049356, *Oryza sativa* phytoene desaturase precursor (Pds) mRNA, complete cds |
| | AF139916, *Brevibacterium linens* |
| | AF218415, *Bradyrhizobium* sp. ORS278 |
| | AF251014, *Tagetes erecta* |
| | AF364515, *Citrus x paradisi* |
| | D58420, *Agrobacterium aurantiacum* |
| | D83514, *Erythrobacter longus* |
| | L16237, *Arabidopsis thaliana* |
| | L37405, *Streptomyces griseus* geranylgeranyl pyrophosphate synthase (crtB), phytoene desaturase (crtE) and phytoene synthase (crtI) genes, complete cds |
| | L39266, *Zea mays* phytoene desaturase (Pds) mRNA, complete cds |
| | M64704; Soybean phytoene desaturase |
| | M88683, *Lycopersicon esculentum* phytoene desaturase (pds) mRNA, complete cds |
| | S71770, carotenoid gene cluster |
| | U37285, *Zea mays* |
| | U46919, *Solanum lycopersicum* phytoene desaturase (Pds) gene, partial cds |
| | U62808, *Flavobacterium* ATCC21588 |
| | X55289, *Synechococcus* pds gene for phytoene desaturase |
| | X59948, *L. esculentum* |
| | X62574, *Synechocystis* sp. pds gene for phytoene desaturase |
| | X68058, *C. annuum* pds1 mRNA for phytoene desaturase |
| | X71023, *Lycopersicon esculentum* pds gene for phytoene desaturase |
| | X78271, *L. esculentum* (Ailsa Craig) PDS gene |
| | X78434, *P. blakesleeanus* (NRRL1555) carB gene |
| | X78815, *N. pseudonarcissus* |
| | X86783, *H. pluvialis* |
| | Y14807, *Dunaliella bardawil* |
| | Y15007, *Xanthophyllomyces dendrorhous* |
| | Y15112, *Paracoccus marcusii* |
| | Y15114, *Anabaena* PCC7210 crtP gene |
| | Z11165, *R. capsulatus* |
| crtB (Phytoene synthase) | AB001284, *Spirulina platensis* |
| | AB032797, *Daucus carota* PSY mRNA for phytoene synthase, complete cds |
| | AB034704, *Rubrivivax gelatinosus* |
| | AB037975, *Citrus unshiu* |
| | AF009954, *Arabidopsis thaliana* phytoene synthase (PSY) gene, complete cds |
| | AF139916, *Brevibacterium linens* |
| | AF152892, *Citrus x paradisi* |
| | AF218415, *Bradyrhizobium* sp. ORS278 |
| | AF220218, *Citrus unshiu* phytoene synthase (Psy1) mRNA, complete cds |
| | AJ010302, *Rhodobacter* |
| | AJ133724, *Mycobacterium aurum* |
| | AJ278287, *Phycomyces blakesleeanus* carRA |
| | gene for lycopene cyclase/phytoene synthase, |
| | AJ304825, *Helianthus annuus* mRNA for phytoene synthase (psy gene) |
| | AJ308385, *Helianthus annuus* mRNA for phytoene synthase (psy gene) |
| | D58420, *Agrobacterium aurantiacum* |
| | L23424, *Lycopersicon esculentum* phytoene synthase (PSY2) mRNA, complete cds |
| | L25812, *Arabidopsis thaliana* |
| | L37405, *Streptomyces griseus* geranylgeranyl pyrophosphate synthase (crtB), phytoene desaturase (crtE) and phytoene synthase (crtI) genes, complete cds |
| | M38424, *Pantoea agglomerans* phytoene synthase (crtE) gene, complete cds |
| | M87280, *Pantoea agglomerans* |
| | S71770, Carotenoid gene cluster |
| | U32636, *Zea mays* phytoene synthase (Y1) gene, complete cds |
| | U62808, *Flavobacterium* ATCC21588 |
| | U87626, *Rubrivivax gelatinosus* |
| | U91900, *Dunaliella bardawil* |
| | X52291, *Rhodobacter capsulatus* |
| | X60441, *L. esculentum* GTom5 gene for phytoene synthase |
| | X63873, *Synechococcus* PCC7942 pys gene for phytoene synthase |
| | X68017, *C. annuum* psy1 mRNA for phytoene synthase |
| | X69172, *Synechocystis* sp. pys gene for phytoene synthase |
| | X78814, *N. pseudonarcissus* |
| crtZ (β-carotene hydroxylase) | D58420, *Agrobacterium aurantiacum* |
| | D58422, *Alcaligenes* sp. |
| | D90087, *E. uredovora* |
| | M87280, *Pantoea agglomerans* |
| | U62808, *Flavobacterium* ATCC21588 |
| | Y15112, *Paracoccus marcusii* |
| crtW (β-carotene ketolase) | AF218415, *Bradyrhizobium* sp. ORS278 |
| | D45881, *Haematococcus pluvialis* |
| | D58420, *Agrobacterium aurantiacum* |
| | D58422, *Alcaligenes* sp. |
| | X86782, *H. pluvialis* |
| | Y15112, *Paracoccus marcusii* |

Preferred sources of the non-crtW carotenoid genes are from *Pantoea stewartii* (ATCC 8199; WO 02/079395), *Enterobactericeae* DC260 (U.S. Ser. No. 10/808,979), and *Pantoea agglomerans* DC404 (U.S. Ser. No. 10/808,807). Preferred sources of crtW genes are from *Sphingomonas melonis* DC18 (SEQ ID NO:1), *Brevundimonas vesicularis* DC263 (SEQ ID NO:3), and *Flavobacterium* sp. K1-202C (SEQ ID NO:5).

By using various combinations of the genes presented in Table 2 and the preferred crtW genes of the present invention, numerous different carotenoids and carotenoid derivatives could be made using the methods of the present invention, provided that sufficient sources of FPP are available in the host organism. For example, the gene cluster crtEXYIB enables the production of β-carotene. The addition of the crtW gene to crtEXYIB enables the production of canthaxanthin.

It is envisioned that useful products of the present invention will include any ketocarotenoid compound as defined herein including, but not limited to antheraxanthin, adonixanthin, astaxanthin, canthaxanthin, β-cryptoxanthin, keto-γ- carotene, echinenone, 3-hydroxyechinenone, 3'-hydroxyechinenone, and $C_{30}$-ketocarotenoids.

Recombinant Expression—Microbial

The gene and gene product of the instant sequences may be produced in heterologous host cells, particularly in the cells of microbial hosts. Expression in recombinant microbial hosts may be useful for the expression of various pathway intermediates, for the modulation of pathways already existing in the host, or for the synthesis of new products heretofore not possible using the host.

Preferred heterologous host cells for expression of the instant genes and nucleic acid fragments are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid fragments. Because of transcription, translation and the protein biosynthetic apparatus is the same irrespective of the cellular feed stock, functional genes are expressed irrespective of carbon feedstock used to generate cellular biomass. Large-scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to bacterial, fungal or yeast species such as *Aspergillus, Trichoderma, Saccharomyces, Pichia, Candida, Hansenula*, or bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, suitable bacterial host strains include *Escherichia, Bacillus*, and *Methylomonas*.

Microbial expression systems and expression vectors containing regulatory sequences that direct high level expression of foreign proteins are well known to those skilled in the art. Any of these could be used to construct chimeric genes for expression of present ketolases. These chimeric genes could then be introduced into appropriate microorganisms via transformation to provide high level expression of the enzymes Accordingly, it is expected that introduction of chimeric genes encoding the instant bacterial enzymes under the control of the appropriate promoters will demonstrate increased or altered cyclic ketocarotenoid production. It is contemplated that it will be useful to express the instant genes both in natural host cells as well as heterologous host. Introduction of the present crtW genes into native host will result in altered levels of existing ketocarotenoid production. Additionally, the instant genes may also be introduced into non-native host bacteria where the existing carotenoid pathway may be manipulated.

Specific ketocarotenoids that will be produced by the present invention include, but are not limited to canthaxanthin, astaxanthin, adonixanthin, adonirubin, echinenone, 3-hydroxyechinenone, 3'-hydroxyechinenone, 4-keto-gamma-carotene, 4-keto-rubixanthin, 4-keto-torulene, 3-hydroxy-4-keto-torulene, deoxyflexixanthin, and myxobactone. Of particular interest is the production of astaxanthin and canthaxanthin, the synthesis of which is shown in FIG. 1. The specific substrate for the present CrtW enzymes is a cyclic carotenoid. Cyclic carotenoids are well known in the art and available commercially. Preferred in the present invention are CrtW ketolase substrates that include, but are not limited to β-carotene, γ-carotene, zeaxanthin, β-cryptoxanthin, 3'-hydroxyechinenone, rubixanthin, echinenone, and torulene.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*, and promoters isolated from the nrtA, glnB, moxF, glyoxll, htpG, and hps genes useful for expression in *Methylomonas* (U.S. Ser. No. 10/689,200). Additionally, promoters such as the chloramphenicol resistance gene promoter may also be useful for expression in *Methylomonas*.

Termination control regions may also be derived from various genes native to the preferred hosts. Optionally, a termination site may be unnecessary, however, it is most preferred if included.

Knowledge of the sequence of the present gene will be useful in manipulating the carotenoid biosynthetic pathways in any organism having such a pathway and particularly in *Methylomonas* sp. 16a and *Escherichia coli*. Methods of manipulating genetic pathways are common and well known in the art. Selected genes in a particularly pathway may be upregulated or down regulated by variety of methods. Additionally, competing pathways organism may be eliminated or sublimated by gene disruption and similar techniques.

Once a key genetic pathway has been identified and sequenced specific genes may be upregulated to increase the output of the pathway. For example, additional copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565,350; Zarling et al., PCT/US93/03868).

Alternatively it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al., *J. Bacteriol.*, 171:4617-4622 (1989), Balbas et al., *Gene*, 136:211-213 (1993), Gueldener et al., *Nucleic Acids Res.*, 24:2519-2524 (1996), and Smith et al., *Methods Mol. Cell. Biol.*, 5:270-277 (1996)).

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992).

Another non-specific method of gene disruption is the use of transposable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

Methylotrophs and *Methylomonas* sp. 16a as Microbial Hosts

Although a number of carotenoids have been produced from recombinant microbial sources [e.g., *E. coli* and *Candida utilis* for production of lycopene (Farmer W. R. and J. C. Liao, *Biotechnol. Prog.*, 17: 57-61 (2001); Wang C. et al., *Biotechnol Prog.*, 16: 922-926 (2000); Misawa, N. and H. Shimada, *J. Biotechnol.*, 59: 169-181 (1998); Shimada, H., et al., *Appl. Environm. Microbiol.*, 64:2676-2680 (1998)); *E. coli, Candida utilis* and *Pfaffia rhodozyma* for production of β-carotene (Albrecht, M. et al., *Biotechnol. Lett.*, 21: 791-795 (1999); Miura, Y. et al., *Appl. Environm. Microbiol.*, 64:1226-1229 (1998); U.S. Pat. No. 5,691,190); *E. coli* and *Candida utilis* for production of zeaxanthin (Albrecht, M. et al., supra; Miura, Y. et al., supra); *E. coli* and *Pfaffia rhodozyma* for production of astaxanthin (U.S. Pat. No. 5,466,599; U.S. Pat. No. 6,015,684; U.S. Pat. No. 5,182,208; U.S. Pat. No. 5,972,642); see also: U.S. Pat. No. 5,656,472, U.S. Pat. No. 5,545,816, U.S. Pat. No. 5,530,189, U.S. Pat. No. 5,530,188, U.S. Pat. No. 5,429,939, and U.S. Pat. No. 6,124,113), these methods of producing carotenoids using various combinations of different crt genes suffer from low yields and reliance on relatively expensive feedstocks. Thus, it would be desirable to identify a method that produces higher yields of carotenoids in a microbial host from an inexpensive feedstock. There are a number of microorganisms that utilize single carbon substrates as their sole energy source. Such microorganisms are referred to herein as "C1 metabolizers". These organisms are characterized by the ability to use carbon substrates lacking carbon to carbon bonds as a sole source of energy and biomass. These carbon substrates include, but are not limited to: methane, methanol, formate, formaldehyde, formic acid, methylated amines (e.g., mono-, di- and tri-methyl amine), methylated thiols, carbon dioxide, and various other reduced carbon compounds which lack any carbon-carbon bonds. In one embodiment, the single carbon substrate is selected from the group consisting of methane and methanol. All C1 metabolizing microorganisms are generally classified as methylotrophs. Methylotrophs may be defined as any organism capable of oxidizing organic compounds that do not contain carbon-carbon bonds. However, facultative methylotrophs, obligate methylotrophs, and obligate methanotrophs are all various subsets of methylotrophs. Specifically:

Facultative methylotrophs have the ability to oxidize organic compounds which do not contain carbon-carbon bonds, but may also use other carbon substrates such as sugars and complex carbohydrates for energy and biomass. Facultative methylotrophic bacteria are found in many environments, but are isolated most commonly from soil, landfill and waste treatment sites. Many facultative methylotrophs are members of the β and γ subgroups of the Proteobacteria (Hanson et al., *Microb. Growth C1 Compounds.*, [Int. Symp.], 7$^{th}$ (1993), pp 285-302 Murrell, J. Collin and Don P. Kelly, Eds. Intercept: Andover, UK; Madigan et al., *Brock Biology of Microorganisms*, 8$^{th}$ ed., Prentice Hall: UpperSaddle River, N.J. (1997)).

Obligate methylotrophs are those organisms that are limited to the use of organic compounds that do not contain carbon-carbon bonds for the generation of energy.

Obligate methanotrophs are those obligate methylotrophs that have the distinct ability to oxidize methane.

Additionally, the ability to utilize single carbon substrates is not limited to bacteria but extends also to yeasts and fungi. A number of yeast genera are able to use single carbon substrates as energy sources in addition to more complex materials (i.e., the methylotrophic yeasts).

Although a large number of these methylotrophic organisms are known, few of these microbes have been successfully harnessed in industrial processes for the synthesis of materials. And, although single carbon substrates are cost-effective energy sources, difficulty in genetic manipulation of these microorganisms as well as a dearth of information about their genetic machinery has limited their use primarily to the synthesis of native products.

Despite these hardships, many methanotrophs contain an inherent isoprenoid pathway that enables these organisms to synthesize pigments and provides the potential for one to envision engineering these microorganisms for production of various non-endogenous isoprenoid compounds. Since methanotrophs can use single carbon substrates (i.e., methane and/or methanol) as an energy source, it could be possible to produce carotenoids at low cost in these organisms. One such example wherein a methanotroph is engineered for production of β-carotene is described in U.S. Ser. No. 09/941,947, hereby incorporated by reference.

Methods are provided for the expression of genes involved in the biosynthesis of carotenoid compounds in microorganisms that are able to use single carbon substrates as a sole energy source. The host microorganism may be any C1 metabolizer that has the ability to synthesize farnesyl pyrophosphate (FPP) as a metabolic precursor for carotenoids. More specifically, facultative methylotrophic bacteria suitable in the present invention include, but are not limited to *Methylophilus, Methylobacillus, Methylobacterium, Hyphomicrobium, Xanthobacter, Bacillus, Paracoccus, Nocardia, Arthrobacter, Rhodopseudomonas*, and *Pseudomonas*. Specific methylotrophic yeasts useful in the present invention include, but are not limited to: *Candida, Hansenula, Pichia, Torulopsis*, and *Rhodotorula*. Exemplary methanotrophs include, but are not limited to the genera *Methylomonas, Methylobacter, Methylococcus, Methylosinus, Methylocyctis, Methylomicrobium*, and *Methanomonas*.

Of particular interest in the present invention are high growth obligate methanotrophs having an energetically favorable carbon flux pathway. For example, a specific strain of methanotroph having several pathway features that makes it particularly useful for carbon flux manipulation. This strain is known as *Methylomonas* 16a (ATCC PTA 2402) (U.S. Pat. No. 6,689,601); and, this particular strain and other related methylotrophs are preferred microbial hosts for expression of the gene products of this invention, useful for the production of $C_{40}$ carotenoids.

An optimized version of *Methylomonas* sp. 16a has been created and designated as *Methylomonas* sp. 16a MWM1200 (U.S. Ser. No. 60/527,083). The endogenous $C_{30}$ carotenoid pathway has been knocked-out (Δcrt cluster promoter+ΔcrtN3), creating an optimized platform for $C_{40}$ carotenoid production. The deletion of the promoter responsible for expression of the endogenous crt cluster (crtN1-ald-crtN2 cluster) resulted in a non-pigmented strain (the wild type strain in normally pink in color due to its naturally production of $C_{30}$ carotenoids). Expression of $C_{40}$ carotenoid biosynthesis genes within this optimized host enables increased production of the desired $C_{40}$ carotenoids.

Transformation of C1 Metabolizing Bacteria

Techniques for the transformation of C1 metabolizing bacteria are not well developed, although general methodology that is utilized for other bacteria, which is well known to those of skill in the art, may be applied. Electroporation has been used successfully for the transformation of: *Methylobacterium extorquens* AM1 (Toyama, H., et al., *FEMS Microbiol. Lett.*, 166:1-7 (1998)), *Methylophilus methylotrophus* AS1 (Kim, C. S., and T. K. Wood, *Appl. Microbiol. Biotechnol.*, 48: 105-108 (1997)), and *Methylobacillus* sp. strain 12S (Yoshida, T., et al., *Biotechnol. Lett.*, 23: 787-791 (2001)). Extrapolation of specific electroporation parameters from one specific C1 metabolizing utilizing organism to another may be difficult, however, as is well to known to those of skill in the art.

Bacterial conjugation, relying on the direct contact of donor and recipient cells, is frequently more readily amenable for the transfer of genes into C1 metabolizing bacteria. Simplistically, this bacterial conjugation process involves mixing together "donor" and "recipient" cells in close contact with one another. Conjugation occurs by formation of cytoplasmic connections between donor and recipient bacteria, with direct transfer of newly synthesized donor DNA into the recipient cells. As is well known in the art, the recipient in a conjugation is defined as any cell that can accept DNA through horizontal transfer from a donor bacterium. The donor in conjugative transfer is a bacterium that contains a conjugative plasmid, conjugative transposon, or mobilizable plasmid. The physical transfer of the donor plasmid can occur in one of two fashions, as described below:

1. In some cases, only a donor and recipient are required for conjugation. This occurs when the plasmid to be transferred is a self-transmissible plasmid that is both conjugative and mobilizable (i.e., carrying both tra genes and genes encoding the Mob proteins). In general, the process involves the following steps: 1.) Double-strand plasmid DNA is nicked at a specific site in oriT; 2.) A single-strand DNA is released to the recipient through a pore or pilus structure; 3.) A DNA relaxase enzyme cleaves the double-strand DNA at oriT and binds to a release 5' end (forming a relaxosome as the intermediate structure); and 4.) Subsequently, a complex of auxiliary proteins assemble at oriT to facilitate the process of DNA transfer.

2. Alternatively, a "triparental" conjugation is required for transfer of the donor plasmid to the recipient. In this type of conjugation, donor cells, recipient cells, and a "helper" plasmid participate. The donor cells carry a mobilizable plasmid or conjugative transposon. Mobilizable vectors contain an oriT, a gene encoding a nickase, and have genes encoding the Mob proteins; however, the Mob proteins alone are not sufficient to achieve the transfer of the genome. Thus, mobilizable plasmids are not able to promote their own transfer unless an appropriate conjugation system is provided by a helper plasmid (located within the donor or within a "helper" cell). The conjugative plasmid is needed for the formation of the mating pair and DNA transfer, since the plasmid encodes proteins for transfer (Tra) that are involved in the formation of the pore or pilus.

Examples of successful conjugations involving C1 metabolizing bacteria include the work of: Stolyar et al. (*Mikrobiologiya*, 64(5): 686-691 (1995)); Motoyama, H. et al. (*Appl. Micro. Biotech.*, 42(1): 67-72 (1994)); Lloyd, J. S. et al. (*Archives of Microbiology*, 171(6): 364-370 (1999)); and Odom, J. M. et al. (U.S. Ser. No. 09/941,947).

Industrial Production

Where commercial production of cyclic ketocarotenoid compounds is desired using the present crtW genes, a variety of culture methodologies may be applied. For example, large-scale production of a specific gene product overexpressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the fed-batch system. Fed-batch culture processes are also suitable in the present invention and comprise a typical batch system with the exception that the substrate is added in increments as the culture progresses. Fed-batch systems are useful when catabolite repression is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36:227, (1992).

Commercial production of cyclic ketocarotenoids may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, methane, and/or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.*, 153:485-489 (1990)). Hence it is contemplated that the source of carbon utilized in the present invention may encompass a wide variety of carbon containing substrates and will only be limited by the choice of organism.

Recombinant Expression—Plants

Plants and algae are also known to produce carotenoid compounds. The nucleic acid fragments of the instant invention may be used to create transgenic plants having the ability to express the microbial protein. Preferred plant hosts will be any variety that will support a high production level of the instant proteins. Suitable green plants will include, but are not limited to soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa*, L), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include, but not limited to commercially significant hosts such as *Spirulina, Haemotacoccus*, and *Dunalliela*. Production of the carotenoid compounds may be accomplished by first constructing chimeric genes of present invention in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences or the present invention should be capable of promoting expression of the present gene product. High-level plant promoters that may be used in this invention include the promoter of the small subunit (ss) of the ribulose-1,5-bisphosphate carboxylase from example from soybean (Berry-Lowe et al., *J. Molecular and App. Gen.*, 1:483-498 1982)), and the promoter of the chlorophyll a/b binding protein. These two promoters are known to be light-induced in plant cells (see, for example, *Genetic Engineering of Plants, an Agricultural Perspective*, A. Cashmore, Plenum, N.Y. (1983), pages 29-38; Coruzzi, G. et al., *J. Biol. Chem.*, 258:1399 (1983), and Dunsmuir, P. et al., *J. Mol. Appl. Gen.*, 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.*, 4:2411-2418 (1985); De Almeida et al., *Mol. Gen. Genetics*, 218:78-86 (1989)), and thus that multiple events must be screened in order to obtain lines displaying the desired expression level and pattern. Such screening may be accomplished by Southern analysis of DNA blots (Southern, *J. Mol. Biol.*, 98:503 (1975)). Northern analysis of mRNA expression (Kroczek, *J. Chromatogr. Biomed. Appl.*, 618 (1-2):133-145 (1993)), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell*, 56:247-253 (1989)), signal sequences or sequences encoding endoplasmic reticulum localization (Chrispeels, J. J., *Ann. Rev. Plant Phys. Plant Mol. Biol.*, 42:21-53 (1991)), or nuclear localization signals (Raikhel, N., *Plant Phys.*, 100:1627-1632 (1992)) added and/or with targeting sequences that are already present removed. While the references cited give examples of each of these, the list is not exhaustive and more targeting signals of utility may be discovered in the future that are useful in the invention.

Protein Engineering

It is contemplated that the present nucleotides may be used to produce gene products having enhanced or altered activity. Various methods are known for mutating a native gene sequence to produce a gene product with altered or enhanced activity including but not limited to error-prone PCR (Melnikov et al., *Nucleic Acids Research*, 27(4):1056-1062 (1999); site-directed mutagenesis (Coombs et al., *Proteins* (1998), 259-311, 1 plate. Editor(s): Angeletti, Ruth Hogue. Publisher: Academic, San Diego, Calif.); "gene shuffling" (U.S. Pat. No. 5,605,793; U.S. Pat. No. 5,811,238; U.S. Pat. No. 5,830,721; U.S. Pat. No. 5,837,458; and U.S. Ser. No. 10/374,366, hereby incorporated by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The instant microbial sequences of the present invention may be mutated and screened for altered or enhanced activity by this method. The sequences should be double stranded and can be of various lengths ranging form 50 bp to 10 kb. The sequences may be randomly digested into fragments ranging from about 10 bp to 1000 bp, using restriction endonucleases well known in the art (Maniatis, supra). In addition to the instant microbial sequences, populations of fragments that are hybridizable to all or portions of the microbial sequence may be added. Similarly, a population of fragments that are not hybridizable to the instant sequence may also be added. Typically these additional fragment populations are added in about 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTP's (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide ranging from about 50 bp to about 100 kb and may be screened for expression and altered activity by standard cloning and expression protocol. (Maniatis, supra).

Furthermore, a hybrid protein can be assembled by fusion of functional domains using the gene shuffling (exon shuffling) method (Nixon et al., *PNAS*, 94:1069-1073 (1997)). The functional domain of the instant gene can be combined with the functional domain of other genes to create novel enzymes with desired catalytic function. A hybrid enzyme may be constructed using PCR overlap extension method and cloned into the various expression vectors using the techniques well known to those skilled in art.

DESCRIPTION OF THE PREFERRED EMBODIMENTS

Pigmented microbes were isolated from environmental samples and cultured using standard microbiological techniques (Example 1). Two pigmented colonies (DC18 and DC263) were selected and 16S rRNA gene sequencing was performed. The 16S rRNA gene sequence from strain DC18 (SEQ ID NO. 4) was used as a query search using BLASTN against GenBank®. The closest match to the public database was 98% identical to *Sphingomonas melonis*. The strain was designated as *Sphingomonas melonis* DC18. The 16S rRNA gene sequence from strain DC263 (SEQ ID NO. 5) exhibited homology (99% identical) to *Brevundimonas vesicularis*. The isolated strain was designated as *Brevundimonas vesicularis* DC263. A third pigmented microbial strain (*Flavobacterium* sp. K1-202C) was obtained from Dr. Gerhard Sandmann (J.W. Goethe University, Germany). This strain is also known as *Cytophaga* sp. KK1020C and is available from the Marine Biotechnology Institute (MBI, Japan).

Carotenoid samples from each strain were analyzed by HPLC/LC-MS. The major carotenoid in *Sphingomonas melonis* DC18 was determined to be tetrahydroxy-β,β'-caroten-4-one. The major carotenoid in *Brevundimonas vesicularis* DC263 was determined to be tetrahydroxy-β,β'-caroten-4,4'-dione. The major carotenoid in *Flavobacterium* sp. K1-202C was flexixanthin. The major carotenoids in all three strains were ketocarotenoids, indicating that they all possessed a carotenoid ketolase.

Genomic DNA was prepared from each strain for the creation of small insert libraries (4-6 kb fragments) in pEZseq vector (Example 2). The respective plasmids were electroporated into *E. coli* cells harboring a β-carotene producing plasmid. Orange pigmented transformants were isolated and the respective carotenoid content of each was analyzed. Ketocarotenoids were produced by each orange transformant.

The inserts on the pEZ-based plasmid were sequenced by random transposon insertion and/or by primer walking. Sequences of the inserts were assembled and BLAST analyzed (BLASTNnr and BLASTXnr) against GenBank®. The genes encoding the CrtW ketolases were identified (Example 3, Table 3). Pairwise comparison analysis was conducted using the present crtW sequences and several previously reported crtWs (Table 4). The present crtW sequences show only moderate homology to previously reported carotenoid ketolases.

The present carotenoid ketolase genes were cloned individually into a pTrcHis2-TOPO expression vector (Example 5). Each crtW expression vector was transformed into a β-carotene accumulating *E. coli* strain. The carotene content of the respective orange transformants was analyzed by HPLC. Canthaxanthin was exclusively produced in each of the respective transformants.

Several β-carotene expression plasmids (pDCQ340, pDCQ330) were created to measure the effects of expressing the present crtW ketolase genes (Examples 4 and 7). The expression plasmids were created by cloning the carotenoid gene clusters from either *Enterobactericeae* DC260 (U.S. Ser. No. 10/808,979) or *Pantoea agglomerans* DC404 (U.S. Ser. No. 10/808,807). The present CrtW ketolases exhibited the ability to convert β-carotene into canthaxanthin.

In another embodiment, coexpression of divergent ketolase was conducted (Example 6). The plasmid expressing the β-carotene synthesis genes (pDCQ330) used in Example 5 was engineered to additionally express the crtWZ genes from *Agrobacterium aurantiacum*. The resulting plasmid (pDCQ335) was used to create an astaxanthin/adonixanthin producing *E. coli* strain. The plasmids expressing either the crtW from DC263 (pDCQ342TA) or the crtW from K1-202C (pDCQ339TA) were transformed into the astaxanthin/adonixanthin producing strain. Comparisons between the strain harboring pDCQ335 alone and the strains containing the additional plasmid pDCQ342TA or pDCQ339TA were conducted. Strains expressing one or more divergent ketolase genes improved the efficiency of keto group addition, increasing the production of astaxanthin.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories/BD Diagnostics (Sparks, Md.), Promega (Madison, Wis.), New England Biolabs (Beverly, Mass.), GIBCO/BRL Life Technologies (Carlsbad, Calif.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. Multiple alignments were created using the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.). In any case where program parameters were not prompted for, in these or any other programs, default values were used.

The meaning of abbreviations is as follows: "h" means hour(s), "min" means minute(s), "seq" means second(s), "d" means day(s), "mL" means milliliters, "μL" mean microliters, "L" means liters, "g" means grams, "mg" means milligrams, "μg" means micrograms, and "ppm" means parts per million.

Example 1

Bacterial Strains Producing Ketocarotenoids

This example describes isolation of three bacterial strains that produce ketocarotenoids and preliminary analysis of their carotenoids.

Strain Isolation and Typing

To isolate novel carotenoid producing bacterial strains pigmented microbes were isolated from a collection of environmental samples. Approximately 1 g of surface soil from a yard in Wilmington, Del. was resuspended in 10 mL of tap water. A 10-μL loopful of the water was streaked onto Luria-Broth (LB) plates and the plates were incubated at 30° C. Pigmented bacteria with diverse colony appearances were picked and streaked twice to homogeneity on LB plates and incubated at 30° C. From these colonies, one which formed orange-pink colonies was designated as strain DC263. Strain DC18 was isolated from a Pennsylvania stream. Serial dilutions ($10^{-2}$, $10^{-4}$ and $10^{-6}$) of the aqueous sample were plated onto large 245×245 mm 15% agar plates with basal medium enriched with tryptone and yeast. The components of the basal medium (per liter) were: $NH_4Cl$ 0.8 g, $KH_2PO_4$ 0.5 g, $MgCl_2$ $6H_2O$ 0.2 g, $CaCl_2$ $2H_2O$ 0.1 g, $NaNO_3$ 1.3 g, and $Na_2SO_4$ 0.5 g. The components of the stock solution 1 were (per liter): nitrilotriacetic acid 12.8 g, $FeCl_2.4H_2O$ 0.3 g, $CuCl_2.2H_2O$ 0.0254 g, $MnCl_2.4H_2O$ 0.1 g, $CoCl_2.6H_2O$ 0.312 g, $ZnCl_2$ 0.1 g, $H_3BO_3$ 0.01 g, $Na_2MoO_4.2H_2O$ 0.01 g, and $NiCl_2.6H_2O$ 0.184 g. Ten milliliters of stock solution 1 was added per 1 liter of the basal medium. The medium was supplemented with tryptone at concentration 10 g/L and yeast extract 5 g/L. Media pH was adjusted to 7. The plates were incubated at room temperature and single colonies were streaked twice onto the same plates. One strain was selected which formed orange colonies and was designated as strain DC18.

16S rRNA gene sequencing was performed with DC18 and DC263. Specifically, the 16S rRNA gene of the strain was amplified by PCR using primers HK12: 5'-GAGTTTGATCCTGGCTCAG-3' (SEQ ID NO:7) and JCR14: 5'-ACGGGCGGTGTGTAC-3' (SEQ ID NO:8). The amplified 16S rRNA genes were purified using a QIAquick PCR Purification Kit according to the manufacturer's instructions (Qiagen) and sequenced on an automated ABI sequencer. The sequencing reactions were initiated with primers HK12, JCR14, and JCR15: 5'-GCCAGCAGC-CGCGGTA-3' (SEQ ID NO:9). The assembled 1291 bp 16S rRNA gene sequence (SEQ ID NO:10) of DC18 and 1268 bp 16S rRNA gene sequence (SEQ ID NO:11) of DC263 were used as the query sequence for a BLASTN search (Altschul et al., *Nucleic Acids Res.*, 25:3389-3402(1997)) against GenBank®. The 16S rDNA sequence of DC18 showed homology to those of *Sphingomonas* strains, with the top hit as 98% identical to *Sphingomonas melonis*. This strain was thus designated as *Sphingomonas melonis* DC18. The 16S rDNA sequence of DC263 showed homology to those of *Brevundimonas* strains, with the top hit as 99% identical to *Brevundimonas vesicularis*. This strain was thus designated as *Brevundimonas vesicularis* DC263.

*Flavobacterium* sp. K1-202C was a marine isolate that we obtained from Dr. Gerhard Sandmann at J. W. Goethe University in Germany. *Flavobacterium* sp. K1-202C is also known as *Cytophaga* sp. KK10202C (MBIC0139), available from the Marine Biotechnology Institute (MBI) (Iwate, Japan).

Carotenoid Analysis

*Sphingomonas melonis* DC18 was grown in 100 mL of the same medium as described for the strain isolation. *Brevundimonas vesicularis* DC263 was grown in 100 mL LB. *Flavobacterium* sp. K1-202C was grown in 100-mL marine broth (Difco, Detroit, Mich.). All three strains were grown at 30° C. shaking overnight. Cells were pelleted by centrifugation at 4000 g for 15 min, and the cell pellets were extracted with 10 mL acetone. The extraction was dried under nitrogen and redissolved in 1-2 mL of acetone. The extraction was filtered with an Acrodisc® CR25 mm syringe filter (Pall Corporation, Ann Arbor, Mich.). It was then concentrated in 0.1 mL 10% acetone+90% acetonitrile for HPLC analysis using an Agilent Series 1100 LC/MSD SI (Agilent, Foster City, Calif.).

Samples (20 μL) were loaded onto a 150 mm×4.6 mm ZORBAX C18 (3.5 μm particles) column (Agilent Technologies, Inc.). The column temperature was kept at 40° C. The flow rate was 1 mL/min, while the solvent running program used was 0-2 min: 95% Buffer A and 5% Buffer B;
2-10 min: linear gradient from 95% Buffer A and 5% Buffer B to 60% Buffer A and 40% Buffer B;
10-12 min: linear gradient from 60% Buffer A and 40% Buffer B to 50% Buffer A and 50% Buffer B;
12-18 min: 50% Buffer A and 50% Buffer B; and,
18-20 min: 95% Buffer A and 5% Buffer B.

Buffer A was 95% acetonitrile and 5% $dH_2O$; Buffer B was 100% tetrahydrofuran.

FIGS. 2a, 2b, and 2c show the HPLC profiles of the carotenoids produced in DC18, DC263 and K1-202C. The absorption spectra of the major carotenoid were also shown for each strain. The molecular weight of the major carotenoid was determined by LC-MS. Each sample of 50 μL was run on a Zorbax 2.1×150 mm SB-C18 LC column (Agilent Technologies, CA) with solvent program of:

0-30 min: linear gradient from 70% acetonitrile and 30% water to 100% acetonitrile;
30-45 min: 100% acetonitrile.

The mass spectrometer (Micromass Quattro LC triple quadrapole, Micromass Limited, UK) was scanned from 100 to 1000 AMU's in 0.9 sec with an 0.1 sec interscan delay in APCI (Atmospheric Pressure Chemical Ionization) mode with the corona discharge needle at 3KV and the APCI probe at 450° C. LC-MS analyses determined the molecular weight of the major carotenoid in DC18 to be 614, the molecular weight of the major carotenoid in DC263 to be 628, and the molecular weight of the major carotenoid in K1-202C to be 582. Based on the HPLC elution time, the absorption spectra, and the molecular weight, the major carotenoid in DC18 was predicted to be tetrahydroxy-β,β'-caroten-4-one. The major carotenoid in DC263 was predicted to be tetrahydroxy-β,β'-caroten-4,4'-dione. The properties we determined for the major carotenoid in DC18 and DC263 were consistent with those reported in the literature for these carotenoids (Yokoyama et al., *Biosci. Biotech. Biochem.*, 60:200-203, (1996); Kleinig et al, *Helvetica Chimica Acta*, 60:254-258 (1977)). The major carotenoid in K1-202C was determined to be flexixanthin by Sandmann's group. The properties determined for the major carotenoid in K1-202C was consistent with those reported for flexixanthin (Aasen et al., *Acta Chemica Scandinavica*, 20:1970-1988 (1966); Andrewes et al., *Acta Chemica Scandinavica*, B38: 337-339 (1984)). These three strains are potential sources for carotenoid ketolase genes, since the major carotenoids in all three strains are ketocarotenoids.

Example 2

Construction and Screening of Small Insert Libraries

This example describes construction of the small insert library from the bacterial strains and identification of positive clones that potentially contain the ketolase gene.

Library Construction

Cells of DC18, DC263 and K1-202C were grown as described in Example 1. Genomic DNA was prepared from the cells using the Qiagen genomic DNA preparation kits. The small insert library of strain K1-202C was prepared by partial restriction digest method. Genomic DNA of K1-202C was partially digested with HincII (Promega, Madison, Wis.) and separated on a 0.8% agarose gel. The 4-6 kb fraction was excised from the gel and extracted using Qiagen MinElute Gel-Extraction kit. The extracted DNA was ligated to pEZseq vector using pEZSeq Blunt Cloning kit (Lucigen, Middletown, Wis.). The ligation mixture was electroporated into freshly prepared competent cells of *E. coli* 10G containing a β-carotene producing plasmid pBHR-crt1 (U.S. Ser. No. 09/941,947). Transformants were plated on LB plates with 100 μg/mL ampicillin and 50 μg/mL kanamycin.

The small insert library of strain DC18 and DC263 was prepared by random shearing method. Genomic DNA of DC18 and DC263 was sheared by passing through a 29 1/2 G insulin syringe (Becton Dickinson, Franklin Lakes, N.J.) about 300 times and separated on a 0.8% agarose gel. The 4-6 kb fraction was excised from the gel and extracted using Qiagen MinElute Gel-Extraction kit (Qiagen). The ends of the extracted DNA were repaired using Lucigen DNA Terminator Repair kit. The repaired DNA inserts were ligated to pEZseq vector using pEZSeq Blunt Cloning kit (Lucigen). The ligation mixture was electroporated into freshly prepared competent cells of *E. coli* 10G containing a β-carotene producing plasmid pDCQ329 (U.S. Ser. No. 10/808,979; hereby incorporated by reference). Transformants were plated on LB plates with 100 μg/mL ampicillin and 50 μg/mL kanamycin.

Identification and Analysis of Positive Clones

Approximately 20,000 to 100,000 transformants were obtained for each library. Several orange colonies were identified among the tens of thousands of yellow colonies for each library. These positive clones were identified as possibly containing a ketolase gene that converted β-carotene to ketocarotenoids. Each of the positive strains was grown in 100 mL LB with antibiotics at 30° C. shaking for 3 days. Carotenoids from the cells were extracted and analyzed by HPLC as described in Example 1. Ketocarotenoids (canthaxanthin and echinenone) were produced in the positive *E. coli* clones isolated from the library of DC18, DC263, and K1-202C.

Example 3

Isolation of Novel Carotenoid Ketolase Genes

This example describes sequencing of the insert on the positive *E. coli* clones and identification of novel carotenoid ketolase genes encoded on the inserts.

Carotenoid analysis indicated that the positive clones probably contained ketolase genes that are responsible for conversion of β-carotene to canthaxanthin and echinenone. The pEZ-based plasmid was separated from the β-carotene reporter plasmid by selecting for ampicillin resistant and kanamycin sensitive clones. The insert on the pEZ-based plasmid was sequenced by random transposon insertion using the EZ-TN<TET-1> kit (Epicentre, Madison, Wis.) and/or primer walking. The sequences were assembled with the Sequencher program (Gene Codes Corp., Ann Arbor, Mich.).

Genes encoding CrtW ketolases were identified by conducting BLAST (Basic Local Alignment Search Tool; Altschul, S. F., et al., *J. Mol. Biol.*, 215:403-410 (1993)) searches for similarity to sequences contained in the BLAST "nr" database (comprising all non-redundant GenBank® CDS translations, sequences derived from the 3-dimensional structure Brookhaven Protein Data Bank, the SWISS-PROT protein sequence database, EMBL, and DDBJ databases). The sequences were analyzed for similarity to all publicly available DNA sequences contained in the "nr" database using the BLASTN algorithm provided by the National Center for Biotechnology Information (NCBI). The DNA sequence was translated in all reading frames and compared for similarity to all publicly available protein sequences contained in the "nr" database using the BLASTX algorithm (Gish, W. and States, D. J., *Nature Genetics*, 3:266-272 (1993)) provided by the NCBI.

All comparisons were done using either the BLASTNnr or BLASTXnr algorithm. The results of the BLAST comparisons are given in Table 3, which summarizes the sequences to which each gene has the most similarity. Table 3 displays data based on the BLASTXnr algorithm with values reported in expect values. The nucleotide and amino acid sequences were also compared with several known ketolase genes using a multiple sequence alignment algorithm in Vector NTI. Table 4 displays the percentage of nucleotide sequence identity and amino acid sequence identity for the pairwise comparisons. The three crtW genes isolated share only moderate homology with the known crtW genes. Furthermore, they are very divergent from each other as shown from the pairwise comparison in Table 4.

TABLE 3

Top BLAST hits for the carotenoid ketolase genes isolated from different bacterial species

| ORF Name | Gene Name | Similarity Identified | SEQ ID base | SEQ ID Peptide | % Identity[a] | % Similarity[b] | E-value[c] | Citation |
|---|---|---|---|---|---|---|---|---|
| 1 | crtW_Sphingomonas melonis DC18 | beta-carotene C4 oxygenase gi\|33439708\|gb\|AAN86030.1crtW [Brevundimonas aurantiaca] | 1 | 2 | 57 | 70 | e-68 | WO 02/079395 |
| 2 | crtW_Brevundimonas vesicularis DC263 | beta-carotene C4 oxygenase gi\|33439708\|gb\|AAN86030.1crtW [Brevundimonas aurantiaca] | 3 | 4 | 63 | 68 | 9e-88 | WO 02/079395 |
| 3 | crtW_Flavobacterium sp. K1-202C | beta-carotene C4 oxygenase gi\|17230681\|ref\|NP_487229.1\|crtW [Nostoc sp. PCC7120] | 5 | 6 | 47 | 62 | 8e-49 | Kaneko et al., DNA Res., 8(5): 205-213 (2001) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

TABLE 4

Pairwise comparison of the nucleotide and amino acid sequences of the three newly isolated crtW sequences with several known crtW sequences

| DNA/AA Identity[a] | Sphingomonas melonis | Brevundimonas vesicularis | Flavobacterium sp. | Agrobacterium aurantiacum[b] | Bradyrhizobium sp.[c] | Brevundimonas aurantiaca[d] | Nostoc sp.[e] |
|---|---|---|---|---|---|---|---|
| Sphingomonas melonis | 100/100 | 52/42 | 35/29 | 57/48 | 56/48 | 61/53 | 38/33 |
| Brevundimonas vesicularis | | 100/100 | 40/32 | 55/45 | 57/48 | 72/70 | 43/34 |
| Flavobacterium sp. | | | 100/100 | 39/31 | 42/32 | 39/32 | 56/41 |
| Agrobacterium aurantiacum | | | | 100/100 | 60/48 | 59/50 | 40/36 |
| Bradyrhizobium sp. | | | | | 100/100 | 62/53 | 44/36 |
| Brevundimonas aurantiaca | | | | | | 100/100 | 43/35 |
| Nostoc sp. | | | | | | | 100/100 |

[a]Percentage of nucleotide sequence identity and amino acid sequence identity.
[b]Agrobacterium aurantiacum, SwissProt Accession Number P54972
[c]Bradyrhizobium sp., GenBank ® Accession Number AF218415
[d]Brevundimonas aurantiaca, GenBank ® Accession Number AY166610
[e] Nostoc sp. PCC7120, Pir Accession Number AF2204

Example 4

Construction of β-Carotene Synthesis Plasmid pDCQ330

P. agglomerans DC404 was an environmental isolate that contained the carotenoid synthesis gene cluster crtEidiYIBZ (SEQ ID NO:12) (see U.S. Ser. No. 10/808,807).

The soil from a residential vegetable garden in Wilmington, Del. was collected and resuspended in LB medium. A 10-μL loopful of resuspension was streaked onto LB plates and the plates were incubated at 30° C. Pigmented bacteria with diverse colony appearances were picked and streaked twice to homogeneity on LB plates and incubated at 30° C. From these colonies, one which formed pale yellow smooth translucent colonies was designated as "strain DC404".

P. agglomerans strain DC404 was grown in 25 mL of LB medium at 30° C. overnight with aeration. Bacterial cells were centrifuged at 4,000× g for 10 min. The cell pellet was gently resuspended in 5 mL of 50 mM Tris-10 mM EDTA (pH 8.0) and lysozyme was added to a final concentration of 2 mg/mL. The suspension was incubated at 37° C. for 1 hr. Sodium dodecyl sulfate was then added to a final concentration of 1% and proteinase K was added at 100 μg/mL. The suspension was incubated at 55° C. for 2 h. The suspension became clear and the clear lysate was extracted twice with an equal volume of phenol:chloroform:isoamyl alcohol (25:24:1) and once with chloroform:isoamyl alcohol (24:1). After centrifuging at 4,000 rpm for 20 min, the aqueous phase was carefully removed and transferred to a new tube. Two volumes of ethanol were added and the DNA was gently spooled with a sealed glass Pasteur pipette. The DNA was dipped into a tube containing 70% ethanol. After air drying, the DNA was resuspended in 400 μL of TE (10 mM Tris-1 mM EDTA, pH 8.0) with RNaseA (100 μg/mL) and stored at 4° C. The concentration and purity of DNA was determined spectrophotometrically by $OD_{260}/OD_{280}$.

A cosmid library of DC404 was constructed using the pWEB cosmid cloning kit from Epicentre (Madison, Wis.) following the manufacturer's instructions. Genomic DNA was sheared by passing it through a syringe needle. The sheared DNA was end-repaired and size-selected on low-melting-point agarose by comparison with a 40 kB standard. DNA fragments approximately 40 kB in size were purified and ligated into the blunt-ended cloning-ready pWEB cosmid vector. The library was packaged using ultra-high efficiency MaxPlax Lambda Packaging Extracts, and plated on EPI100 E. coli cells. Two yellow colonies were identified from the cosmid library clones. The cosmid DNA from the two clones had similar restriction digestion patterns. This cosmid DNA, referred to herein as pWEB-404, contained the crtWEidiYIBZ gene cluster, given as SEQ ID NO:12.

Primers pWEB404F: 5'-GAATTCACTAGTCGAGACGC-CGGGTACCAACCAT-3' (SEQ ID NO:13) and pWEB404R: 5'-GAATTCTAGCGCGGGCGCTGCCAGA-3' (SEQ ID NO:14) were used to amplify a fragment from DC404 containing the crtEidiYIB genes (SEQ ID NO:15) by PCR. Cosmid DNA pWEB-404 was used as the template with Pfu Turbo™ polymerase (Stratagene, La Jolla, Calif.), and the following thermocycler conditions: 92° C. (5 min); 94° C. (1 min), 60° C. (1 min), 72° C. (9 min) for 25 cycles; and 72° C. (10 min). A single product of approximately 5.6 kB was observed following gel electrophoresis. Taq polymerase (Roche Applied Science, Indianapolis, Ind.) was used in a ten minute 72° C. reaction to add additional 3' adenosine nucleotides to the fragment for TOPO® cloning into pTrcHis2-TOPO (Invitrogen). Following transformation to *E. coli* TOP10 cells, several colonies appeared bright yellow in color, indicating that they were producing a carotenoid compound. The gene cluster was then subcloned into the broad host range vector pBHR1 (MoBiTec, LLC, Marco Island, Fla.), and electroporated into *E. coli* 10G cells (Lucigen, Middletown, Wis.). The transformants containing the resulting plasmid pDCQ330 were selected on LB medium containing 50 μg/mL kanamycin. In pDCQ330, a unique SpeI site was engineered upstream of crtE.

Example 5

Expression of a Novel CrtW Carotenoid Ketolase Gene in *E. coli*

This example describes expression of the novel carotenoid ketolase genes in an *E. coli* strain producing β-carotene. Function of the ketolase genes is demonstrated by conversion of β-carotene to canthaxanthin.

The β-carotene producing strain used in this study was the *E. coli* strain containing plasmid pDCQ330, which carried the β-carotene synthesis gene cluster from *Pantoea agglomerans* DC404 (U.S. Ser. No. 10/808,807). The putative ketolase genes from the three bacterial strains were amplified by PCR. The crtW from DC18 was amplified using primers crtW-18_F: 5'-ACTAGTAAGGAGGAATAAAC-CATGACCGTCGATCACGACGCAC-3' (SEQ ID NO:16) and crtW-18_R: 5'-TCTAGACTACCGGTCTTTGCT-TAACGAC-3' (SEQ ID NO:17). The crtW from DC263 was amplified using primers crtW-263_F: 5'-ACTAGTAAG-GAGGGAATAAACCATGCGGCAAGCGAACAGGATG-3' (SEQ ID NO:18) and crtW-263_R: 5'-TCTAGAC-TAGCTGAACAAACTCCACCAG-3' (SEQ ID NO:19). The crtW from K1-202C was amplified using primers crtW/K1-202CF: 5'-ACTAGTAAGGAGGAATAAACCATG-GCTGATGGAGGAAGTGMGG-3' (SEQ ID NO:20) and crtW/K1-202CR: 5'-TCTAGATTAGTTTGATTGAGAT-TCTT-3' (SEQ ID NO:21). The PCR products were cloned into pTrcHis2-TOPO (Invitrogen) vector and screened for clones containing the insert in the forward orientation. These resulted in pDCQ341TA expressing the crtW gene from DC18, pDCQ342TA expressing the crtW gene from DC263, and pDCQ339TA expressing the crtW gene from K1-202C. These constructs were transformed into the β-carotene accumulating *E. coli* strain containing pDCQ330. Orange transformants were obtained and their carotenoids were analyzed by HPLC as described in Example 1. The HPLC results are shown in FIG. 3. Canthaxanthin eluted at 7.29 min was the carotenoid exclusively produced in each of the strain. The canthaxanthin standard was purchased from CaroteNature (Lupsingen, Switzerland). This clearly demonstrated the ketolase function of the three new crtW genes.

Example 6

Co-Expression of Divergent Ketolase Genes in *E. coli*

This example describes co-expression of divergent ketolase genes in an *E. coli* strain producing astaxanthin and intermediates. Expression of the additional ketolase genes increased astaxanthin production.

The crtW and the crtZ genes from *Agrobacterium aurantiacum* were used to produce astaxanthin in a heterologous host such as *E. coli*. We evaluated whether co-expression of a divergent crtW would improve astaxanthin conversion. The three newly isolated carotenoid ketolase genes from DC18, DC263, and K1-202C share only moderate homology with several known crtW ketolase genes as shown in Table 4. Specifically, the crtW gene from DC18 has 57% DNA sequence identity and 48% amino acid sequence identity with the crtW gene (SEQ ID NO:23) from *Agrobacterium aurantiacum*. The crtW from DC263 has 55% DNA sequence identity and 45% amino acid sequence identity with the crtW gene from *Agrobacterium aurantiacum*. The crtW from K1-202C has 39% DNA sequence identity and 31% amino acid sequence identity with the crtW gene from *Agrobacterium aurantiacum*. It is unlikely that the presence of multiple copies of the crtW genes in a single host would cause instability problem due to their moderate to low homologies to each other.

Plasmid pDCQ335 was constructed by cloning the synthetic *Agrobacterium* crtZW genes into the β-carotene synthesis gene cluster in pDCQ330. The crtZ (SEQ ID NO:22) and crtW (SEQ ID NO:23) genes were joined together by SOEing PCR. The crtZ gene was amplified using forward primer crtZW_F: 5'-ACTAGTAAGGAGGAATAAACCAT-GACCAAC-3' (SEQ ID NO:24) and reverse primer crtZW-_soe_R: 5'-AGGGCATGGGCGCTCATGGTATATTC-CTCCTTTCTAGATTAGGTGCGTTCTTGGGCTTC-3' (SEQ ID NO:25). The crtW gene was amplified using forward primer crtZW_soe_F: 5'-GAAGCCCAAGAACG-CACCTAATCTAGAAAGGAGGAATATAC-CATGAGCGCCCATGCCCT-3' (SEQ ID NO:26) and reverse primer crtZW_R: 5'-GCTAGCTGTACAT-CACGCGGTGTCGCCTTTGG-3' (SEQ ID NO:27). The two PCR products were gel purified and joined together by PCR using primers crtZW_F and crtZW_R. The 1272 bp PCR product was cloned into pTrcHis2-Topo vector (Invitrogen) resulting in plasmid pDCQ335TA. The ~1.2 kb NheI/Spe I fragment from pDCQ335TA containing the crtZW genes was ligated to the unique Spe I site in pDCQ330. In the resulting construct pDCQ335, the crtZWEidiYIB genes are organized in an operon and under the control of the chloramphenicol resistant gene promoter of the vector.

Plasmid pDCQ342TA expressing a crtW gene from DC263 and plasmid pDCQ339TA expressing a crtW gene from K1-202C were transformed into *E. coli* cells containing pDCQ335. Plasmid pDCQ335 containing a crtW gene from *Agrobacterium aurantiacum* is compatible with plasmids pDCQ342TA or pDCQ339TA. *E. coli* strains containing pDCQ335 alone and strains containing the additional plasmid pDCQ342TA or pDCQ339TA were grown in LB at 30° C. for 3 days and HPLC analysis was performed as described in Example 1. Results are shown in FIG. 4. Astaxanthin was identified by comparing its elution time, absorption spectra and molecular weight with those of the authentic standard (Sigma, St. Louis, Mo.). Presence of adonixanthin was predicted based on the absorption spectra and its molecular weight (582 Dalton). In the *E. coli* strain containing pDCQ335 alone, approximately 24% of the total carotenoids produced was astaxanthin (5.0 min) and the majority (46%) of the carotenoids produced was adonixanthin (5.6 min). In strains that containing pDCQ335 co-expressed with pDCQ342TA or pDCQ339TA, approximately 50% of carotenoids produced was astaxanthin (4.8-4.9 min) and approximately 10% was adonixanthin (5.5 min). This result demonstrated that co-expression of more than one divergent ketolase genes improved the efficiency of the keto group addition to increase production of ketocarotenoids such as astaxanthin.

Example 7

Construction of β-Carotene Synthesis Plasmid pDCQ340

The purpose of this Example was to prepare a β-carotene expression plasmid, referred to herein as pDCQ340. *Enterobactericeae* DC260 (U.S. Ser. No. 10/808,979; hereby incorporated by reference) contains the natural gene cluster crtEXYIBZ. The genes required for β-carotene synthesis (i.e., crtEYIB) were joined together by PCR. The crtE gene was amplified using primers crt-260_F: 5-GAATTCAC-TAGTACCAACCATGGATAGCCATTATG-3' (SEQ ID NO: 28) and crt-260SOE_R: 5'-ATCAGGTCGCCTCCGC-CAGCACGACTTTCAGTTGAATATCGCTAGCTGTTG-3' (SEQ ID NO: 29). The crtY gene was amplified using primers crt-260SOE_F: 5'-CAACAGCTAGCGATAT-TCAACTGAAAGTCGTGCTGGCGGAGGC-GACCTGAT-3' (SEQ ID NO: 30) and crt-260R1_R: 5'-CATTTTTTCTTCCCTGGTTCGACAGAGT-TCAACAGCGCGCGCAGCGCTT-3' (SEQ ID NO: 31). The crtB genes were amplified using primers crt-260R1_F: 5'-AAGCGCTGCGCGCGCTGTTGAACTCT-GTCGAACCAGGGAAGAAAAAATG-3' (SEQ ID NO: 32) and crt-260_R: 5'-GAATTCAACGAGGACGCTGC-CACAGA-3' (SEQ ID NO: 33). An EcoRI site at the 3' end of the crtY gene was removed by a silent change introduced at the primers spanning the 3' end of the crtY gene. The crtEY genes were first joined together by SOEing PCR using primers crt-260_F (SEQ ID NO: 28) and crt-260R1_R (SEQ ID NO: 31). The crtEY genes were then joined together by PCR with crtIB genes using crt-260_F (SEQ ID NO: 28) primer and crt-260_R (SEQ ID NO: 32) primer. The final 4.5 kB crtEYIB fragment was cloned into pTrcHis2-TOPO vector and then subcloned into pBHR1 resulting pDCQ340. *E. coli* cells containing pDCQ340 were shown to produce β-carotene.

Example 8

Expression of the Novel Carotenoid Ketolase Genes in *Methylomonas*

This example describes how one of skill in the art can express the novel carotenoid ketolase genes for production of ketocarotenoids, such as canthaxanthin, in *Methylomonas* sp. 16a (ATCC PTA-2402) based on previously reported methods (U.S. Ser. No. 09/941,947) and (U.S. Ser. No. 60/527,083).

The crtW genes from *Sphingomonas melonis* DC18 and *Brevundimonas vesicularis* DC263 were individually cloned into the β-carotene synthesis plasmid pDCQ340 (Example 7), creating plasmids pDCQ341 and pDCQ342, respectively.

The plasmids pDCQ341 and pDCQ342 were transferred into *Methylomonas* 16a by tri-parental conjugal mating (U.S. Ser. No. 60/527,083). An *E. coli* helper strain containing pRK2013 (ATCC No. 37159) and an *E. coli* 10G donor strain containing the plasmid pDCQ341 or pDCQ342 were grown overnight in LB medium containing kanamycin (50 μg/mL), washed three times in LB, and resuspended in a volume of LB representing approximately a 60-fold concentration of the original culture volume.

The *Methylomonas* sp. 0.16a MWM1200 strain contains a double crossover knockout of the promoter for the native crtN1aldcrtN2 gene cluster and a knockout of the native crtN3 gene, disrupting the synthesis of the native $C_{30}$ carotenoids (U.S. Ser. No. 60/527,083). This MWM1200 strain can be grown as the recipient using the general conditions described in U.S. Ser. No. 09/941,947. Briefly, *Methylomonas* 16a MWM1200 strain was grown in serum stoppered Wheaton bottles (Wheaton Scientific, Wheaton Ill.) using a gas/liquid ratio of at least 8:1 (i.e., 20 mL of Nitrate liquid "BTZ-3" media in 160 mL total volume) at 30° C. with constant shaking.

Nitrate Medium for *Methylomonas* 16A

Nitrate liquid medium, also referred to herein as "defined medium" or "BTZ-3" medium was comprised of various salts mixed with Solution 1 as indicated below (Tables 5 and 6) or where specified the nitrate was replaced with 15 mM ammonium chloride. Solution 1 provides the composition for 100-fold concentrated stock solution of trace minerals.

TABLE 5

Solution 1*

|  | MW | Conc. (mM) | g per L |
|---|---|---|---|
| Nitriloacetic acid | 191.1 | 66.9 | 12.8 |
| $CuCl_2 \times 2H_2O$ | 170.48 | 0.15 | 0.0254 |
| $FeCl_2 \times 4H_2O$ | 198.81 | 1.5 | 0.3 |
| $MnCl_2 \times 4H_2O$ | 197.91 | 0.5 | 0.1 |
| $CoCl_2 \times 6H_2O$ | 237.9 | 1.31 | 0.312 |
| $ZnCl_2$ | 136.29 | 0.73 | 0.1 |
| $H_3BO_3$ | 61.83 | 0.16 | 0.01 |
| $Na_2MoO_4 \times 2H_2O$ | 241.95 | 0.04 | 0.01 |
| $NiCl_2 \times 6H_2O$ | 237.7 | 0.77 | 0.184 |

*Mix the gram amounts designated above in 900 mL of $H_2O$, adjust to pH = 7, and add $H_2O$ to an end volume of 1 L. Keep refrigerated.

TABLE 6

Nitrate liquid medium (BTZ-3)**

|  | MW | Conc. (mM) | g per L |
|---|---|---|---|
| $NaNO_3$ | 84.99 | 10 | 0.85 |
| $KH_2PO_4$ | 136.09 | 3.67 | 0.5 |
| $Na_2SO_4$ | 142.04 | 3.52 | 0.5 |
| $MgCl_2 \times 6H_2O$ | 203.3 | 0.98 | 0.2 |
| $CaCl_2 \times 2H_2O$ | 147.02 | 0.68 | 0.1 |
| 1 M HEPES (pH 7) | 238.3 |  | 50 mL |
| Solution 1 |  |  | 10 mL |

**Dissolve in 900 mL $H_2O$. Adjust to pH = 7, and add $H_2O$ to give 1 L. For agar plates: Add 15 g of agarose in 1 L of medium, autoclave, let cool down to 50° C., mix, and pour plates.

The standard gas phase for cultivation contains 25% methane in air. The *Methylomonas* sp. 16a MWM1200 recipient strain was cultured under these conditions for 48 h in BTZ-3 medium, washed three times in BTZ-3, and resuspended in a volume of BTZ-3 representing a 150-fold concentration of the original culture volume.

The donor, helper, and recipient cell pastes were combined in ratios of 1:1:2, respectively, on the surface of BTZ-3 agar plates containing 0.5% (w/v) yeast extract. Plates were maintained at 30° C. in 25% methane for 16-72 hours to allow conjugation to occur, after which the cell pastes were collected and resuspended in BTZ-3. Dilutions were plated on BTZ-3 agar containing kanamycin (50 µg/mL) and incubated at 30° C. in 25% methane for up to 1 week. Orange-red transconjugants were streaked onto BTZ-3 agar with kanamycin (50 µg/mL).

For analysis of carotenoid composition, transconjugants were cultured in 25 mL BTZ-3 containing kanamycin (50 µg/mL) and incubated at 30° C. in 25% methane as the sole carbon source for up to 1 week. The cells were harvested by centrifugation and frozen at −20° C. After thawing, the pellets were extracted and carotenoid content was analyzed by HPLC, as described in Example 1.

HPLC analysis (FIG. 5) of extracts from *Methylomonas* 16a MWM1200 containing pDCQ340 showed synthesis of β-carotene. *Methylomonas* 16a MWM1200 containing either pDCQ341 or pDCQ342 synthesized canthaxanthin, which confirmed the ketolase activity of the novel ketolases in this methanotrophic host.

What is claimed is:

1. An isolated nucleic acid molecule encoding a carotenoid ketolase enzyme, selected from the group consisting of:
   (a) an isolated nucleic acid molecule encoding an amino acid as set forth in SEQ ID NO:4;
   (b) an isolated nucleic acid molecule that hybridizes with (a) under the following wash conditions: 0.1×SSC, 0.1% SDS, 65° C.; or
   an isolated nucleic acid molecule that is fully complementary to (a), or (b).

2. An isolated nucleic acid molecule according to claim 1 as set fourth in SEQ ID NO:3.

3. A polypeptide encoded by the isolated nucleic acid molecule of claim 1.

4. An isolated nucleic acid molecule encoding a carotenoid ketolase enzyme, the enzyme of 259 amino acid that has at least 95% identity based on the Smith-Waterman method of alignment when compared to a polypeptide having the sequence as set forth in SEQ ID NO:4; or a second nucleotide sequence comprising the complement of the first nucleotide sequence.

5. A chimeric gene comprising the isolated nucleic acid molecule of any one of claim 1, or 2, operably linked to suitable regulatory sequences.

6. A transformed host cell comprising the isolated nucleic acid molecule of claim 1.

7. The transformed host cell of claim 6 wherein the host cell is selected from the group consisting of bacteria, yeast, filamentous fungi, algae, and green plants.

8. The transformed host cell of claim 7 wherein the host cell is selected from the group consisting of *Aspergillus, Trichoderma, Saccharomyces, Pichia, Candida, Hansenula,* or *Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus.*

9. The transformed host cell of claim 7 wherein the host cell is a $C_1$ metabolizing bacteria.

10. The transformed host cell of claim 7 wherein the host cell is selected from the group consisting of soybean, rapeseed, sunflower, cotton, corn, tobacco, alfalfa, wheat, barley, oats, sorghum, rice, *Arabidopsis*, cruciferous vegetables, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

* * * * *